United States Patent
Tavernier et al.

(10) Patent No.: US 11,053,300 B2
(45) Date of Patent: Jul. 6, 2021

(54) MEMBRANE SPAN-KINASE FUSION PROTEIN AND THE USES THEREOF

(71) Applicants: VIB VZW, Ghent (BE); Universiteit Gent, Ghent (BE)

(72) Inventors: Jan Tavernier, Balegem (BE); Samuel Lievens, Aalter (BE)

(73) Assignees: VIB VZW, Ghent (BE); Universiteit Gent, Ghent (BE)

( * ) Notice: Subject to any disclaimer, the term of this patent is extended or adjusted under 35 U.S.C. 154(b) by 0 days.

(21) Appl. No.: 16/444,910

(22) Filed: Jun. 18, 2019

(65) Prior Publication Data

US 2019/0330310 A1    Oct. 31, 2019

Related U.S. Application Data

(62) Division of application No. 14/381,502, filed as application No. PCT/EP2013/054507 on Mar. 6, 2013, now Pat. No. 10,336,811.

(30) Foreign Application Priority Data

Mar. 6, 2012 (EP) .................................. 12158276

(51) Int. Cl.
| | | |
|---|---|---|
| *C07K 14/72* | (2006.01) | |
| *C07K 14/705* | (2006.01) | |
| *C12N 9/12* | (2006.01) | |
| *C12N 15/62* | (2006.01) | |
| *C12N 9/02* | (2006.01) | |
| *C12Q 1/66* | (2006.01) | |
| *G01N 33/58* | (2006.01) | |
| *G01N 33/74* | (2006.01) | |

(52) U.S. Cl.
CPC .......... *C07K 14/723* (2013.01); *C07K 14/705* (2013.01); *C12N 9/0069* (2013.01); *C12N 9/12* (2013.01); *C12N 15/62* (2013.01); *C12Q 1/66* (2013.01); *C12Y 207/10002* (2013.01); *G01N 33/581* (2013.01); *G01N 33/74* (2013.01); *C07K 2319/42* (2013.01); *C07K 2319/61* (2013.01); *G01N 2333/726* (2013.01); *G01N 2333/90241* (2013.01); *G01N 2333/91205* (2013.01); *G01N 2500/02* (2013.01); *G01N 2500/10* (2013.01)

(58) Field of Classification Search
CPC ....... G01N 2500/02; G01N 33/74; C12N 9/12
USPC ..................................................... 435/188, 7
See application file for complete search history.

(56) References Cited

U.S. PATENT DOCUMENTS

| 5,637,463 A | 6/1997 | Dalton et al. |
| 5,658,791 A | 8/1997 | Wilks et al. |
| 5,776,689 A | 7/1998 | Karin et al. |
| 2013/0131957 A1 | 5/2013 | Jiang et al. |
| 2014/0030746 A1 | 1/2014 | Tavernier et al. |

FOREIGN PATENT DOCUMENTS

| WO | 9002809 A1 | 3/1990 |
| WO | 9220791 A1 | 11/1992 |
| WO | 9710330 A1 | 3/1997 |
| WO | 9732017 A1 | 9/1997 |
| WO | 9834948 A1 | 8/1998 |
| WO | 0017221 A1 | 3/2000 |
| WO | 0158923 A2 | 8/2001 |
| WO | 0190188 A2 | 11/2001 |
| WO | 2004099419 A2 | 11/2004 |
| WO | 2012117031 A1 | 9/2012 |
| WO | 2013131957 A1 | 9/2013 |

OTHER PUBLICATIONS

Stagljar, et al., A genetic system based on split-ubiquitin for the analysis of interactions between membrane proteins in vivo. Proc Natl Acad Sci U S A. Apr. 28, 1998; 95(9):5187-92. PubMed PMID: 9560251; PubMed Central PMCID: PMC20236.
Berchtold et al, Cytokine receptor-independent, constitutively active variants of STAT5. J Biol Chem. Nov. 28, 1997;272(48):30237-43.
Bovijn et al., Identification of Interaction Sties for Dimerization and Adapter Recruitment in Toll/Interleukkn-1 Receptor (TIR) Domain of Toll-like Receptor 4, Journal of Biological Chemistry, Dec. 2, 2011, pp. 4088-4098, vol. 287, No. 6.
Cheng et al, Arsenic inhibition of the JAK-STAT pathway. Oncogene(2004)23, 3603-3612.
Constantinescu et al, Mining for JAK-STAT mutations in cancer. Trends in Biochemical Sciences 2008 vol. 33 No. 3 p. 122-131.
Duhe et al, Characterization of the in vitro kinase activity of a partially purified soluble GST/JAK2 fusion protein. Molecular and Cellular Biochemistry 236: 23-35, 2002.
Eyckerman et al, Design and application of a cytokinereceptor-based interaction trap. Nature Cell Biology vol. 3 Dec. 2001 p. 1114-1119.
Hanyaloglu et al, (2002) Homo- and hetero-oligomerization of thyrotropin-releasing hormone (TRH) receptor subtypes. Differential regulation of beta-arrestins 1 and 2. J. Biol. Chem. 277, 50,422-50,430.

(Continued)

*Primary Examiner* — Sheridan Swope
(74) *Attorney, Agent, or Firm* — Patent Law Works, LLP

(57) ABSTRACT

The disclosure relates to a recombinant membrane span protein complex, comprising (1) a fusion protein, comprising a membrane span protein fused to a kinase domain, preferably a constitutive kinase and (2) a reporter construct comprising a polypeptide, interacting with the membrane span protein, fused to a reporter phosphorylation domain. The disclosure relates further to the uses of such membrane span protein complex for the detection of compounds that interact with the membrane span protein and for the screening and/or detection of inhibitors of the compound-membrane span protein interactions. In a preferred embodiment, the membrane span protein is a G protein coupled receptor (GPCR) and the method is used for the screening and/or detection of inhibitors of the ligand-receptor binding.

11 Claims, 9 Drawing Sheets

Specification includes a Sequence Listing.

(56) References Cited

OTHER PUBLICATIONS

Jin et al, Interaction of the mu-opioid receptor with GPR177 (Wntless) inhibits Wnt secretion: potential implications for opioid dependence. BMC Neurosci. Mar. 9, 2010;11:33. doi: 10.1186/1471-2202-11-33.

Kiu, et al. "Biology and Significance of the Jak/stat Signalling Pathways." Growth Factors. 30.2 (2012): 88-106.

Lievens, et al., "Kinase Substrate Sensor (kiss), a Mammalian<i>in Situ</i>protein Interaction Sensor." Molecular & Cellular Proteomics. 13.12 (2014): 3332-3342.

Nyfeler, B, S W.et al. "Capturing Protein Interactions in the Secretory Pathway of Living Cells." Proceedings of the National Academy of Sciences. 102.18 (2005): 6350-6355.

Oh et al, A receptor-independent, cell-based JAK activation assay for screening for JAK3-specific inhibitors. Journal of Immunological Methods 354 (2010) 45-52.

PCT International Search Report and Written Opinion, Application No. PCT/EP2013/054507, dated May 17, 2013, 10 pages.

Tavernier et al., MAPPIT: a cytokine receptor-based two-hybrid method in mammalian cells, Clin Exp. Allergy, Jan. 1, 2002, pp. 1397-404.

Urech et al, Cell growth selection system to detect extracellular and transmembrane protein interactions. Biochimica et Biophysica Acta 1622 (2003) 117-127.

MEMBRANE SPAN-KINASE FUSION PROTEIN AND THE USES THEREOF

CROSS-REFERENCE TO RELATED APPLICATIONS

This application is a divisional of U.S. patent application Ser. No. 14/381,502, filed Aug. 27, 2014, pending, which is a national phase entry under 35 U.S.C. § 371 of International Patent Application PCT/EP2013/054507, filed Mar. 6, 2013, designating the United States of America and published in English as International Patent Publication WO 2013/131957 A1 on Sep. 12, 2013, which claims the benefit under Article 8 of the Patent Cooperation Treaty to European Application Serial No. 12158276.1, filed Mar. 6, 2012, the disclosure of each of which is hereby incorporated herein in its entirety by this reference.

TECHNICAL FIELD

The disclosure relates to a recombinant membrane span protein complex, comprising (1) a fusion protein, comprising a membrane span protein fused to a kinase domain, preferably a constitutive kinase and (2) a reporter construct comprising a polypeptide, interacting with the membrane span protein, fused to a reporter phosphorylation domain. The disclosure relates further to the uses of such membrane span protein complex for the detection of compounds that interact with the membrane span protein and for the screening and/or detection of inhibitors of the compound-membrane span protein interactions. In a preferred embodiment, the membrane span protein is a G protein coupled receptor (GPCR) and the method is used for the screening and/or detection of inhibitors of the ligand-receptor binding.

BACKGROUND

Several methods have been developed to detect protein—protein interactions, all with their advantages and limitations. Co-purification of proteins and co-immunoprecipitation were amongst the first techniques used. However, these methods are tedious and do not allow high throughput screening. Moreover, they require lysis corrupting the normal cellular context. A major breakthrough was obtained by the introduction of the genetic approaches, of which the yeast two-hybrid (Fields and Song, 1989) is the most important one. Although this technique became widely used, it has several drawbacks. The fusion proteins need to be translocated to the nucleus, which is not always evident. Proteins with intrinsic transcription activation properties may cause false positives. Moreover, interactions that are dependent upon secondary modifications of the protein such as phosphorylation cannot be easily detected.

Several alternative systems have been developed to solve one or more of these problems.

Approaches based on phage display do avoid the nuclear translocation. WO9002809 describes how a binding protein can be displayed on the surface of a genetic package, such as a filamentous phage, whereby the gene encoding the binding protein is packaged inside the phage. Phages, which bear the binding protein that recognizes the target molecule, are isolated and amplified. Several improvements of the phage display approach have been proposed, as described, e.g., in WO9220791, WO9710330 and WO9732017.

However, all these methods suffer from the difficulties that are inherent at the phage display methodology: the proteins need to be exposed at the phage surface and are so exposed to an environment that is not physiological relevant for the in vivo interaction. Moreover, when screening a phage library, there will be a competition between the phages that results in a selection of the high affinity binders.

U.S. Pat. No. 5,637,463 describes an improvement of the yeast two-hybrid system, whereby can be screened for modification dependent protein-protein interactions. However, this method relies on the co-expression of the modifying enzyme, which will exert its activity in the cytoplasm and may modify other enzymes than the one involved in the protein-protein interaction, which may on its turn affect the viability of the host organism.

An interesting evolution is described in U.S. Pat. No. 5,776,689, by the so-called protein recruitment system. Protein-protein interactions are detected by recruitment of a guanine nucleotide exchange factor (Sos) to the plasma membrane, where Sos activates a Ras reporter molecule. This results in the survival of the cell that otherwise would not survive in the culture conditions used. Although this method has certainly the advantage that the protein-protein interaction takes place under physiological conditions in the submembranary space, it has several drawbacks. Modification-dependent interactions cannot be detected. Moreover, the method is using the pleiotropic Ras pathway, which may cause technical complications. Most of these drawbacks were solved by the Mammalian Protein-Protein Interaction Trap (MAPPIT) described in WO0190188, using recruitment of a prey to a cytokine type of receptor, fused to a bait. However, although this method allows to study protein-protein interactions under physiological conditions, it is not suitable to study interactions involving integral membrane proteins, particularly multispan membrane proteins, including GPCR's.

Methods for studying the interaction of proteins with a GPCR are mainly focused on ligand-receptor binding. WO9834948 discloses a GPCR wherein the amino terminus is replaced by the amino-terminus of a self-activating receptor, and the use of this construct for the detection of agonists and antagonists. WO2004099419 discloses a ligand upregulatable GPCR, and the use of this construct to screen ligands. WO0158923 describes methods for detecting GPCR activity, methods for assaying GPCR activity and methods for screening GPCR ligands, G-protein-coupled receptor kinase activity and compounds that interact with the GPCR regulatory process, by an enzyme complementation assay. However, this system is rather insensitive, with a maximal window of a factor 2 at the highest concentrations of agonist or antagonist used. Moreover, the system needs a mutation in arrestin, to improve arrestin binding, in order to obtain the required sensitivity.

SUMMARY OF THE DISCLOSURE

Surprisingly, we found that by replacing the enzyme complementation by a detection system of a reporter phosphorylation polypeptide by a kinase, preferably a mutant kinase, even more preferably a constitutive mutant kinase, or an inactive mutant kinase that is activated by addition of an exogenous small molecule, the detection window could be increased significantly. Moreover, using a specific signaling pathway starting from the reporter phosphorylation site, several reporter systems can be used.

A first aspect of the disclosure is a recombinant membrane span protein complex, comprising (1) a first fusion protein, comprising a membrane span protein fused to either a kinase domain or a reporter phosphorylation domain, and (2) a second fusion protein comprising a polypeptide, interacting with the membrane span protein, fused to either a reporter phosphorylation domain or a kinase domain, complementary to the first fusion protein. "Complementary to the first fusion protein," as used herein, means that in case the first fusion protein is a fusion to a kinase domain, the second fusion protein is a fusion to a reporter phosphorylation domain and vice versa: if the first fusion protein is a fusion to a reporter phosphorylation domain, the second fusion protein is a fusion to a kinase domain. In the normal two hybrid technology, the membrane span protein acts as a first interaction protein and is indicated as "bait" and the second fusion protein acts as second interaction protein and is indicated as "prey." Preferably, the kinase domain is a mutant kinase domain. In one preferred embodiment, the mutant kinase domain is a constitutive mutant kinase domain. In another preferred embodiment, the mutant kinase domain is an inactive mutant kinase domain that is activated by addition of an exogenous small molecule. Several embodiments of the disclosure are represented in FIG. 1.

In one preferred embodiment, the kinase is a constitutive kinase mutant derived from Tyk2, such as, but not limited to, a constitutive Tyk2 deletion mutant or and/or a Tyk2 V678F mutant. Derived from Tyk2, as used herein, means that the kinase is a part of the human Tyk2 non-receptor tyrosine-protein kinase (Genbank accession number NP_003322; version NP_003322.3; SEQ ID NO:1) or a mutant or variant thereof wherein the part shows constitutive kinase activity. A variant, as a non-limiting example, is a homologue, paralogue or orthologue. "Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. "Orthologues" and "paralogues" encompass evolutionary concepts used to describe the ancestral relationships of genes. "Paralogues" are genes within the same species that have originated through duplication of an ancestral gene; "orthologues" are genes from different organisms that have originated through speciation, and are also derived from a common ancestral gene. Preferably, the homologue, "orthologue" or "paralogue" has a sequence identity at protein level of at least 50%, 51%, 52%, 53%, 54% or 55%, 56%, 57%, 58%, 59%, preferably 60%, 61%, 62%, 63%, 64%, 65%, 66%, 67%, 68%, 69%, more preferably 70%, 71%, 72%, 73%, 74%, 75%, 76%, 77%, 78%, 79%, even more preferably 80%, 81%, 82%, 83%, 84%, 85%, 86%, 87%, 88%, 89% most preferably 90%, 91%, 92%, 93%, 94%, 95%, 96%, 97%, 98%, 99% or more as measured in a BLASTp (Altschul et al., 1997; Altschul et al., 2005). Variants and parts thereof, according to the disclosure, do show kinase activity. Preferably, the part is a part with constitutive kinase activity, preferably fragment 589-1187 of SEQ ID NO:1. Alternatively, the part is the part, corresponding to fragment 589-1187 of SEQ ID NO:1 in a homologue, paralogue or orthologue as defined above, wherein the part has constitutive kinase activity. In an alternative embodiment the constitutive kinase is a constitutive kinase derived from a Jak kinase, preferably from a Jak kinase selected from the group consisting of Jak1 (Accession number P23458, version P23458.2), Jak2 (Accession number 060674, version 060674.2) and Jak3 (Accession number P52333, version P52333.2) or a mutant or variant thereof, as defined above. Preferably, the constitutive kinase is a constitutive Jak2 deletion mutant. In still another alternative embodiment, the constitutive kinase is a constitutive kinase derived from a Src kinase (Accession number NP_005408, version NP_005408.1) or a mutant or variant thereof, as defined above. Preferably, the Src derived kinase is a kinase as depicted in SEQ ID NO:8.

In another preferred embodiment, the mutant tyrosine kinase is an inactive mutant that is activated by addition of an exogenous small molecule. Such mutant kinase is known to the person skilled in the art, and has been described, as a non-limiting example, by Qiao et al., (2006) as a Src 388R/A mutant or a 391R/A mutation in the corresponding human Src protein (Accession number NP_938033, version NP_938033.1), or a mutant or variant thereof, as defined above. Alternatively, it may be a similar mutation in the Jak kinase family, such as, but not limited to, Tyk2 1027R/A, or a mutant or variant thereof.

A membrane span protein may be any membrane span protein known to the person skilled in the art. Membranes include, but are not limited to, the cellular membrane, the endoplasmatic reticulum and the mitochondrial membrane. A "membrane span" means that the protein crosses the membrane, while sticking out at both sides of the membrane. The "membrane span protein," as used herein, may contain a single membrane span, or multiple membrane spans. Preferably, the membrane span protein is a multiple membrane span protein, comprising at least two membrane spans, even more preferably, the membrane span protein is a cellular membrane multispan membrane protein, most preferably the membrane span protein is a GPCR. A GPCR chain, as used herein, means any polypeptide chain with 7 transmembrane spans that can function as a G-protein coupled receptor. In a preferred embodiment, it is a known GPCR; however, for the disclosure, the original GPCR may carry mutations, insertions and/or deletions, and/or extension at the amino terminal and/or carboxyterminal end, as long as the capacity of binding with a ligand is not inhibited by the mutations or modifications.

Preferably, the kinase domain is fused at, or in the cytoplasmic part of the membrane span protein. In one preferred embodiment, the kinase domain is fused in a cytoplasmic loop of a multispan membrane span protein, preferably in a cytoplasmic loop of a GPCR chain. In another preferred embodiment, the kinase domain is fused to the carboxyterminal end of the membrane span protein. The fusion may be direct, i.e., by direct coupling of the kinase domain to the carboxyterminal end of the membrane span protein chain, or it may be indirect, using a linker sequence between the membrane span protein chain and the kinase domain. In case of a fusion within the membrane span protein chain, the linker may be situated at one side of the kinase domain, or at both sides. Preferably, the linker is shorter than 20 amino acids, more preferably shorter than 10 amino acids, even more preferably between 5 and 10 amino acids, most preferably 6 amino acids.

A reporter phosphorylation domain can be any domain that comprises a tyrosine, wherein the tyrosine can be phosphorylated by a tyrosine kinase. Preferably, the reporter phosphorylation domain is derived from or comprises a fragment of gp130, even more preferably the reporter phosphorylation domain consists of a fragment of gp130. Most preferably, the reporter phosphorylation domain consists of SEQ ID NO:2

Another aspect of the disclosure is the use of a recombinant membrane span protein complex, according to the disclosure, to detect compound-protein interaction, preferably protein-protein interactions. Detection of the compound-protein or protein-protein interaction may be direct or indirect. Direct detection of an interaction is the detection of the interaction of a fusion protein (fused to a reporter phosphorylation domain or a kinase domain), recruited to the membrane span protein chain (fused to a kinase domain or a reporter phosphorylation domain, complementary to the recruited fusion protein) wherein the membrane span protein or a domain thereof act as first interaction protein. In this case, the interaction of the first and second interaction protein brings the reporter phosphorylation domain close to the kinase domain and the interaction is detected by phosphorylation of the reporter phosphorylation domain. Indirect detection of an interaction is the detection of the phosphorylation of the reporter phosphorylation domain, wherein the reporter phosphorylation domain is brought in contact to the kinase domain by recruitment of a fusion protein to the receptor upon a compound-protein interaction that induces the recruitment of the fusion protein. Such compound-protein interaction may be, as a non-limiting example, the ligand-receptor binding, wherein ligand means every compound that can bind to the extracellular domain of a receptor and that is able to initiate the signaling pathway by binding to the extracellular domain. Initiating, as used herein, means starting the events that normally directly follow the binding of the ligand to the extracellular domain of a receptor, e.g., multimerization for a multimerizing receptor, but it does not imply activation of the receptor and/or accomplishing of the signaling pathway. Compound means any chemical or biological compound, including simple or complex organic or inorganic molecules, peptides, peptido-mimetics, proteins, antibodies, carbohydrates, nucleic acids or derivatives thereof. In a special embodiment, the fusion protein that is recruited to the membrane span protein (fused to a reporter phosphorylation domain or a kinase domain) may be another membrane span protein fused to a kinase domain or a reporter phosphorylation domain, complementary to that of the recruiting fusion protein, allowing the detection of homodimerization, homomultimerization, heterodimerization or heteromultimerization of membrane span proteins.

The detection of the phosphorylation of the reporter phosphorylation domain can be by any method known to the person skilled in the art. In one preferred embodiment, the reporter phosphorylation is inducing a signaling pathway, preferably a STAT3 dependent pathway, resulting in the activation of a reporter gene, such as a luciferase gene. Alternatively, the phosphorylation of the reporter phosphorylation domain may be detected directly, e.g., by phosphorylation dependent binding of an antibody, or by detection of intermediates of the signaling pathway such as STAT3 dimers. Still another alternative reporter system consist of a protein complementation assay, wherein one part of the protein is incorporated in or associated with the cytoplasmic protein complex, according to the disclosure, and the second part of the protein is recruited to the phosphorylated reporter phosphorylation site, leading to a detectable activity of the reconstituted protein. Preferably, the readout of the receptor system has a window of at least a factor 4, preferably at least a factor 5, even more preferably at least a factor 10. The readout window is defined as the ration of the signal to the noise (negative control).

Still another aspect of the disclosure is the use of a recombinant membrane span protein complex, according to the disclosure, to screen inhibitors of a compound-protein interaction, preferably a protein-protein interaction. Indeed, it is clear for the person skilled in the art that, if the compound-protein interaction is giving a detectable signal, inhibitors of the compound-protein interactions can be screened by adding compounds to the test system and screening for those compounds that disturb the detectable signal.

The eukaryotic cell can be any eukaryotic cell capable of expressing a membrane span protein, including but not limited to, yeast cells, fungal cells and mammalian cells. Preferably, the cell is a mammalian cell. In one preferred embodiment, the eukaryotic host cells comprising the recombinant membrane span protein chain fused to a kinase domain (or a reporter phosphorylation domain) are transformed with a library of polypeptides, all fused to the reporter phosphorylation domain (or a kinase domain, if the membrane span protein is fused to a reporter phosphorylation domain). Cells, in which the reporter phosphorylation domain will be phosphorylated are comprising a prey-reporter phosphorylation domain construct that is capable of interacting with the membrane span protein chain. In another preferred embodiment, the eukaryotic host cell comprises a recombinant GPCR chain fused to a kinase domain (or a reporter phosphorylation domain) and the cell is transformed with a polypeptide, capable of interacting with the membrane span protein chain upon activation of the GPCR by ligand binding, wherein the polypeptide is fused to the reporter phosphorylation domain (or a kinase domain, respectively), and the cell is contacted with compounds that may act as ligand. Binding of such compound to the GPCR will induce the recruitment of the polypeptide-phosphorylation domain fusion and result in the phosphorylation of the reporter phosphorylation domain. Polypeptide, as used herein, means any proteinaceous structure, independent of the length and includes molecules such as peptides, phosphorylated proteins and glycosylated proteins. Polypeptide, as used herein, is not necessarily indicating an independent compound but can also be used to indicate a part of a bigger compound, such as a domain of a protein.

Another aspect of the disclosure, is a method to detect compound-protein interactions, the method comprising (1) transforming a eukaryotic host cell with a first fusion protein, comprising a recombinant membrane span protein chain, fused to either a kinase domain or a reporter phosphorylation domain (2) transforming the same host cell with at least one second fusion protein, comprising a polypeptide, fused to either a reporter phosphorylation domain or a kinase domain, complementary to the first fusion protein wherein the polypeptide is capable of interacting with the membrane span protein chain (3) adding the compound to be tested to the cell (4) optionally adding the ligand to the cell and (5) detecting the phosphorylation of the reporter phosphorylation domain. The sequence of the transformation steps may be inverted; a ligand is added in cases where the compound is not tested as a ligand; in this case, the steps of adding compound and ligand may be interchanged.

Still another aspect of the disclosure is a method to screen inhibitors of a compound-protein interaction, the method comprising 1) transforming a eukaryotic host cell with first fusion protein, comprising a recombinant membrane span protein chain, fused to a either kinase domain or a reporter phosphorylation domain (2) transforming the same host cell with at least one second fusion protein, comprising a polypeptide, fused to a either a reporter phosphorylation domain or a kinase domain, complementary to the first fusion protein, wherein the polypeptide is interacting with the membrane span protein chain (3) adding at least one possible inhibitor molecule (4) adding the ligand to the cell and (5) detecting the phosphorylation of the reporter phosphorylation domain. Preferably, the same set up without inhibitor is used as positive control for the protein-protein interaction. The sequence of the transformation steps may be inverted; the steps of adding inhibitor and ligand may be interchanged.

Definitions

The following definitions are set forth to illustrate and define the meaning and scope of various terms used to describe the disclosure herein.

Protein, as used herein, means a chain composed of amino acids, independent of the length. The terms "protein" and "polypeptide" are interchangeable. The protein can be modified by modifications such as, but not limited to, phosphorylation, glycosylation, ubiquitinilation and acetylation.

Domain, as used herein, is a part of a polypeptide, wherein the part may carry a specific function, such as, but not limited to, an enzymatic center or a phosphorylation site.

Protein complex, as used herein, means a structure that comprises at least two, non-covalently linked, protein molecules. Protein complexes can consist of more than two proteins, and include other molecules that are not proteins. Some non-limiting examples of such molecules are metal ions, ATP, or carbohydrate molecules.

A kinase, as used herein, is a polypeptide that can transfer a phosphate group to an amino acid of the same or another polypeptide. Preferably, the amino acid is a serine, a threonine or a tyrosine. Even more preferably, the amino acid is embedded in a phosphorylation site. A phosphorylation site, as used herein, is a pattern of several amino acids, preferably comprising a serine, threonine or a tyrosine, and determining the amino acid that will be phosphorylated by the kinase. Most kinases can occur in an inactive and in an active state, wherein the reporter phosphorylation site is only phosphorylated in the active state of the kinase. Kinases can be switched from the inactive from to the active form by phosphorylation, or by other modifications such as proteolysis, or by mutation. The phosphorylation can be autophosphorylation, crossphosphorylation (by a protein complex of identical kinases) or by action of another kinase.

Constitutive, as used herein, means that the kinase is continuously in the active state, normally as a consequence of a mutation, or by proteolytic cleavage removing an inhibitor. Constitutive kinases are known to the person skilled in the art and comprise, but are not limited to, truncated forms of Tyk2, truncated forms of Src kinase and point mutations such as Tyk2 (V678F), Jak1 (V658F) and Jak2(V617F).

An inactive kinase mutant means that the mutant form shows a kinase activity that is significantly lower than the original non-mutated form. Preferably, the remaining activity is lower than 50% of the original activity, even more preferably lower than 20%, more preferably lower than 10%, most preferably lower than 5% of the original activity.

Activated by the addition an exogenous small compound, as used herein, means that the activity of the inactive kinase is partly or totally restored by addition of a small compound to the cells, whereby the small compound, exogenous to the cell, is taken up by the cell and activates the kinase as an intracellular exogenous compound. "Activated by the addition an exogenous small compound" is used to make a distinction with ligand-receptor induced activation, where a ligand is binding to the extracellular part of a receptor, and induces activation of the kinase. "Exogenous," as used herein, means that the compound is normally not present in the cell.

Reporter phosphorylation site is the site that is phosphorylated in the protein complex upon interaction of the first and the second interaction polypeptide; it is distinct from a possible phosphorylation site in the kinase domain that is autophosphorylated in the constitutive kinase.

First interaction polypeptide, as used herein, is a polypeptide of which one wants to study the interaction with one or more compounds. The first interaction polypeptide is normally referred to as a "bait" in the two hybrid terminology.

Second interaction polypeptide, as used herein, is a polypeptide that is presented to study its interaction with the first interaction polypeptide. The second interaction polypeptide is normally referred to as a "prey" in the two hybrid terminology. It is clear for the person skilled in the art that the first and the second interaction polypeptide are interchangeable in the disclosure, in this respect that either a "bait" or a "prey" may be fused to constitutive kinase, according to the disclosure. Indeed, the resulting protein complex will have an identical overall composition, composed of the four essential elements (first interaction polypeptide, second interaction polypeptide, constitutive kinase and reporter phosphorylation site), and independent whether the first interaction polypeptide is fused to the constitutive kinase or the reporter phosphorylation site (wherein the second interaction polypeptide is then fused to the reporter phosphorylation site, and the constitutive kinase, respectively), the interaction of the first with the second interacting polypeptide will lead to the formation of a cytoplasmic protein complex, according to the disclosure, and will result in the phosphorylation of the reporter phosphorylation site. In one preferred embodiment, the first and the second interaction protein are identical to study homodimerization or homomultimerization of a protein. In another preferred embodiment, the first and the second protein are different, allowing to study protein-protein interactions of heterodimers or heteromultimers.

Compound means any chemical or biological compound, including simple or complex organic or inorganic molecules, peptides, peptido-mimetics, proteins, antibodies, carbohydrates, nucleic acids or derivatives thereof.

Interaction means any interaction, be it direct or indirect. A direct interaction implies a contact between the interaction partners. An indirect interaction means any interaction whereby the interaction partners interact in a complex of more than two compounds. This interaction can be completely indirect, with the help of one or more bridging compounds, or partly indirect, where there is still a direct contact that is stabilized by the interaction of one or more compounds.

Figure 1A:
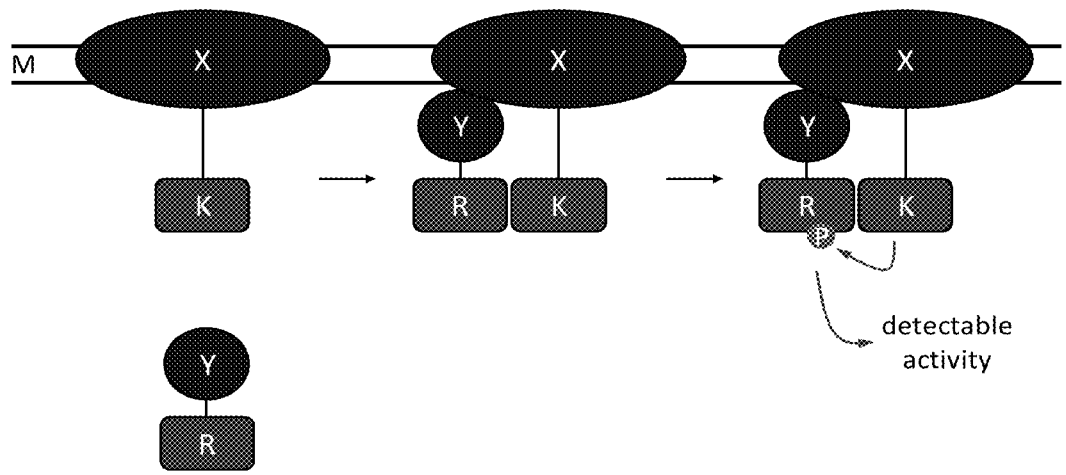
FIG. 1: Schematic representation of different embodiments of the recombinant membrane span protein complex, according to the disclosure. "M" depicts a membrane.
Figure 1B:
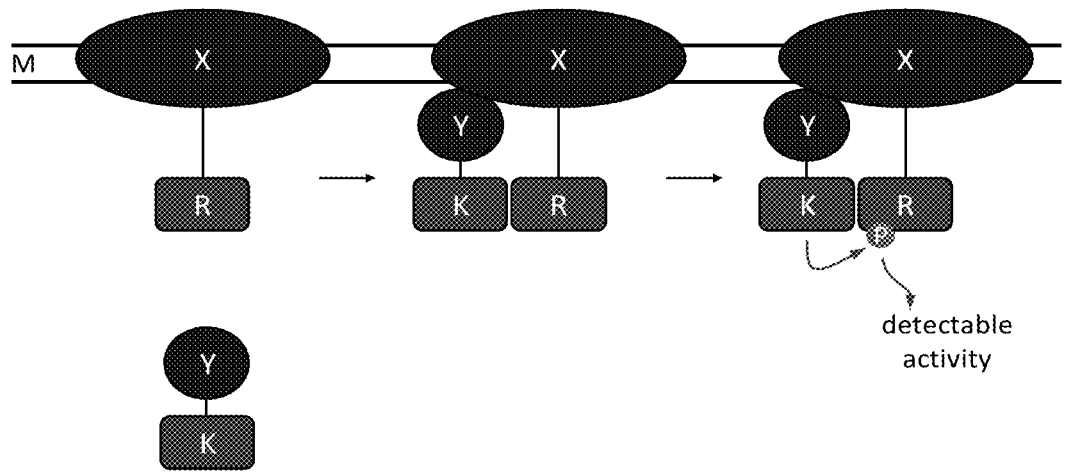
Figure 1C:
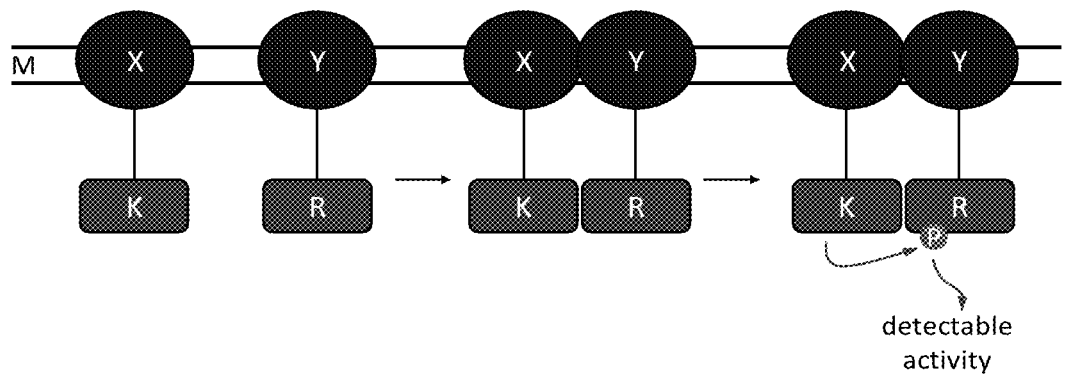

A. A membrane span protein (X) is fused to a constitutive kinase (K) and a polypeptide (Y) is fused to a reporter phosphorylation site (R). Interaction between the membrane span protein X and the polypeptide Y results in the reporter phosphorylation site being phosphorylated (P) by the constitutive kinase, leading to a detectable activity.

B. A membrane span protein (X) is fused to a reporter phosphorylation site (R) and a polypeptide (Y) is fused to a constitutive kinase (K). Interaction between the membrane span protein X and the polypeptide Y results in the reporter phosphorylation site being phosphorylated (P) by the constitutive kinase, leading to a detectable activity.

C. A membrane span protein (X) is fused to a constitutive kinase (K) and a second membrane span protein (Y) is fused to a reporter phosphorylation site (R). Interaction between the membrane span proteins X and Y results in the reporter phosphorylation site being phosphorylated (P) by the constitutive kinase, leading to a detectable activity.

FIG. 2: Detection of the ligand-dependent interaction between human somatostatin receptor 2 (SSTR2) and human beta arrestin 2 (ARRB2) in an assay variant that comprises mutant Tyk2 kinase fusion proteins.

A. Schematic overview of the assay. The membrane span protein (X) is fused to the C-terminal region of Tyk2 comprising the kinase domain, whereas the polypeptide interacting with the membrane span protein (Y) is fused to a fragment of gp130 which contains phosphorylation sites. When membrane span protein X and the polypeptide Y interact, the Tyk2 kinase domain phosphorylates the phosphorylation sites of gp130. STAT3 transcription factors are recruited to these phosphorylated sites and are in turn phosphorylated by the Tyk2 kinase domain, which results in their activation. Dimers of activated STAT3 transcription factors are able to bind the specific rPAPI promoter, which drives the expression of a firefly luciferase reporter gene. The activity of this reporter gene is measured as light production in a luciferase detection assay using a luminometer.

B. Application to the analysis of ligand-dependent interaction between SSTR2 and ARRB2. Cells were transfected with the indicated combination of plasmids, and either left untreated (NS) or treated with increasing doses (0.1-1-10 µM) of somatostatin:
 a) pMet7-HA-Tyk2(C)+pMG2-ARRB2+pXP2d2-rPAPI-luciferase
 b) pMet7-SSTR2-Tyk2(C)–HA+pMG2-SVT+pXP2d2-rPAPI-luciferase
 c) pMet7-SSTR2-Tyk2(C)–HA+pMG2-ARRB2+pXP2d2-rPAPI-luciferase Luciferase activity is shown as fold induction relative to the luciferase activity measured in untreated cells. Error bars indicate standard deviation.

C. Detection of the ligand-dependent interaction between SSTR2 and ARRB2 using an alternative expression vector. Cells were transfected with the indicated combination of plasmids, and either left untreated (NS) or treated with increasing doses (0.1-1-10 µM) of somatostatin:
 a) pSVSport-HA-Tyk2(C)+pMG2-ARRB2+pXP2d2-rPAPI-luciferase
 b) pSVSport-SSTR2-Tyk2(C)–HA+pMG2-SVT+pXP2d2-rPAPI-luciferase
 c) pSVSport-SSTR2-Tyk2(C)–HA+pMG2-ARRB2+pXP2d2-rPAPI-luciferase Luciferase activity is shown as fold induction relative to the luciferase activity measured in untreated cells. Error bars indicate standard deviation.

D. Dose-response curve of the ligand-dependent interaction between SSTR2 and ARRB2. Cells were transfected with a combination of the plasmids pMet7-SSTR2-Tyk2(C)–HA, pMG2-ARRB2 and pXP2d2-rPAPI-luciferase, and treated with increasing concentrations of somatostatin (SST-14). Luciferase activity is shown as relative light units (rlu). Error bars indicate standard deviation.

Figure 3A:
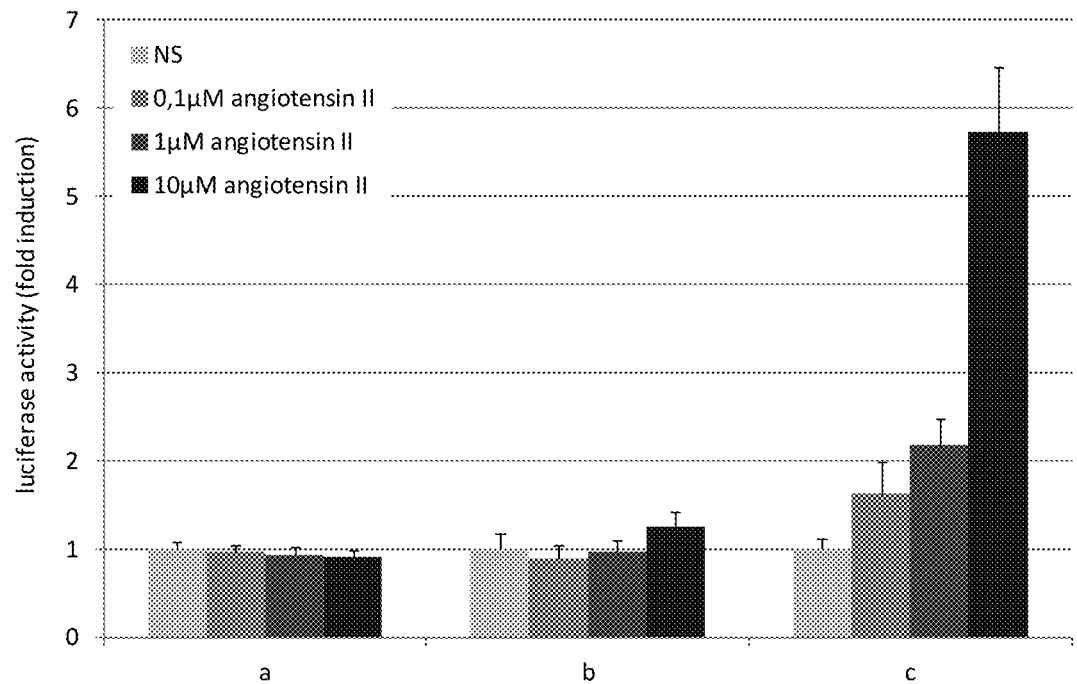

FIG. 3: Analysis of the interaction between human angiotensin receptor 1 (AGTR1) and ARRB2.

A. Detection of the ligand-dependent interaction between AGTR1 and ARRB2. Cells were transfected with the indicated combination of plasmids, and either left untreated (NS) or treated with increasing doses (0.1-1-10 µM) of angiotensin II:
 a) pMet7-HA-Tyk2(C)+pMG2-ARRB2+pXP2d2-rPAPI-luciferase
 b) pMet7-AGTR1-Tyk2(C)–HA+pMG2-SVT+pXP2d2-rPAPI-luciferase
 c) pMet7-AGTR1-Tyk2(C)–HA+pMG2-ARRB2+pXP2d2-rPAPI-luciferase Luciferase activity is shown as fold induction relative to the luciferase activity measured in untreated cells. Error bars indicate standard deviation.

B. Dose-response curve of the ligand-dependent interaction between AGTR1 and ARRB2. Cells were transfected with a combination of the plasmids pMet7-AGTR1-Tyk2(C)–HA, pMG2-ARRB2 and pXP2d2-rPAPI-luciferase, and treated with increasing concentrations of angiotensin II (AngII). Luciferase activity is shown as relative light units (rlu). Error bars indicate standard deviation.

Figure 4:
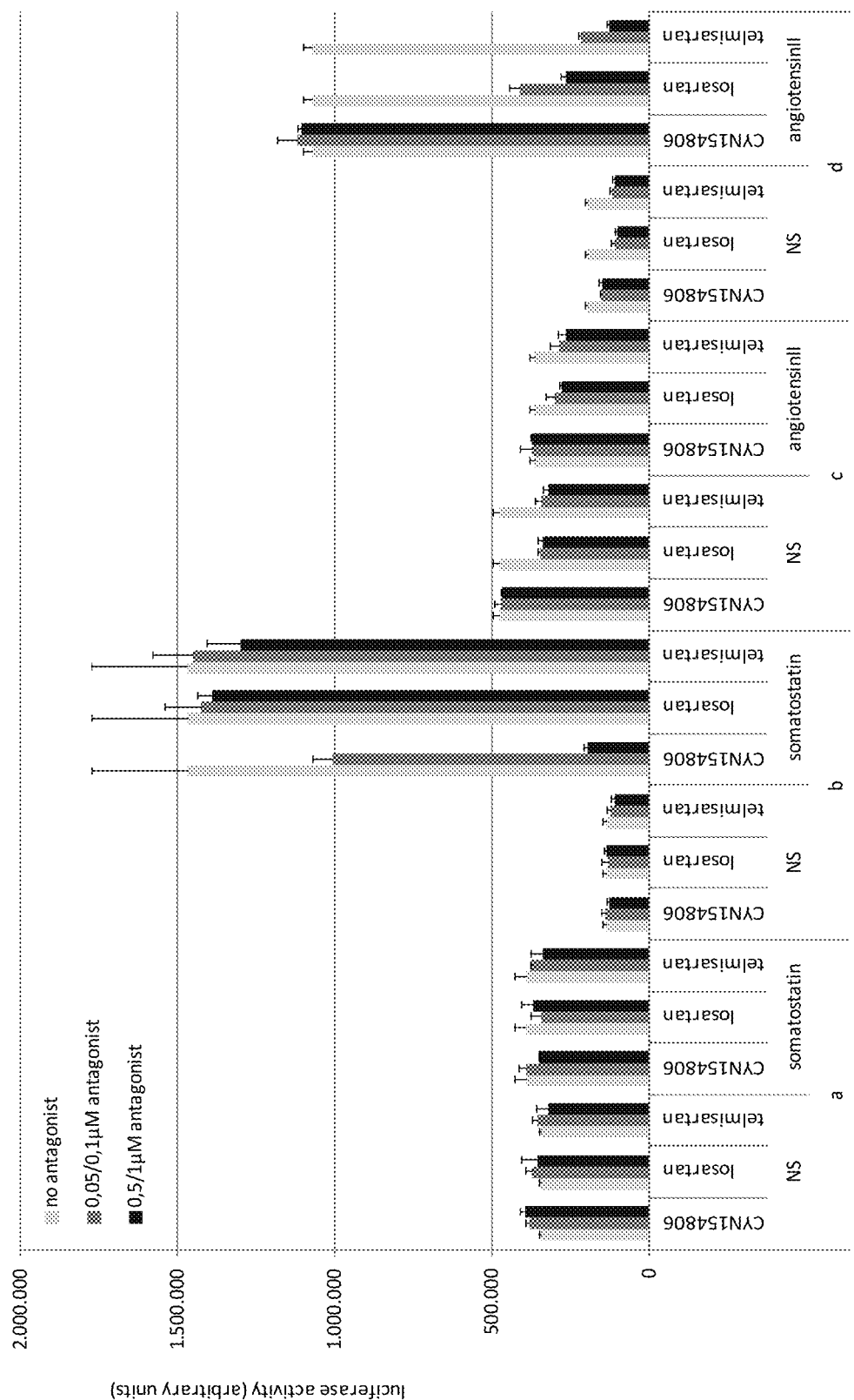

FIG. 4: Evaluation of the effect of GPCR antagonists on the interaction between GPCRs and ARRB2. Cells were transfected with the indicated combination of plasmids, and treated with the indicated combinations of GPCR ligand and antagonist (ligand: 1 µM somatostatin for transfections a and b, 10 µM angiotensin II for transfections c and d; antagonists: 0.05 or 0.5 µM CYN154806; 0.1 or 1 µM losartan or telmisartan):
 a) pMet7-SSTR2-Tyk2(C)–HA+pMG1-EFHA1+pXP2d2-rPAPI-luciferase
 b) pMet7-SSTR2-Tyk2(C)–HA+pMG2-ARRB2+pXP2d2-rPAPI-luciferase
 c) pMet7-AGTR1-Tyk2(C)–HA+pMG1-EFHA1+pXP2d2-rPAPI-luciferase
 d) pMet7-AGTR1-Tyk2(C)–HA+pMG2-ARRB2+pXP2d2-rPAPI-luciferase Luciferase activity is shown as arbitry light units. Error bars indicate standard deviation.

Figure 5A:
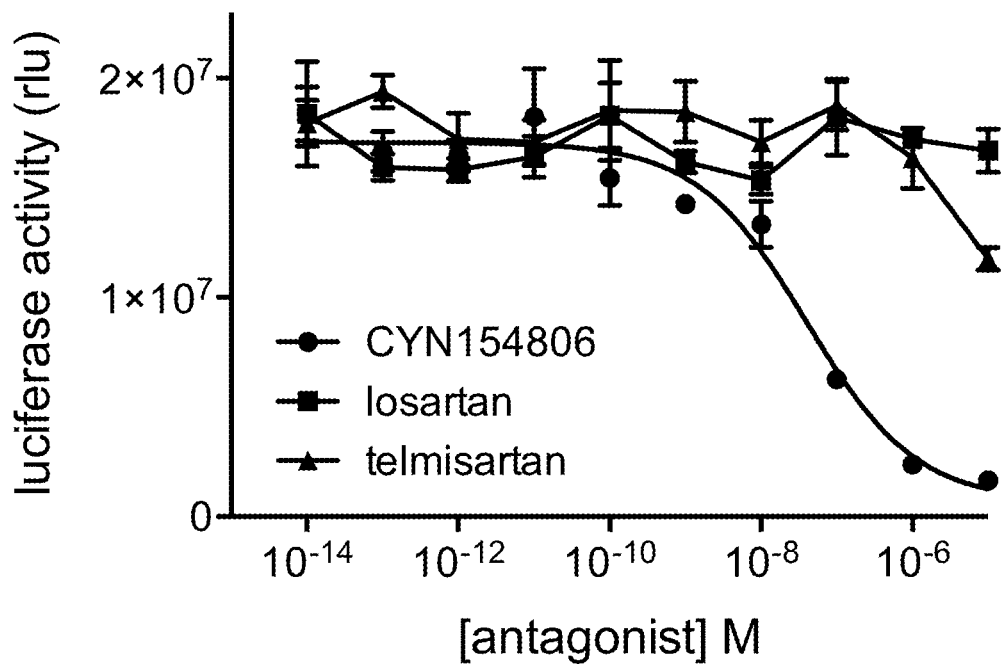
Figure 5B:
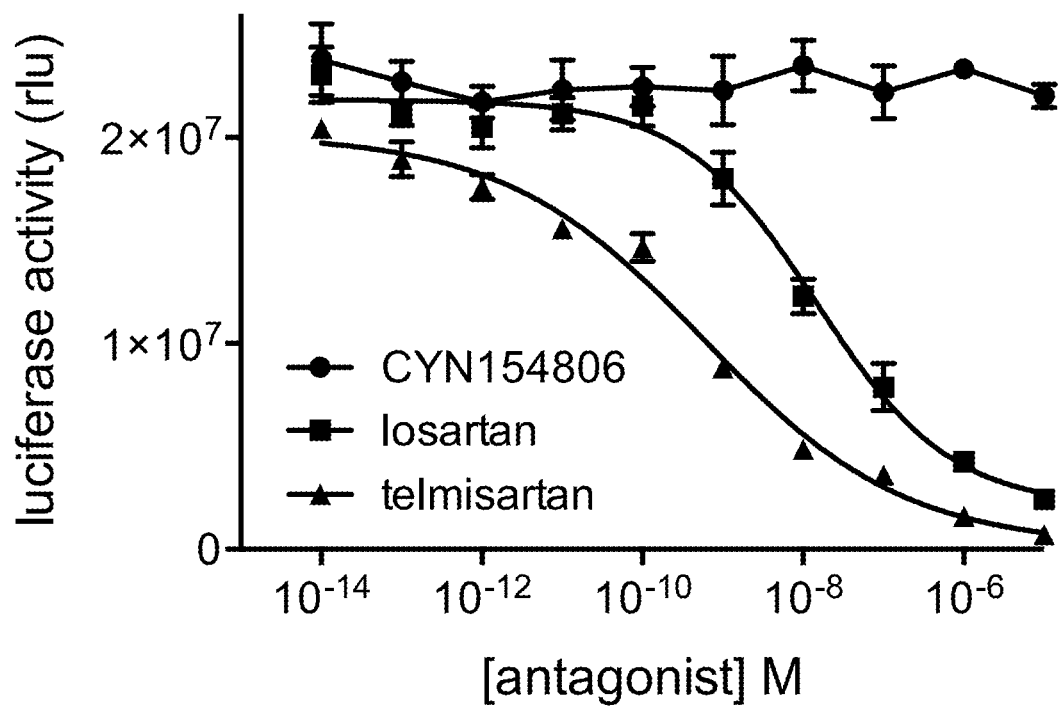

FIG. 5: Dose-dependent effect of GPCR antagonists on the detection of the interaction between GPCRs and ARRB2.

A. Analysis of the effect of GPCR antagonists in an assay measuring the interaction between SSTR2 and ARRB2. Cells were transfected with the following combination of plasmids: pMet7-SSTR2-Tyk2(C)–HA+pMG2-ARRB2+pXP2d2-rPAPI-luciferase. Cells were either left untreated, treated with 10 µM somatostatin or treated with a combination of 10 µM somatostatin and increasing doses ($10^{-13}$M up to $10^{-6}$M) of either GPCR antagonist (CYN154806, losartan, telmisartan). Luciferase activity is shown as relative light units (rlu). Error bars indicate standard deviation.

B. Analysis of the effect of GPCR antagonists in an assay measuring the interaction between AGTR1 and ARRB2. Cells were transfected with the following combination of plasmids: pMet7-AGTR1-Tyk2(C)–HA+pMG2-ARRB2+pXP2d2-rPAPI-luciferase. Cells were either left untreated, treated with 10 µM angiotensin II or treated with a combination of 10 µM angiotensin II and increasing doses ($10^{-13}$M up to $10^{-6}$M) of either GPCR antagonist (CYN154806, losartan, telmisartan). Luciferase activity is shown as relative light units (rlu). Error bars indicate standard deviation.

FIG. 6: Analysis of ERN1 dimerization.

A. Detection of ERN1 dimerization upon induction of ER (endoplasmatic reticulum)-stress by treatment with tunicamycin. Cells were transfected with the following plasmids:
 a) pcDNA5/FRT/TO-ERN1-Tyk2(C)–HA+pMG1+pXP2d2-rPAPI-luciferase
 b) pcDNA5/FRT/TO-ERN1-Tyk2(C)–HA+pMG2C-ERN1 pXP2d2-rPAPI-luciferase After transfection, cells were treated with 0-0.5-1-2 µg/ml tunicamycin, final concentration. Error bars indicate standard deviation.

B. Detection of ERN1 dimerization upon induction of ER-stress by treatment with tunicamycin. Cells were transfected with the following plasmids:
  a) pcDNA5/FRT/TO-ERN1-Tyk2(C)–HA+pMG1+pXP2d2-rPAPI-luciferase
  b) pcDNA5/FRT/TO-ERN1-Tyk2(C)–HA pMG2C-ERN1 pXP2d2-rPAPI-luciferase
  c) pcDNA5/FRT/TO-ERN1-Tyk2(C)–HA pMG2C-ERN1cyt+pXP2d2-rPAPI-luciferase After transfection, cells were treated with increasing doses tunicamycin. Luciferase activity is shown as fold induction relative to the luciferase signal obtained in cells transfected with unfused gp130 (transfection a) and treated with the same concentration tunicamycin. Error bars indicate standard deviation. Expression of Tyk2(C) and gp130 fusion constructs was evaluated through Western blot applying anti-HA and anti-gp130 antibodies, respectively. Beta-actin expression was stained as a control for equal loading.

C. Analysis of ERN1 structure-function relationship. Cells were transfected with the pXP2d2-rPAPI-luciferase plasmid combined with the indicated Tyk2(C) fusion constructs (pcDNA5/FRT/TO-ERN1-Tyk2(C)–HA, pcDNA5/FRT/TO-ERN1(K599A)-Tyk2(C)–HA or pcDNA5/FRT/TO-ERN1(D123P)-Tyk2(C)–HA) and gp130 fusion constructs (pMG1, encoding unfused gp130 or pMG2C-ERN1 encoding ERN1-gp130), and treated with either tunicamycin or vehicle control (DMSO). Luciferase activity is shown as fold induction relative to the luciferase signal obtained in cells transfected with unfused gp130. Error bars indicate standard deviation. Expression of Tyk2(C) fusion constructs was evaluated through Western blot applying an anti-HA antibody. Beta-actin expression was stained as a control for equal loading.

D. Detection of disruptors of ERN1 dimerization. Cells were transfected with the following plasmids:
  a) pcDNA5/FRT/TO-ERN1-Tyk2(C)–HA+pMG1+pXP2d2-rPAPI-luciferase
  b) pcDNA5/FRT/TO-ERN1-Tyk2(C)–HA+pMG2C-ERN1 pXP2d2-rPAPI-luciferase After transfection, cells were treated with tunicamycin or vehicle control (DMSO) combined with increasing doses of Irestatin 9389. Luciferase activity of cells transfected with gp130-fused ERN1 (transfection b) is shown as fold induction relative to the luciferase signal obtained in cells transfected with unfused gp130 (transfection a) and treated with the same concentration of vehicle or tunicamycin with Irestatin 9389. Error bars indicate standard deviation.

Figure 7:
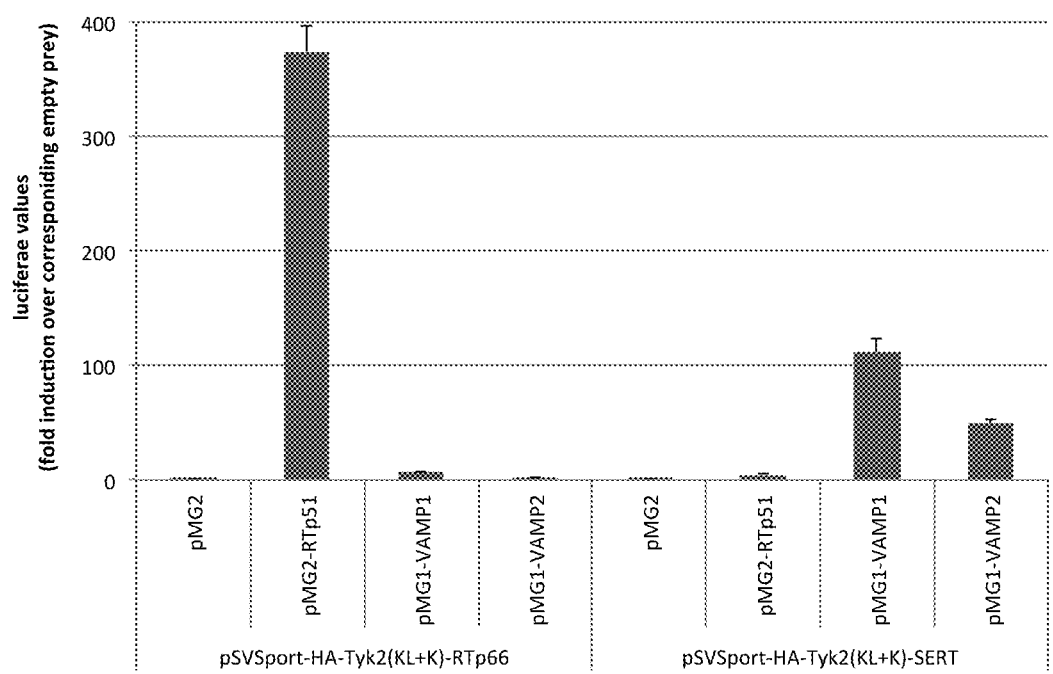

FIG. 7: Detection of the interaction between the serotonin transporter (SERT) and synaptobrevins 1 and 2 (VAMP1 and VAMP2). Cells were transfected with the pXP2d2-rPAPI-luciferase plasmid combined with the indicated Tyk2(C) and gp130 fusion constructs. Luciferase activity is shown as fold induction relative to the luciferase signal obtained in cells transfected with unfused gp130 (pMG2). Error bars indicate standard deviation.

EXAMPLES

Materials and Methods to the Disclosure
Plasmids Used in the Examples

A first type of plasmids express chimeric proteins consisting of an HA-tagged C-terminal portion of human Tyk2 fused at its N-terminus to the membrane span protein and are generated in the pMet7 vector, which contains a strong constitutive hybrid SRα promoter (Takebe et al., 1988). A pMet7-dest-Tyk2(C)–HA Gateway destination vector was constructed by first amplifying the Gateway cassette from the pMG1 Gateway destination vector (Lievens et al., 2009) using primers 1 and 2 (see Table below). These primers contained an AgeI and PspOMI restriction enzyme recognition site, respectively, and these enzymes were used to digest the PCR amplicon. Next, the sequence encoding the C-terminal end of human Tyk2 comprising the kinase domain (starting from amino acids 589 and omitting the stop codon) was amplified by PCR on cDNA from HEK293 cells with primers 3 and 4 (see Table below). The former primer contained a NotI restriction site, whereas the latter contained an HA-tag coding sequence as well as an XbaI restriction enzyme recognition site. The PCR amplicon was digested with NotI and XbaI and, together with the AgeI and PspOMI cut fragment described above, ligated in the AgeI-XbaI cut pMet7 vector to generate the pMet7-dest-Tyk2(C)–HA Gateway destination vector. The pMet7-SSTR2-Tyk2(C)–HA and pMet7-AGTR1-Tyk2(C)–HA plasmids were produced by Gateway recombination mediated transfer of the full length sequence of human SSTR2 and AGTR1, respectively, from entry vectors of the hORFeome collection (Lamesch et al., 2007) into the pMet7-dest-Tyk2(C)–HA Gateway destination vector. Using the restriction enzymes EcoRI and MluI, the SSTR2-Tyk2(C)–HA insert (SEQ ID NO:3) of pMet7-SSTR2-Tyk2(C)–HA was subcloned into pSVSport (Invitrogen) to generate pSVSport-SSTR2-Tyk2(C)–HA. The AGTR1-Tyk2-HA construct is depicted in SEQ ID NO:4.

The control plasmids pMet7-HA-Tyk2(C) and pSVSport-HA-Tyk2(C), which are made of the same C-terminal Tyk2 fragment as described above, an HA-tag at the 5' end and a multiple cloning site at the 3' end were generated by PCR amplification of the Tyk2 sequence on the pMet7-dest-Tyk2(C)–HA template vector using primers 5 and 6 (see Table below). These primers contain an MfeI site and an HA-tag coding sequence together with an XbaI restriction site, respectively. The MfeI-XbaI digested amplicon was ligated both in the EcoRI-XbaI digested pMet7 vector to result in pMet7-HA-Tyk2(C), and in the EcoRI-XbaI digested pSVSport vector (Invitrogen) to generate pSVSport-HA-Tyk2(C).

pSVSport-HA-Tyk2(C)–RTp66 was produced by transfer of the RTp66 insert from pMG2-RTp66 (Pattyn et al., 2008) to pSVSport-HA-Tyk2(C) using the EcoRI and NotI restriction sites. The HA-Tyk2(C)–RTp66 construct is depicted in SEQ ID NO:28. To generate the pSVSport-HA-Tyk2(C)–SERT plasmid, human SERT was amplified on a SERT containing plasmid template using primers 18 and 19, containing EcoRV and NotI restriction sites, respectively. The amplicon was digested with EcoRV, rendered blunt end by the use of Pfu DNA polymerase and subsequently cut with NotI. This fragment was ligated in pSVSport-HA-Tyk2(C) that was cut with EcoRI, rendered blunt end through Pfu DNA Polymerase treatment and subsequently cut with NotI. The HA-Tyk2(C)–SERT construct is shown in SEQ ID NO:29.

To generate the pcDNA5/FRT/TO-ERN1-Tyk2(C)–HA plasmid, human ERN1 was amplified with primers 9 and 10, containing HindIII and NotI restriction enzyme recognition sites, respectively, using an ERN1 entry clone from the hORFeome collection (Lamesch et al., 2007) as a template. The sequence encoding the C-terminal end of human Tyk2 comprising the kinase domain (starting from amino acids 589 and omitting the stop codon) was amplified by PCR on cDNA from HEK293 cells with primers 11 and 12. The former primer contained a NotI restriction site, whereas the latter contained an HA-tag coding sequence as well as an ApaI restriction enzyme recognition site. The PCR amplicon was digested with NotI and ApaI and, together with the HindIII and NotI cut ERN1 fragment described above, ligated into the HindIII-ApaI cut pcDNA5/FRT/TO vector (Invitrogen) to generate the pcDNA5/FRT/TO-ERN1-Tyk2 (C)–HA expression plasmid. The ERN1-Tyk2-HA fusion is depicted in SEQ ID NO:5. The pcDNA5/FRT/TO-ERN1 (K599A)-Tyk2(C)–HA plasmid was generated similarly, by amplifying ERN1 from a plasmid containing ERN1(K599A) instead of WT ERN1. The pcDNA5/FRT/TO-ERN1 (D123P)-Tyk2(C)–HA plasmid was generated through site-directed mutagenesis of the pcDNA5/FRT/TO-ERN1-Tyk2 (C)–HA plasmid using primers 16 and 17. The amino acid sequence of the ERN1 (K599A)-Tyk2(C)–HA en ERN1 (D123P)-Tyk2(K)-HA fusion proteins is depicted in SEQ ID NOS:30 and 31, respectively.

The plasmids encoding the fusions with the second interacting polypeptide were of the type also used in MAPPIT, designated pMG2 (WO0190188, Eyckerman et al., 2001; Lemmens et al., 2003). These plasmids encode fusion proteins of the second interacting polypeptide coupled to a fragment of the human gp130 cytokine receptor chain, which contains multiple tyrosine residues that, upon phosphorylation, make up recruitment sites for STAT3. The SV40 large T containing control plasmid pMG2-SVT was generated by transfer of the SVT insert from the previously described pMG1-SVT plasmid (Eyckerman et al., 2001) into the pMG2 vector using EcoRI and NotI restriction enzymes. Human ARRB2 was PCR amplified on an ARRB2 entry clone from the hORFeome collection (Lamesch et al., 2007) using primers 7 and 8 (see Table below) and exchanged with the SVT insert of pMG2-SVT using EcoRI and NotI restriction sites to generate pMG2-ARRB2. pMG1-EFHA1, pMG1-VAMP1 and pMG1-VAMP2 were generated by Gateway recombination mediated transfer of the full length sequences of human EFHA1, VAMP1 and VAMP2, respectively, from entry vectors of the hORFeome collection (Lamesch et al., 2007) into a Gateway compatible version of the pMG1 vector as described earlier (Lievens et al., 2009). The flag tag-gp130-ARRB2, flag tag-gp130-VAMP1 and flag tag-gp130-VAMP2 fusion constructs are depicted in SEQ ID NOS:6, 32 and 33, respectively.

The pMG2C-ERN1 plasmid encoding a fusion protein of the human ERN1 protein N-terminally coupled to a fragment of the human gp130 cytokine receptor chain was generated by PCR amplification of the ERN1 encoding sequence on an ERN1 entry clone from the hORFeome collection (Lamesch et al., 2007) using primers 13 and 14 and cloning this into a MAPPIT vector containing a gp130 encoding sequence at the 3' end of a Flag-tag encoding sequence and a multi-cloningsite (Pattyn et al., 2008) using EcoRI and XhoI restriction enzymes. The flag tag-ERN1-gp130 fusion construct is depicted in SEQ ID NO:7. The pMG2C-ERN1cyt plasmid encoding a fusion protein of the cytoplasmic portion of the human ERN1 protein fused N-terminally to the gp130 fragment was produced by amplifying the ERN1 cytoplasmic domain on an ERN1 entry clone (see higher) using primers 15 and 14 and cloning this into a MAPPIT vector containing a gp130 encoding sequence using EcoRI and XhoI restriction enzymes, similarly to described above. The flag-tag-ERN1cyt-gp130 fusion construct is depicted in SEQ ID NO:34.

pMG2-RTp51 has been described elsewhere (Pattyn et al., 2008). The flag tag-gp130-RTp51 fusion construct sequence is shown in SEQ ID NO:35. The pMG1 and pMG2 plasmids encoding an unfused gp130 receptor fragment were obtained by cutting out the MAPPIT prey insert of a pMG1 vector using EcoRI and XhoI or of a pMG2 vector using EcoRI and SalI, respectively, blunting the vector backbone through Pfu DNA Polymerase and self-ligation. The amino acid sequence of the polypeptide encoded by pMG1 and pMG2 is depicted in SEQ ID NOS:36 and 37, respectively.

The reporter plasmid pXP2d2-rPAPI-luciferase used in the examples contains the STAT3-dependent rPAPI (rat Pancreatitis-Associated Protein I) promoter driving a firefly luciferase reporter gene as described previously (WO0190188, Eyckerman et al., 2001).

Transfection Procedure

Transfections were carried out using a standard calcium phosphate method. HEK293-T cells were seeded in black tissue-culture treated 96-well plates at 10.000 cells/well in 100 µl culture medium (DMEM supplemented with 10% FCS). Twenty-four hours later, plasmid DNA mixes were prepared that contained plasmids encoding fusion proteins with the first and second interacting proteins and reporter plasmids. The DNA was supplemented with 5 µl 2.5M $CaCl_2$) and double distilled water to a final volume of 50 µl. This mixture was added drop wise to 50 µl 2×HeBS buffer (280 mM NaCl, 1.5 mM $Na_2HPO_4$, 50 mM Hepes; pH 7.05) while vigorously vortexing. After incubation at room temperature for 15 min. to allow DNA precipitates to form, the solution was added to the cells at 10 µl/well. Cells were incubated at 37° C., 8% CO2. Twenty-four hours after transfection, cells were treated with the indicated amounts of ligand, either alone or combined with the indicated amount of antagonist. In the case of Irestatin 9389, cells were pre-treated with the antagonist before adding vehicle (DMSO) or tunicamycin. Another twenty-four hours later, luciferase activity was measured using the Luciferase Assay System kit (Promega) on a TopCount luminometer (Perkin-Elmer). Each transfection was done in triplicate and the average of the luciferase activity readings was used in the calculations.

Induction of Dimerization

Tunicamycin (Sigma T7765; 2 mg/ml stock in DMSO) was diluted in culture medium and added to the cells 24 h prior to luciferase signal read-out.

(Ant)Agonists Applied in the Examples

Somatostatin (Sigma 51763) and angiotensin II (Sigma A9525) were solubilized in PBS to make stock concentrations of 500 µM and 10 mM, respectively. CYN154806 trifluoroacetate salt (Sigma C2490) and losartan potassium (Fluka 61188) were dissolved in PBS at a final concentration of 500 µM and 10 mM, respectively. Telmisartan (Sigma T8949) was dissolved in DMSO at a concentration of 10 mM. Irestatin 9389 (Axxon Medchem) was dissolved in DMSO at a concentration of 50 mM.

Western Blotting

Cells were lysed in 1×CCLR buffer (25 mM Tris-phosphate (pH 7.8), 2 mM DTT, 2 mM CDTA (trans-1,2-diaminocyclo-hexane-N,N,N,N-tetra acetic acid), 10% glycerol, 1% Triton X-100). Lysates were centrifuged and supernatants were separated by SDS-PAGE. Proteins were detected by immunoblotting using rat anti-HA (Roche), rabbit anti-gp130 (Santa Cruz Biotechnology) or mouse anti-beta-actin (Sigma) antibodies.

| Oligonucleotide primer | Sequence (5' > 3') |
|---|---|
| 1 | CCCACCGGTCCGGAATTGACAAGTTTGTACAAAAAAGC (SEQ ID NO: 9) |
| 2 | GGGGGGCCCCAACCACTTTGTACAAGAAAGC (SEQ ID NO: 10) |

-continued

| Oligonu-cleotide primer | Sequence (5' > 3') |
|---|---|
| 3 | CCCGCGGCCGCTGGCGGTTCGATCACCCAGCTGTCCCACTT GG (SEQ ID NO: 11) |
| 4 | TCTAGACTAAGCATAATCTGGAACATCATATGGATACTCGA GGCACACGCTGAACACTGA AGG (SEQ ID NO: 12) |
| 5 | CCCCAATTGACCATGTATCCATATGATGTTCCAGATTATGC TTTAATTAAAATCACCCAGCTGTCCCACTTGG (SEQ ID NO: 13) |
| 6 | GGGTCTAGAGCGGCCGCACCGGTCTTAATTAAGTCGACGAA TTCGCACACGCTGAACACT GAAG (SEQ ID NO: 14) |
| 7 | CCCAAGCTTGAATTCACCATGGGGGAGAAACCCGGGAC (SEQ ID NO: 15) |
| 8 | GGGGCGGCCGCCTAGCAGAGTTGATCATCATAG (SEQ ID NO: 16) |
| 9 | CCCAAGCTTGGTACCACCATGCCGGCCCGGCGGCTGCTG (SEQ ID NO: 17) |
| 10 | CCCGCGGCCGCGCTAGCGAGGGCGTCTGGAGTCACTGG (SEQ ID NO: 18) |
| 11 | CCCGCGGCCGCTGGCGGTTCGATCACCCAGCTGTCCCACTT GG (SEQ ID NO: 19) |
| 12 | GGGCCCCTAAGCATAATCTGGAACATCATATGGATACTCGA GGCACACGCTGAACACTGA AGG (SEQ ID NO: 20) |
| 13 | CCCGAATTCATGCCGGCCCGGCGGCTGCTG (SEQ ID NO: 21) |
| 14 | CCCCTCGAGGGGAGGGCGTCTGGAGTCACTGG (SEQ ID NO: 22) |
| 15 | CCCGAATTCTTCTGTCCCAAGGATGTCCTG (SEQ ID NO: 23) |
| 16 | GGGTAAAAAGCAGCCCATCTGGTATGTTATTGACC (SEQ ID NO: 24) |
| 17 | GGTCAATAACATACCAGATGGGCTGCTTTTTACCC (SEQ ID NO: 25) |
| 18 | CCCGATATCTATGGAGACGACGCCCTTGAA (SEQ ID NO: 26) |
| 19 | GGGGCGGCCGCTTACACAGCATTCAAGCGGA (SEQ ID NO: 27) |

Example 1: Detection of the Ligand-Dependent Interaction Between SSTR2 and ARRB2

G-protein coupled receptors (GPCRs) are integral membrane proteins that contain 7 transmembrane domains. Upon binding of the appropriate ligand GPCRs are activated, leading to the recruitment of cytoplasmic beta arrestin proteins. In order to determine whether the assay can detect the somatostatin-dependent interaction between the GPCR SSTR2 and ARRB2, the following combinations of plasmids were transfected (FIG. 2A; 250 ng of the Tyk2(C) fusion construct, 250 ng of the gp130 fusion construct and 50 ng of the luciferase reporter construct) according to the methods described above:
a) pMet7-HA-Tyk2(C)+pMG2-ARRB2+pXP2d2-rPAPI-luciferase
b) pMet7-SSTR2-Tyk2(C)–HA+pMG2-SVT+pXP2d2-rPAPI-luciferase
c) pMet7-SSTR2-Tyk2(C)–HA+pMG2-ARRB2+pXP2d2-rPAPI-luciferase Transfected cells were either left untreated (NS) or treated with increasing doses (0.1-1-10 µM) of the SSTR2 agonist somatostatin. The fold induction for each sample was calculated as the ratio of the measured luciferase activity relative to the luciferase activity for the untreated sample of the same transfection. The results (FIG. 2B) show a clear ligand dose-dependent signal specifically in the cells co-transfected with both the SSTR2-Tyk2(C) and gp130-ARRB2 fusion constructs (transfection c). No signal was observed when either of the fusion constructs was transfected in combination with a negative control fusion construct (gp130-ARRB2 fusion construct combined with an unfused Tyk2(C) construct in transfection a, or SSTR2-Tyk2(C) fusion construct together with a fusion of gp130 to a fragment of the SV40 large T protein in b).

The assay was further optimized by transferring the Tyk2(C) fusion construct into another vector system (pSVSport) and testing the resulting constructs in a similar experiment as described above. The following combinations of plasmids were transfected (500 ng of the Tyk2(C) fusion construct, 250 ng of the gp130 fusion construct and 50 ng of the luciferase reporter construct) according to the methods described above:
a) pSVSport-HA-Tyk2(C)+pMG2-ARRB2+pXP2d2-rPAPI-luciferase
b) pSVSport-SSTR2-Tyk2(C)–HA+pMG2-SVT+pXP2d2-rPAPI-luciferase
c) pSVSport-SSTR2-Tyk2(C)–HA+pMG2-ARRB2+pXP2d2-rPAPI-luciferase Transfected cells were either left untreated (NS) or treated with increasing doses (0.1-1-10 µM) of the SSTR2 agonist somatostatin, and signals were calculated as indicated above. The resulting graph (FIG. 2C) shows strong and specific ligand dose-dependent signals up to 30-fold stronger compared to untreated samples.

Figure 2A:
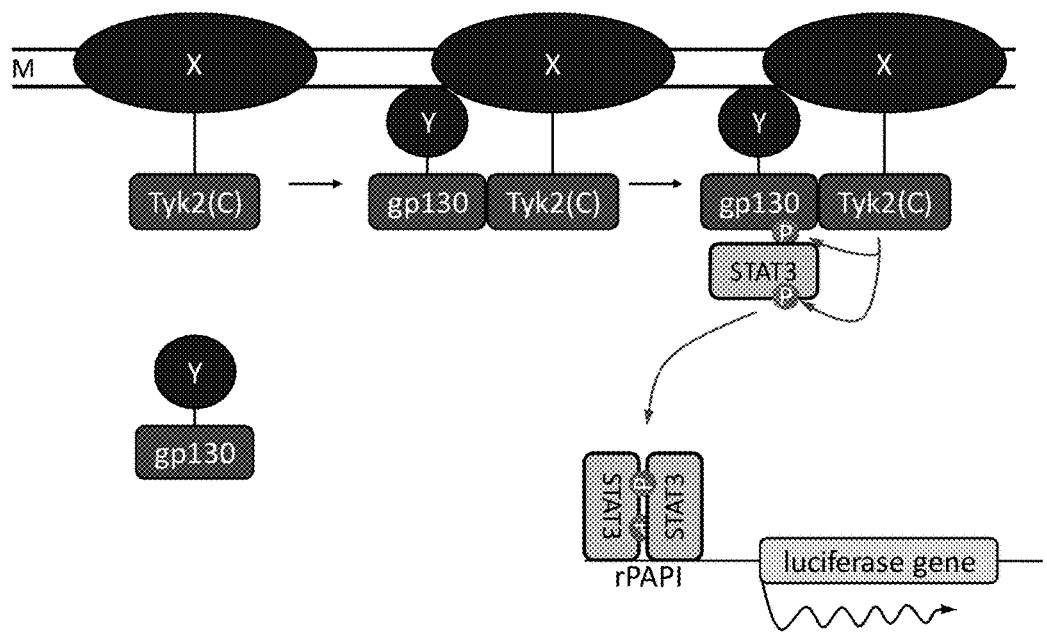
Figure 2B:
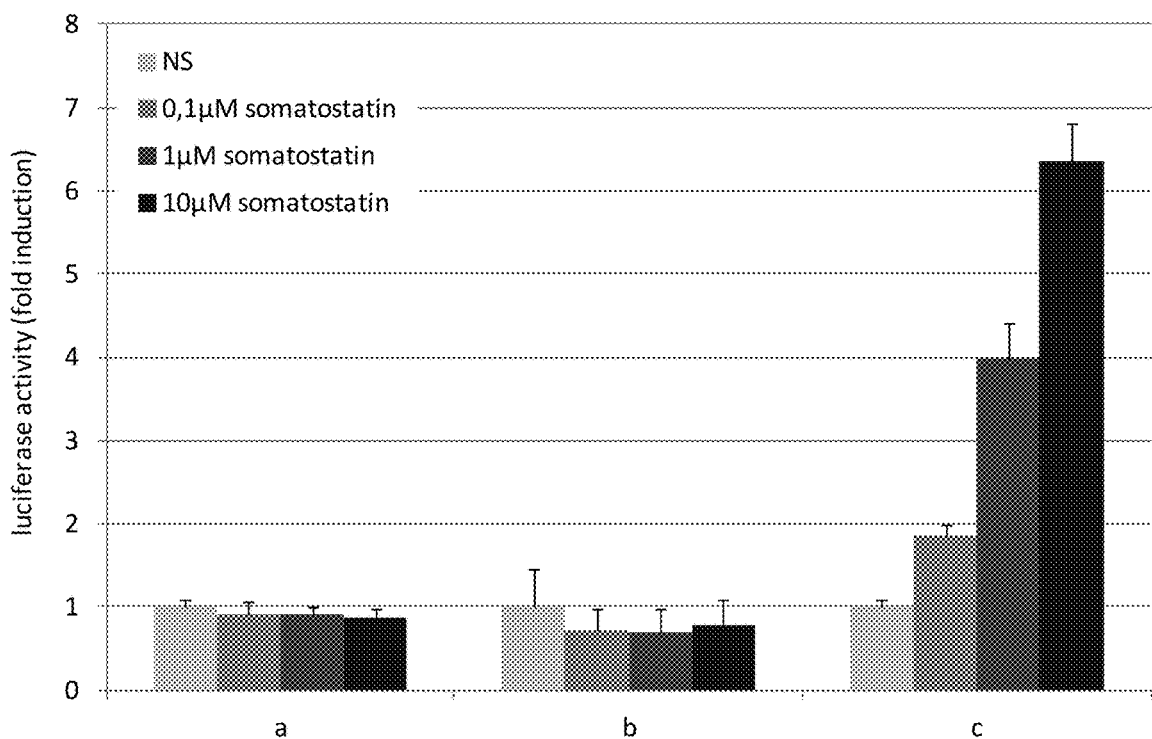
Figure 2C:
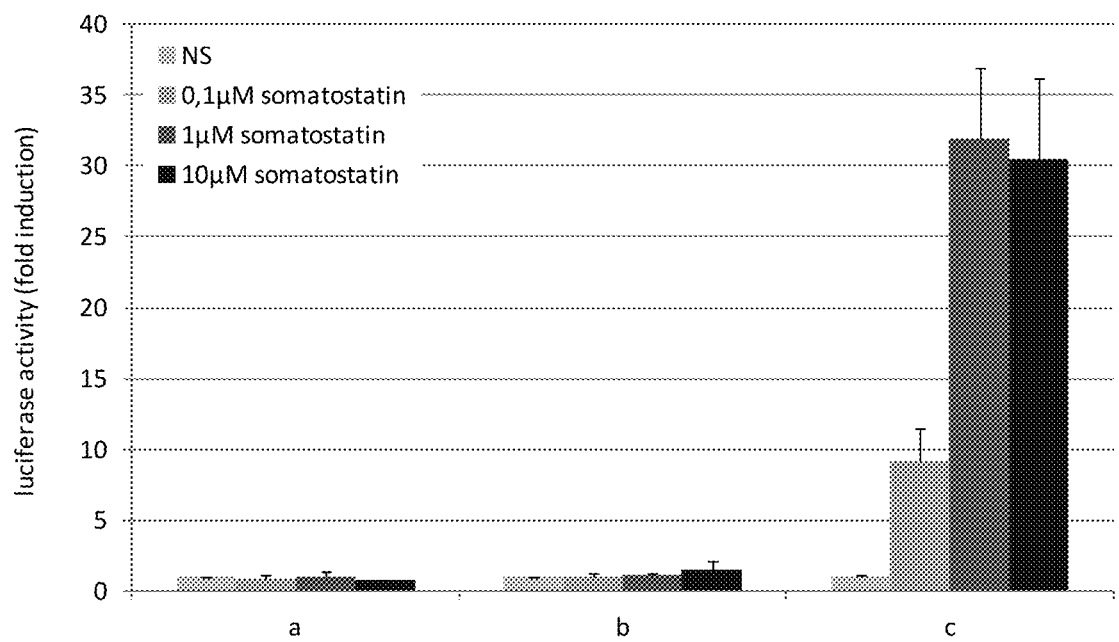
Figure 2D:
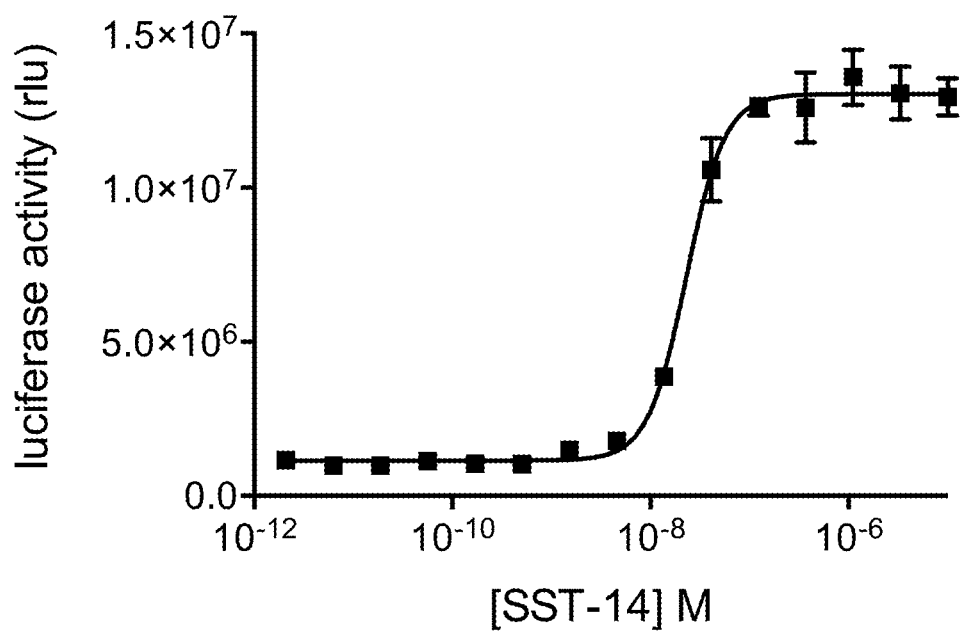

In another experiment, cells were transfected with 31 ng of the pMet7-SSTR2-Tyk2(C)–HA plasmid, 250 ng of the pMG2-ARRB2 plasmid and 50 ng of the pXP2d2-rPAPI-luciferase plasmid, and transfected cells were treated with a concentration gradient of somatostatin (a ⅓ serial dilution series down from 10 µM). The resulting dose-response curve is shown in FIG. 2D.

Together, these data illustrate that the method is able to detect ARRB2 recruitment to the SSTR2 integral membrane GPCR induced by treatment with the SSTR2 agonist somatostatin.

Example 2: Detection of the Ligand-Dependent Interaction Between AGTR1 and ARRB2

Likewise as in example 1, the ligand-induced recruitment of ARRB2 to another GPCR family member, AGTR1, was tested by transfecting the following combinations of plasmids (250 ng of the Tyk2(C) fusion construct, 250 ng of the gp130 fusion construct and 50 ng of the luciferase reporter construct) according to the methods described above:
a) pMet7-HA-Tyk2(C)+pMG2-ARRB2+pXP2d2-rPAPI-luciferase
b) pMet7-AGTR1-Tyk2(C)–HA+pMG2-SVT+pXP2d2-rPAPI-luciferase
c) pMet7-AGTR1-Tyk2(C)–HA+pMG2-ARRB2+pXP2d2-rPAPI-luciferase Transfected cells were either left untreated (NS) or treated with increasing doses (0.1-1-10 µM) of angiotensin II, an AGTR1 agonist. The fold induction for each sample was calculated as the ratio of the measured luciferase activity relative to the luciferase activity for the untreated sample of the same transfection. The results (FIG. 3A) show a clear ligand dose-dependent signal specifically in the cells cotransfected with both the AGTR1-Tyk2(C) and gp130-ARRB2 fusion constructs (transfection c). No signal was observed when either of the fusion constructs was transfected in combination with a negative control fusion construct (gp130-ARRB2 fusion construct combined with an unfused Tyk2(C) construct in transfection a, or AGTR1-Tyk2(C) fusion construct together with a fusion of gp130 to a fragment of the SV40 large T protein in b).

Figure 3B:
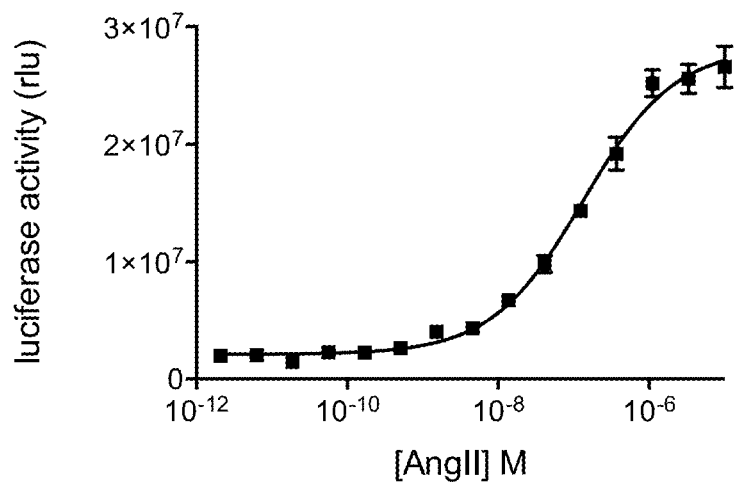

In another experiment, cells were transfected with 62 ng of the pMet7-AGTR1-Tyk2(C)–HA plasmid, 250 ng of the pMG2-ARRB2 plasmid and 50 ng of the pXP2d2-rPAPI-luciferase plasmid, and transfected cells were treated with a concentration gradient of angiotensin II (a ⅓ serial dilution series down from 10 µM). The resulting dose-response curve is shown in FIG. 3B.

These results confirm the method's ability to detect the interaction between the AGTR1 integral membrane protein and ARRB2, in a ligand-dependent manner.

Example 3: Effect of GPCR Antagonists on the Detection of the Interaction Between GPCRs and ARRB2

In order to test whether the assay allows evaluating the effect of GPCR antagonists, GPCR ligands were combined with specific antagonists of SSTR2 and AGTR1 in the assay for detection of their interaction with ARRB2. A peptide antagonist that specifically inhibits SSTR2 activation was tested (CYN154806), together with two small molecule AGTR1-selective antagonists (losartan and telmisartan).

Cells were transfected with the following combinations of plasmids (250 ng of the Tyk2(C) fusion construct, 250 ng of the gp130 fusion construct and 50 ng of the luciferase reporter construct) according to the methods described above:
 a) pMet7-SSTR2-Tyk2(C)–HA+pMG1-EFHA1+pXP2d2-rPAPI-luciferase
 b) pMet7-SSTR2-Tyk2(C)–HA+pMG2-ARRB2+pXP2d2-rPAPI-luciferase
 c) pMet7-AGTR1-Tyk2(C)–HA+pMG1-EFHA1+pXP2d2-rPAPI-luciferase
 d) pMet7-AGTR1-Tyk2(C)–HA+pMG2-ARRB2+pXP2d2-rPAPI-luciferase One day after transfection, cells were treated with combinations of GPCR ligand and antagonist (ligand: 1 µM somatostatin for transfections a and b, 10 µM angiotensin II for transfections c and d; antagonists: 0.05 or 0.5 µM CYN154806; 0.1 or 1 µM losartan or telmisartan), and luciferase was measured one day after treatment. The results are shown in FIG. 4 and clearly indicate the specific inhibition by the corresponding antagonist of the GPCR-ARRB2 interactions. The interaction between SSTR2 and ARRB2 (transfection b) can be specifically inhibited by the SSTR2-selective antagonist CYN154806, whereas the AGTR1-specific antagonists losartan and telmisartan have no effect. Conversely, AGTR1-ARRB2 interaction as detected by the assay (transfection d) can be selectively inhibited by the AGTR1-specific antagonists losartan and telmisartan, whereas the SSTR2-selective antagonist CYN154806 has no effect. In both cases, the inhibition through application of the antagonists goes down to background levels observed for cells that had not been treated with GPCR ligand (NS). The inhibitory effect is specific for the GPCR-ARRB2 interaction, as the signal obtained for control interactions of the GPCR-Tyk2(C) fusion construct with a positive control gp130 fusion construct containing EFHA1 (which binds to Tyk2(C) itself), are not affected by the GPCR antagonists.

In a second experiment (shown in FIG. 5), a dose-response curve was generated for the different GPCR antagonists. Cells were transfected with 125 ng of the pMet7-SSTR2-Tyk2(C)–HA or pMet7-AGTR1-Tyk2(C)–HA fusion construct, 250 ng of the pMG2-ARRB2 gp130 fusion construct and 50 ng of the pXP2d2-rPAPI-luciferase reporter plasmid, according to the methods described above. Cells were either left untreated, treated with 10 µM of the appropriate ligand (somatostatin in the case of SSTR2 and angiotensin II in the case of AGTR1) or treated with a combination of the cognate ligand and increasing doses ($10^{-13}$M up to $10^{-6}$M) of either GPCR antagonist (CYN154806, losartan, telmisartan). The results are presented in FIG. 5A (for the interaction between SSTR2 and ARRB2) and FIG. 5B (for the interaction between AGTR1 and ARRB2). Again, these data clearly indicate the specific inhibition by the corresponding antagonist of the GPCR-ARRB2 interactions. The interaction between SSTR2 and ARRB2 can be specifically and completely inhibited by the SSTR2-selective antagonist CYN154806, whereas the AGTR1-specific antagonists losartan and telmisartan have no effect. Conversely, AGTR1-ARRB2 interaction as detected by the assay can be selectively and completely inhibited by the AGTR1-specific antagonists losartan and telmisartan, whereas the SSTR2-selective antagonist CYN154806 has no effect. It is of note that the observed stronger effect of telmisartan compared to losartan in this assay corresponds with the reported higher binding affinity of telmisartan versus losartan towards AGTR1 (Kakuta et al., 2005).

Together, these results confirm the specificity of the GPCR-ARRB2 interactions as detected by the assay and indicate that the assay can be applied to identify inhibitors of these interactions.

Example 4: Detection of Context-Dependent Dimerization of a Transmembrane Protein To support the ability of the method to detect protein-protein interactions under physiological conditions, we studied dimerization of ERN1. ERN1 is a single-span transmembrane protein involved in the cellular response to ER-stress. The ERN1 protein is able to sense unfolded proteins in the ER through its N-terminal domain which is exposed to the ER lumen. This leads to its dimerization and activation of the kinase and endoribonuclease enzymatic domains in its C-terminal moiety exposed towards the cytoplasm. To mimic ER-stress, tunicamycin was applied to the cells, an inhibitor of protein glycosylation which is generally used to induce ER-stress.

Figure 6A:
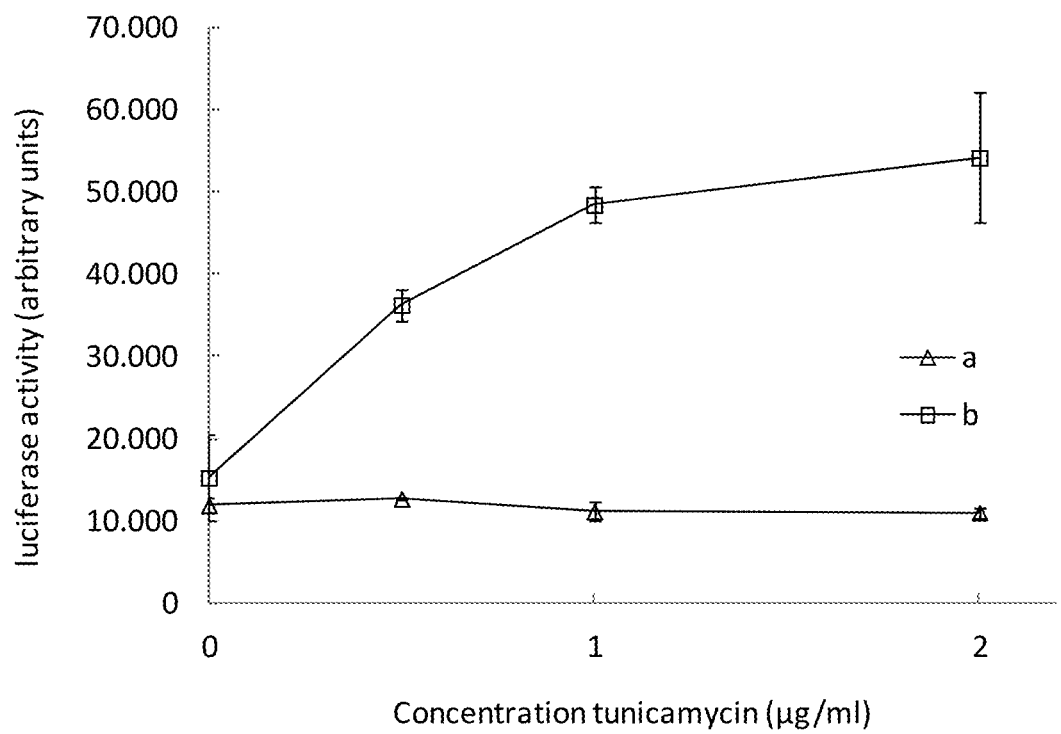
Figure 6B:
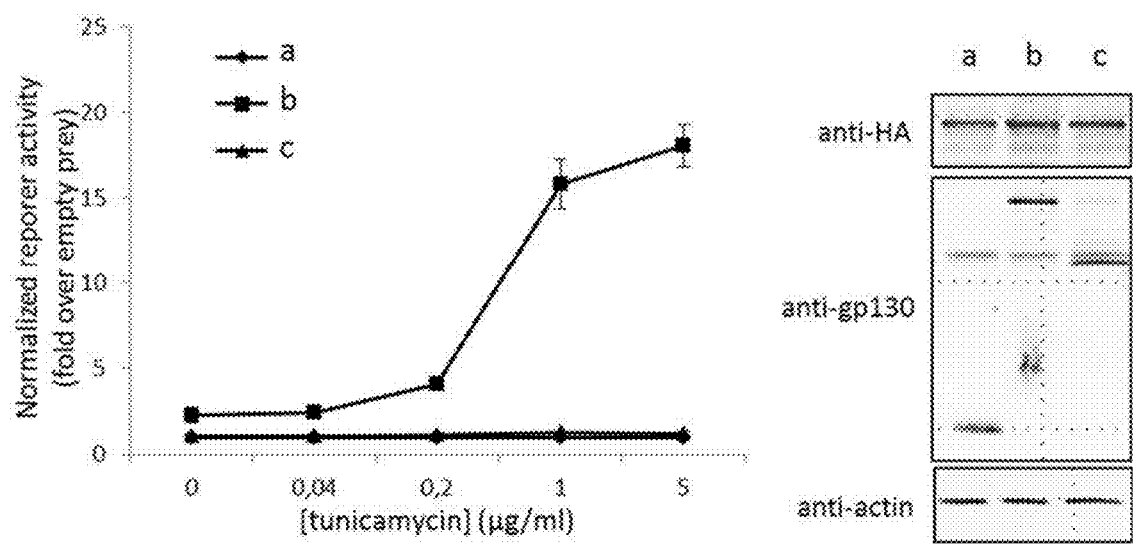
Figure 6C:
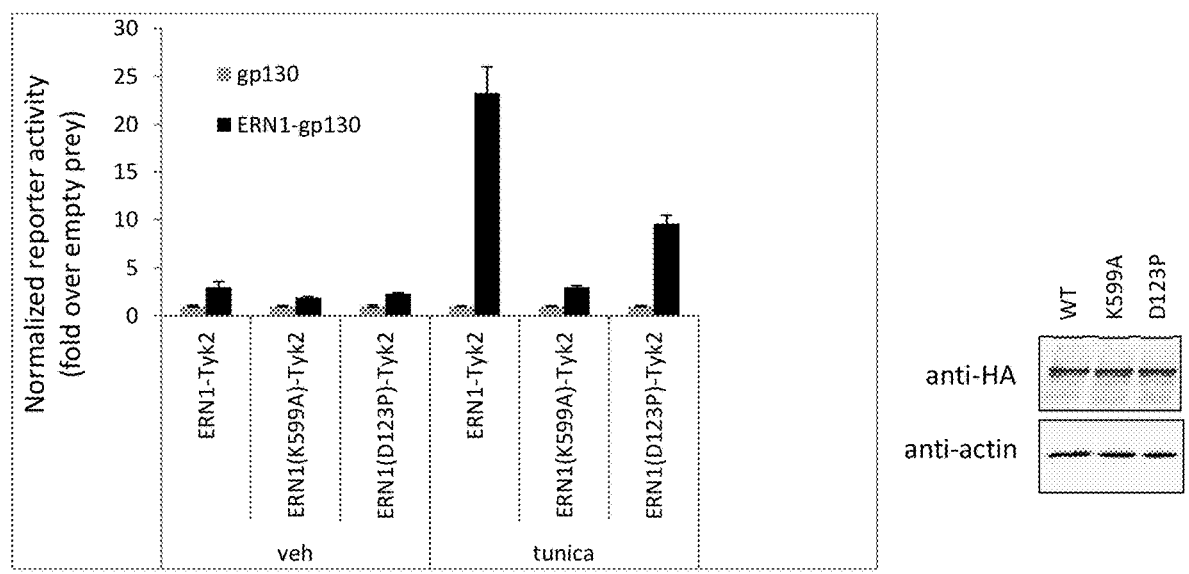
Figure 6D:
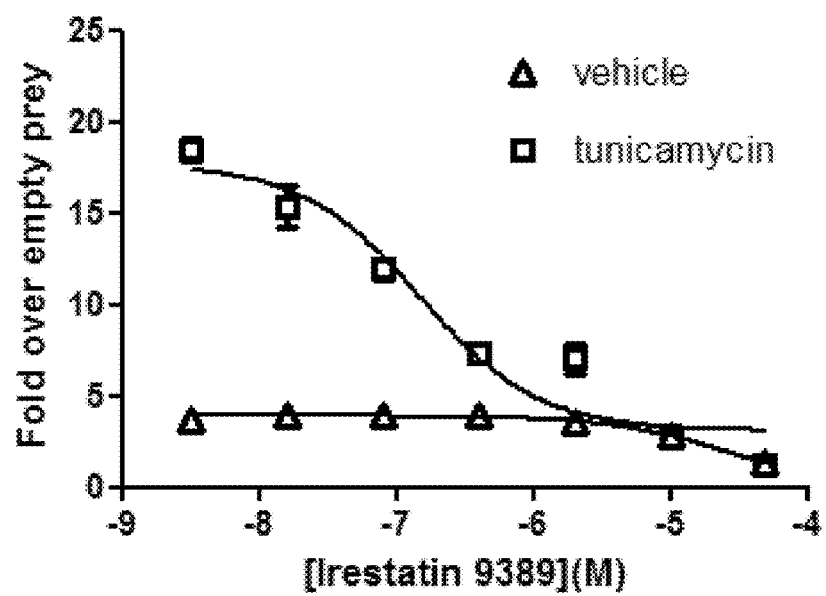

In a first experiment, cells were transfected with the following combinations of plasmids (500 ng of the kinase fusion construct, 100 ng of the gp130 fusion construct and 50 ng of the luciferase reporter construct) according to the methods described above:
 a) pcDNA5/FRT/TO-ERN1-Tyk2(C)–HA+pMG1+pXP2d2-rPAPI-luciferase
 b) pcDNA5/FRT/TO-ERN1-Tyk2(C)–HA+pMG2C-ERN1 pXP2d2-rPAPI-luciferase After transfection, cells were treated with 0-0.5-1-2 µg/ml tunicamycin, final concentration. The results shown in FIG. 6A show a dose-dependent signal upon addition of tunicamycin, only in cells expressing both ERN1-Tyk2(C) and ERN1-gp130 fusion constructs (transfection b). No signal was observed when the ERN1-Tyk2(C) fusion construct was combined with an unfused gp130 fragment (transfection a).

In a second experiment (FIG. 6B), cells were transfected with the following combinations of plasmids (62.5 ng of the kinase fusion construct, 125 ng of the gp130 fusion construct and 50 ng of the luciferase reporter construct) according to the methods described herein:
 a) pcDNA5/FRT/TO-ERN1-Tyk2(C)-HA+pMG1+ pXP2d2-rPAPI-luciferase
 b) pcDNA5/FRT/TO-ERN1-Tyk2(C)-HA+pMG2C-ERN1 pXP2d2-rPAPI-luciferase
 c) pcDNA5/FRT/TO-ERN1-Tyk2(C)-HA pMG2C-ERN1cyt+pXP2d2-rPAPI-luciferase After transfection, cells were treated with 0-0.04-0.2-1-5 μg/ml tunicamycin, final concentration. The luciferase data are presented as fold induction relative to the signal obtained in cells transfected with unfused gp130 (empty prey; transfection a) and treated with the same concentration tunicamycin. Expression of the different fusion proteins was confirmed using Western blot. These data show that in accordance with the requirement of the ERN1 lumenal domain to sense ER stress, no signal is produced upon overexpression of full length ERN1 kinase fusion and a gp130 fusion containing only the cytoplasmic portion of ERN1 (transfection c).

In a next experiment (FIG. 6C), cells were transfected with combinations of the pXP2d2-rPAPI-luciferase construct (50 ng), a WT or mutant ERN1 kinase fusion construct (62.5 ng) and either unfused or ERN1-fused gp130 construct (125 ng). After transfection, cells were either vehicle (DMSO) treated or treated with 1 μg/ml tunicamycin (final concentration). The mutant ERN1 kinase fusions have mutations in either the luminal domain (D123P) or cytoplasmic ATP-binding pocket (K599A). Both mutations are expected to block ERN1 oligomerization. As evident from FIG. 6C we indeed find that both mutations block the interaction with full length ERN1 gp130 fusion, despite equal expression and similar (aspecific) interaction signals with unfused gp130 constructs.

In another experiment (FIG. 6D), cells were transfected with combinations of the pXP2d2-rPAPI-luciferase construct (50 ng), the ERN1 kinase fusion construct (62.5 ng) and either unfused or ERN1-fused gp130 construct (125 ng). After transfection, cells were treated with tunicamycin (1 μg/ml tunicamycin final concentration) or vehicle (DMSO) combined with increasing doses of Irestatin 9389. This molecule was recently reported to inhibit ERN1 endonuclease activity (Feldman and Koong, 2007). Although the molecular mode of action of Irestatin 9389 was not reported, the molecule induced a dose-dependent disruption of ERN1 dimerization in the assay described herein.

Together, these data indicate that the method is able to specifically detect the ER-stress-induced dimerization of the ERN1 protein and to analyze the structure-function relationship of this protein and pharmacological interference with dimerization of the protein in more detail.

Example 5: Detection of Heterologous Interactions Among Transmembrane Proteins

To further corroborate the ability of the assay to analyze protein-protein interactions involving integral membrane proteins, heterologous interactions between transmembrane proteins were analyzed. Serotonin transporter (SERT) is a multispan integral membrane protein that transports serotonin from the synaptic spaces into presynaptic neurons, this way terminating the action of serotonin and recycling it. In this example, we show its interaction with the synaptobrevins VAMP1 and VAMP2, which are transmembrane proteins involved in fusion of synaptic vesicles with the presynaptic membrane.

Cells were transfected with combinations of the pXP2d2-rPAPI-luciferase construct (50 ng), a SERT or RTp66 kinase fusion construct (1000 ng) and either unfused (pMG2) or one of the indicated gp130 fusion constructs (pMG2-RTp51, pMG1-VAMP1 or pMG2-VAMP2; 500 ng). Luciferase activity is shown as fold induction relative to the luciferase signal obtained in cells transfected with unfused gp130 (pMG2).

The results (FIG. 7) show a clear signal when VAMP1 and VAMP2 gp130 fusion constructs were transfected in combination with the SERT kinase fusion construct, and not when combined with the HIV-1 RTp66 (reverse transcriptase subunit p66) fusion construct. The strong signal obtained for the co-transfection of the RTp66 kinase and the RTp51 gp130 fusion constructs, which has been previously described (WO2012117031), is included as a control for proper expression and functioning of the RTp66 kinase fusion.

REFERENCES

Eyckerman, S., Verhee, A., Van der Heyden, J., Lemmens, I., Van Ostade, X., Vandekerckhove, J., and Tavernier, J. (2001). Design and application of a cytokine-receptor-based interaction trap. Nature Cell Biology 3, 1114-1119.

Feldman, D., and Koong, A. (2007). Irestatin, a potent inhibitor of ERN1α and the unfolded protein response, is a hypoxia-selective cytotoxin and impairs tumor growth. J Clin Oncol 25, 3514.

Kakuta, H., Sudoh, K., Sasamata, M., and Yamagishi, S. (2005). Telmisartan has the strongest binding affinity to angiotensin II type 1 receptor: comparison with other angiotensin II type 1 receptor blockers. Int J Clin Pharmacol Res 25, 41-46.

Lamesch, P., Li, N., Milstein, S., Fan, C., Hao, T., Szabo, G., Hu, Z., Venkatesan, K., Bethel, G., Martin, P., et al., (2007). hORFeome v3.1: a resource of human open reading frames representing over 10,000 human genes. Genomics 89, 307-315.

Lemmens, I., Eyckerman, S., Zabeau, L., Catteeuw, D., Vertenten, E., Verschueren, K., Huylebroeck, D., Vandekerckhove, J., and Tavernier, J. (2003). Heteromeric MAPPIT: a novel strategy to study modification-dependent protein-protein interactions in mammalian cells. Nucleic Acids Research 31.

Lievens, S., Vanderroost, N., Van der Heyden, J., Gesellchen, V., Vidal, M., and Tavernier, J. (2009). Array MAPPIT: high-throughput interactome analysis in mammalian cells. J Proteome Res 8, 877-886.

Pattyn, E., Lavens, D., Van der Heyden, J., verhee, A., Lievens, S., Lemmens, I., Hallenberger, S., Jochmans, D and Tavernier, J. (2008). MAPPIT (Mammalian Protein-Protein Interaction Trap) as a tool to study HIV reverse transcriptase dimerization in intact human cells. J. Virol. Methods 153, 7-15.

Takebe, Y., Seiki, M., Fujisawa, J., Hoy, P., Yokota, K., Arai, K., Yoshida, M., and Arai, N. (1988). SR alpha promoter: an efficient and versatile mammalian cDNA expression system composed of the simian virus 40 early promoter and the R-U5 segment of human T-cell leukemia virus type 1 long terminal repeat. Mol Cell Biol 8, 466-472.

What is claimed is:

1. A method for detecting a compound-protein interaction, the method comprising:
   (a) contacting a eukaryotic cell with a compound, the eukaryotic cell comprising a recombinant protein complex comprising:
      (i) a first fusion protein comprising a membrane spanning domain fused to a Tky2 tyrosine kinase domain and
      (ii) a second fusion protein comprising an interaction domain fused to a gp130 reporter phosphorylation domain,
      wherein the compound mediates the formation of the recombinant protein complex, and
      wherein the tyrosine kinase domain phosphorylates a tyrosine of the reporter phosphorylation domain upon the formation of the recombinant protein complex, and
   (b) measuring the phosphorylation of the reporter phosphorylation domain.

2. The method according to claim 1, wherein the tyrosine kinase domain is a mutant tyrosine kinase domain.

3. The method according to claim 2, wherein the mutant tyrosine kinase domain is a constitutively active mutant kinase.

4. The method according to claim 2, wherein the mutant tyrosine kinase domain is an inactive mutant that is activated by addition of an exogenous small molecule.

5. The method according to claim 1, wherein the tyrosine kinase domain is fused to the carboxyterminal end of the membrane spanning domain in the first fusion protein.

6. The method according to claim 1, wherein the membrane spanning domain is a multispan membrane span protein.

7. The method according to claim 6, wherein the multispan membrane span protein is a G protein coupled receptor.

8. The method according to claim 1, wherein the compound is a small molecule.

9. The method according to claim 1, wherein measuring the phosphorylation of the reporter phosphorylation domain is measured indirectly by detection of a reporter gene that is activated by phosphorylation of the reporter phosphorylation domain.

10. The method according to claim 9 wherein the reporter gene is a luciferase gene.

11. The method according to claim 1, wherein phosphorylation of the reporter phosphorylation domain is measured directly.

* * * * *

SEQUENCE LISTING

<160> NUMBER OF SEQ ID NOS: 37

<210> SEQ ID NO 1
<211> LENGTH: 1187
<212> TYPE: PRT
<213> ORGANISM: Homo sapiens

<400> SEQUENCE: 1

Met Pro Leu Arg His Trp Gly Met Ala Arg Gly Ser Lys Pro Val Gly
1               5                   10                  15

Asp Gly Ala Gln Pro Met Ala Ala Met Gly Gly Leu Lys Val Leu Leu
            20                  25                  30

His Trp Ala Gly Pro Gly Gly Gly Glu Pro Trp Val Thr Phe Ser Glu
        35                  40                  45

Ser Ser Leu Thr Ala Glu Glu Val Cys Ile His Ile Ala His Lys Val
    50                  55                  60

Gly Ile Thr Pro Pro Cys Phe Asn Leu Phe Ala Leu Phe Asp Ala Gln
65                  70                  75                  80

Ala Gln Val Trp Leu Pro Pro Asn His Ile Leu Glu Ile Pro Arg Asp
                85                  90                  95

Ala Ser Leu Met Leu Tyr Phe Arg Ile Arg Phe Tyr Phe Arg Asn Trp
            100                 105                 110

His Gly Met Asn Pro Arg Glu Pro Ala Val Tyr Arg Cys Gly Pro Pro
        115                 120                 125

Gly Thr Glu Ala Ser Ser Asp Gln Thr Ala Gln Gly Met Gln Leu Leu
    130                 135                 140

Asp Pro Ala Ser Phe Glu Tyr Leu Phe Glu Gln Gly Lys His Glu Phe
145                 150                 155                 160

Val Asn Asp Val Ala Ser Leu Trp Glu Leu Ser Thr Glu Glu Glu Ile
                165                 170                 175

His His Phe Lys Asn Glu Ser Leu Gly Met Ala Phe Leu His Leu Cys
            180                 185                 190

His Leu Ala Leu Arg His Gly Ile Pro Leu Glu Glu Val Ala Lys Lys
        195                 200                 205

Thr Ser Phe Lys Asp Cys Ile Pro Arg Ser Phe Arg Arg His Ile Arg
    210                 215                 220

Gln His Ser Ala Leu Thr Arg Leu Arg Leu Arg Asn Val Phe Arg Arg
225                 230                 235                 240

Phe Leu Arg Asp Phe Gln Pro Gly Arg Leu Ser Gln Gln Met Val Met
                245                 250                 255

Val Lys Tyr Leu Ala Thr Leu Glu Arg Leu Ala Pro Arg Phe Gly Thr
            260                 265                 270

Glu Arg Val Pro Val Cys His Leu Arg Leu Leu Ala Gln Ala Glu Gly
        275                 280                 285

Glu Pro Cys Tyr Ile Arg Asp Ser Gly Val Ala Pro Thr Asp Pro Gly
    290                 295                 300

Pro Glu Ser Ala Ala Gly Pro Pro Thr His Glu Val Leu Val Thr Gly
305                 310                 315                 320

Thr Gly Gly Ile Gln Trp Trp Pro Val Glu Glu Val Asn Lys Glu
                325                 330                 335

Glu Gly Ser Ser Gly Ser Ser Gly Arg Asn Pro Gln Ala Ser Leu Phe
            340                 345                 350

Gly Lys Lys Ala Lys Ala His Lys Ala Val Gly Gln Pro Ala Asp Arg
        355                 360                 365

```
Pro Arg Glu Pro Leu Trp Ala Tyr Phe Cys Asp Phe Arg Asp Ile Thr
    370                 375                 380
His Val Val Leu Lys Glu His Cys Val Ser Ile His Arg Gln Asp Asn
385                 390                 395                 400
Lys Cys Leu Glu Leu Ser Leu Pro Ser Arg Ala Ala Ala Leu Ser Phe
                405                 410                 415
Val Ser Leu Val Asp Gly Tyr Phe Arg Leu Thr Ala Asp Ser Ser His
                420                 425                 430
Tyr Leu Cys His Glu Val Ala Pro Pro Arg Leu Val Met Ser Ile Arg
            435                 440                 445
Asp Gly Ile His Gly Pro Leu Leu Glu Pro Phe Val Gln Ala Lys Leu
    450                 455                 460
Arg Pro Glu Asp Gly Leu Tyr Leu Ile His Trp Ser Thr Ser His Pro
465                 470                 475                 480
Tyr Arg Leu Ile Leu Thr Val Ala Gln Arg Ser Gln Ala Pro Asp Gly
                485                 490                 495
Met Gln Ser Leu Arg Leu Arg Lys Phe Pro Ile Glu Gln Asp Gly
                500                 505                 510
Ala Phe Val Leu Glu Gly Trp Gly Arg Ser Phe Pro Ser Val Arg Glu
            515                 520                 525
Leu Gly Ala Ala Leu Gln Gly Cys Leu Leu Arg Ala Gly Asp Asp Cys
    530                 535                 540
Phe Ser Leu Arg Arg Cys Cys Leu Pro Gln Pro Gly Glu Thr Ser Asn
545                 550                 555                 560
Leu Ile Ile Met Arg Gly Ala Arg Ala Ser Pro Arg Thr Leu Asn Leu
                565                 570                 575
Ser Gln Leu Ser Phe His Arg Val Asp Gln Lys Glu Ile Thr Gln Leu
                580                 585                 590
Ser His Leu Gly Gln Gly Thr Arg Thr Asn Val Tyr Glu Gly Arg Leu
            595                 600                 605
Arg Val Glu Gly Ser Gly Asp Pro Glu Glu Gly Lys Met Asp Asp Glu
    610                 615                 620
Asp Pro Leu Val Pro Gly Arg Asp Arg Gly Gln Glu Leu Arg Val Val
625                 630                 635                 640
Leu Lys Val Leu Asp Pro Ser His His Asp Ile Ala Leu Ala Phe Tyr
                645                 650                 655
Glu Thr Ala Ser Leu Met Ser Gln Val Ser His Thr His Leu Ala Phe
                660                 665                 670
Val His Gly Val Cys Val Arg Gly Pro Glu Asn Ile Met Val Thr Glu
            675                 680                 685
Tyr Val Glu His Gly Pro Leu Asp Val Trp Leu Arg Arg Glu Arg Gly
    690                 695                 700
His Val Pro Met Ala Trp Lys Met Val Val Ala Gln Gln Leu Ala Ser
705                 710                 715                 720
Ala Leu Ser Tyr Leu Glu Asn Lys Asn Leu Val His Gly Asn Val Cys
                725                 730                 735
Gly Arg Asn Ile Leu Leu Ala Arg Leu Gly Leu Ala Glu Gly Thr Ser
                740                 745                 750
Pro Phe Ile Lys Leu Ser Asp Pro Gly Val Gly Leu Gly Ala Leu Ser
            755                 760                 765
Arg Glu Glu Arg Val Glu Arg Ile Pro Trp Leu Ala Pro Glu Cys Leu
    770                 775                 780
Pro Gly Gly Ala Asn Ser Leu Ser Thr Ala Met Asp Lys Trp Gly Phe
```

```
                785                 790                 795                 800
Gly Ala Thr Leu Leu Glu Ile Cys Phe Asp Gly Glu Ala Pro Leu Gln
                    805                 810                 815
Ser Arg Ser Pro Ser Glu Lys Glu His Phe Tyr Gln Arg Gln His Arg
                    820                 825                 830
Leu Pro Glu Pro Ser Cys Pro Gln Leu Ala Thr Leu Thr Ser Gln Cys
                    835                 840                 845
Leu Thr Tyr Glu Pro Thr Gln Arg Pro Ser Phe Arg Thr Ile Leu Arg
                    850                 855                 860
Asp Leu Thr Arg Leu Gln Pro His Asn Leu Ala Asp Val Leu Thr Val
865                 870                 875                 880
Asn Pro Asp Ser Pro Ala Ser Asp Pro Thr Val Phe His Lys Arg Tyr
                    885                 890                 895
Leu Lys Lys Ile Arg Asp Leu Gly Glu Gly His Phe Gly Lys Val Ser
                    900                 905                 910
Leu Tyr Cys Tyr Asp Pro Thr Asn Asp Gly Thr Gly Glu Met Val Ala
                    915                 920                 925
Val Lys Ala Leu Lys Ala Asp Cys Gly Pro Gln His Arg Ser Gly Trp
930                 935                 940
Lys Gln Glu Ile Asp Ile Leu Arg Thr Leu Tyr His Glu His Ile Ile
945                 950                 955                 960
Lys Tyr Lys Gly Cys Cys Glu Asp Gln Gly Glu Lys Ser Leu Gln Leu
                    965                 970                 975
Val Met Glu Tyr Val Pro Leu Gly Ser Leu Arg Asp Tyr Leu Pro Arg
                    980                 985                 990
His Ser Ile Gly Leu Ala Gln Leu  Leu Leu Phe Ala Gln  Gln Ile Cys
        995                1000                1005
Glu Gly Met Ala Tyr Leu His  Ala Gln His Tyr Ile  His Arg Asp
        1010                1015                1020
Leu Ala Ala Arg Asn Val Leu  Leu Asp Asn Asp Arg  Leu Val Lys
        1025                1030                1035
Ile Gly Asp Phe Gly Leu Ala  Lys Ala Val Pro Glu  Gly His Glu
        1040                1045                1050
Tyr Tyr Arg Val Arg Glu Asp  Gly Asp Ser Pro Val  Phe Trp Tyr
        1055                1060                1065
Ala Pro Glu Cys Leu Lys Glu  Tyr Lys Phe Tyr Tyr  Ala Ser Asp
        1070                1075                1080
Val Trp Ser Phe Gly Val Thr  Leu Tyr Glu Leu Leu  Thr His Cys
        1085                1090                1095
Asp Ser Ser Gln Ser Pro Pro  Thr Lys Phe Leu Glu  Leu Ile Gly
        1100                1105                1110
Ile Ala Gln Gly Gln Met Thr  Val Leu Arg Leu Thr  Glu Leu Leu
        1115                1120                1125
Glu Arg Gly Glu Arg Leu Pro  Arg Pro Asp Lys Cys  Pro Cys Glu
        1130                1135                1140
Val Tyr His Leu Met Lys Asn  Cys Trp Glu Thr Glu  Ala Ser Phe
        1145                1150                1155
Arg Pro Thr Phe Glu Asn Leu  Ile Pro Ile Leu Lys  Thr Val His
        1160                1165                1170
Glu Lys Tyr Gln Gly Gln Ala  Pro Ser Val Phe Ser  Val Cys
        1175                1180                1185

<210> SEQ ID NO 2
```

```
<211> LENGTH: 158
<212> TYPE: PRT
<213> ORGANISM: Homo sapiens

<400> SEQUENCE: 2

Thr Val Val His Ser Gly Tyr Arg His Gln Val Pro Ser Val Gln Val
1               5                   10                  15

Phe Ser Arg Ser Glu Ser Thr Gln Pro Leu Leu Asp Ser Glu Glu Arg
            20                  25                  30

Pro Glu Asp Leu Gln Leu Val Asp His Val Asp Gly Asp Gly Asp Ile
        35                  40                  45

Leu Pro Arg Gln Gln Tyr Phe Lys Gln Asn Cys Ser Gln His Glu Ser
50                  55                  60

Ser Pro Asp Ile Ser His Phe Glu Arg Ser Lys Gln Val Ser Val
65                  70                  75                  80

Asn Glu Glu Asp Phe Val Arg Leu Lys Gln Gln Ile Ser Asp His Ile
                85                  90                  95

Ser Gln Ser Cys Gly Ser Gly Gln Met Lys Met Phe Gln Glu Val Ser
            100                 105                 110

Ala Ala Asp Ala Phe Gly Pro Gly Thr Glu Gly Gln Val Glu Arg Phe
        115                 120                 125

Glu Thr Val Gly Met Glu Ala Ala Thr Asp Glu Gly Met Pro Lys Ser
130                 135                 140

Tyr Leu Pro Gln Thr Val Arg Gln Gly Gly Tyr Met Pro Gln
145                 150                 155

<210> SEQ ID NO 3
<211> LENGTH: 985
<212> TYPE: PRT
<213> ORGANISM: Artificial Sequence
<220> FEATURE:
<223> OTHER INFORMATION: SSTR2-Tyk2(C) fusion construct

<400> SEQUENCE: 3

Met Asp Met Ala Asp Glu Pro Leu Asn Gly Ser His Thr Trp Leu Ser
1               5                   10                  15

Ile Pro Phe Asp Leu Asn Gly Ser Val Val Ser Thr Asn Thr Ser Asn
            20                  25                  30

Gln Thr Glu Pro Tyr Tyr Asp Leu Thr Ser Asn Ala Val Leu Thr Phe
        35                  40                  45

Ile Tyr Phe Val Val Cys Ile Ile Gly Leu Cys Gly Asn Thr Leu Val
50                  55                  60

Ile Tyr Val Ile Leu Arg Tyr Ala Lys Met Lys Thr Ile Thr Asn Ile
65                  70                  75                  80

Tyr Ile Leu Asn Leu Ala Ile Ala Asp Glu Leu Phe Met Leu Gly Leu
                85                  90                  95

Pro Phe Leu Ala Met Gln Val Ala Leu Val His Trp Pro Phe Gly Lys
            100                 105                 110

Ala Ile Cys Arg Val Val Met Thr Val Asp Gly Ile Asn Gln Phe Thr
        115                 120                 125

Ser Ile Phe Cys Leu Thr Val Met Ser Ile Asp Arg Tyr Leu Ala Val
130                 135                 140

Val His Pro Ile Lys Ser Ala Lys Trp Arg Arg Pro Arg Thr Ala Lys
145                 150                 155                 160

Met Ile Thr Met Ala Val Trp Gly Val Ser Leu Leu Val Ile Leu Pro
                165                 170                 175
```

```
Ile Met Ile Tyr Ala Gly Leu Arg Ser Asn Gln Trp Gly Arg Ser Ser
            180                 185                 190

Cys Thr Ile Asn Trp Pro Gly Glu Ser Gly Ala Trp Tyr Thr Gly Phe
        195                 200                 205

Ile Ile Tyr Thr Phe Ile Leu Gly Phe Leu Val Pro Leu Thr Ile Ile
        210                 215                 220

Cys Leu Cys Tyr Leu Phe Ile Ile Lys Val Lys Ser Ser Gly Ile
225                 230                 235                 240

Arg Val Gly Ser Ser Lys Arg Lys Ser Glu Lys Lys Val Thr Arg
                245                 250                 255

Met Val Ser Ile Val Val Ala Val Phe Ile Phe Cys Trp Leu Pro Phe
        260                 265                 270

Tyr Ile Phe Asn Val Ser Ser Val Ser Met Ala Ile Ser Pro Thr Pro
        275                 280                 285

Ala Leu Lys Gly Met Phe Asp Phe Val Val Leu Thr Tyr Ala Asn
        290                 295                 300

Ser Cys Ala Asn Pro Ile Leu Tyr Ala Phe Leu Ser Asp Asn Phe Lys
305                 310                 315                 320

Lys Ser Phe Gln Asn Val Leu Cys Leu Val Lys Val Ser Gly Thr Asp
                325                 330                 335

Asp Gly Glu Arg Ser Asp Ser Lys Gln Asp Lys Ser Arg Leu Asn Glu
                340                 345                 350

Thr Thr Glu Thr Gln Arg Thr Leu Leu Asn Gly Asp Leu Gln Thr Ser
            355                 360                 365

Ile Ala Ala Ala Gly Gly Ser Ile Thr Gln Leu Ser His Leu Gly Gln
370                 375                 380

Gly Thr Arg Thr Asn Val Tyr Glu Gly Arg Leu Arg Val Glu Gly Ser
385                 390                 395                 400

Gly Asp Pro Glu Glu Gly Lys Met Asp Asp Glu Asp Pro Leu Val Pro
                405                 410                 415

Gly Arg Asp Arg Gly Gln Glu Leu Arg Val Val Leu Lys Val Leu Asp
                420                 425                 430

Pro Ser His His Asp Ile Ala Leu Ala Phe Tyr Glu Thr Ala Ser Leu
            435                 440                 445

Met Ser Gln Val Ser His Thr His Leu Ala Phe Val His Gly Val Cys
    450                 455                 460

Val Arg Gly Pro Glu Asn Ser Met Val Thr Glu Tyr Val Glu His Gly
465                 470                 475                 480

Pro Leu Asp Val Trp Leu Arg Arg Glu Arg Gly His Val Pro Met Ala
                485                 490                 495

Trp Lys Met Val Val Ala Gln Gln Leu Ala Ser Ala Leu Ser Tyr Leu
            500                 505                 510

Glu Asn Lys Asn Leu Val His Gly Asn Val Cys Gly Arg Asn Ile Leu
    515                 520                 525

Leu Ala Arg Leu Gly Leu Ala Glu Gly Thr Ser Pro Phe Ile Lys Leu
530                 535                 540

Ser Asp Pro Gly Val Gly Leu Gly Ala Leu Ser Arg Glu Glu Arg Val
545                 550                 555                 560

Glu Arg Ile Pro Trp Leu Ala Pro Glu Cys Leu Pro Gly Gly Ala Asn
                565                 570                 575

Ser Leu Ser Thr Ala Met Asp Lys Trp Gly Phe Gly Ala Thr Leu Leu
            580                 585                 590

Glu Ile Cys Phe Asp Gly Glu Ala Pro Leu Gln Ser Arg Ser Pro Ser
```

```
              595                 600                 605
Glu Lys Glu His Phe Tyr Gln Arg Gln His Arg Leu Pro Glu Pro Ser
    610                 615                 620

Cys Pro Gln Leu Ala Thr Leu Thr Ser Gln Cys Leu Thr Tyr Glu Pro
625                 630                 635                 640

Thr Gln Arg Pro Ser Phe Arg Thr Ile Leu Arg Asp Leu Thr Arg Val
                645                 650                 655

Gln Pro His Asn Leu Ala Asp Val Leu Thr Val Asn Arg Asp Ser Pro
            660                 665                 670

Ala Val Gly Pro Thr Thr Phe His Lys Arg Tyr Leu Lys Lys Ile Arg
        675                 680                 685

Asp Leu Gly Glu Gly His Phe Gly Lys Val Ser Leu Tyr Cys Tyr Asp
690                 695                 700

Pro Thr Asn Asp Gly Thr Gly Glu Met Val Ala Val Lys Ala Leu Lys
705                 710                 715                 720

Ala Asp Cys Gly Pro Gln His Arg Ser Gly Trp Lys Gln Glu Ile Asp
                725                 730                 735

Ile Leu Arg Thr Leu Tyr His Glu His Ile Ile Lys Tyr Lys Gly Cys
            740                 745                 750

Cys Glu Asp Gln Gly Glu Lys Ser Leu Gln Leu Val Met Glu Tyr Val
        755                 760                 765

Pro Leu Gly Ser Leu Arg Asp Tyr Leu Pro Arg His Ser Ile Gly Leu
770                 775                 780

Ala Gln Leu Leu Leu Phe Ala Gln Gln Ile Cys Glu Gly Met Ala Tyr
785                 790                 795                 800

Leu His Ala His Asp Tyr Ile His Arg Asp Leu Ala Ala Arg Asn Val
                805                 810                 815

Leu Leu Asp Asn Asp Arg Leu Val Lys Ile Gly Asp Phe Gly Leu Ala
            820                 825                 830

Lys Ala Val Pro Glu Gly His Glu Tyr Tyr Arg Val Arg Glu Asp Gly
        835                 840                 845

Asp Ser Pro Val Phe Trp Tyr Ala Pro Glu Cys Leu Lys Glu Tyr Lys
850                 855                 860

Phe Tyr Tyr Ala Ser Asp Val Trp Ser Phe Gly Val Thr Leu Tyr Glu
865                 870                 875                 880

Leu Leu Thr His Cys Asp Ser Ser Gln Ser Pro Pro Thr Lys Phe Leu
                885                 890                 895

Glu Leu Ile Gly Ile Ala Gln Gly Gln Met Thr Val Leu Arg Leu Thr
            900                 905                 910

Glu Leu Leu Glu Arg Gly Glu Arg Leu Pro Arg Pro Asp Lys Cys Pro
        915                 920                 925

Cys Glu Val Tyr His Leu Met Lys Asn Cys Trp Glu Thr Glu Ala Ser
930                 935                 940

Phe Arg Pro Thr Phe Glu Asn Leu Ile Pro Ile Leu Lys Thr Val His
945                 950                 955                 960

Glu Lys Tyr Gln Gly Gln Ala Pro Ser Val Phe Ser Val Cys Leu Glu
                965                 970                 975

Tyr Pro Tyr Asp Val Pro Asp Tyr Ala
            980                 985

<210> SEQ ID NO 4
<211> LENGTH: 975
<212> TYPE: PRT
<213> ORGANISM: Artificial Sequence
```

<220> FEATURE:
<223> OTHER INFORMATION: AGTR1-Tyk2(C) fusion construct

<400> SEQUENCE: 4

```
Met Ile Leu Asn Ser Ser Thr Glu Asp Gly Ile Lys Arg Ile Gln Asp
1               5                   10                  15

Asp Cys Pro Lys Ala Gly Arg His Asn Tyr Ile Phe Val Met Ile Pro
            20                  25                  30

Thr Leu Tyr Ser Ile Ile Phe Val Val Gly Ile Phe Gly Asn Ser Leu
        35                  40                  45

Val Val Ile Val Ile Tyr Phe Tyr Met Lys Leu Lys Thr Val Ala Ser
50                  55                  60

Val Phe Leu Leu Asn Leu Ala Leu Ala Asp Leu Cys Phe Leu Leu Thr
65                  70                  75                  80

Leu Pro Leu Trp Ala Val Tyr Thr Ala Met Glu Tyr Arg Trp Pro Phe
                85                  90                  95

Gly Asn Tyr Leu Cys Lys Ile Ala Ser Ala Ser Val Ser Phe Asn Leu
            100                 105                 110

Tyr Ala Ser Val Phe Leu Leu Thr Cys Leu Ser Ile Asp Arg Tyr Leu
        115                 120                 125

Ala Ile Val His Pro Met Lys Ser Arg Leu Arg Arg Thr Met Leu Val
130                 135                 140

Ala Lys Val Thr Cys Ile Ile Ile Trp Leu Leu Ala Gly Leu Ala Ser
145                 150                 155                 160

Leu Pro Ala Ile Ile His Arg Asn Val Phe Phe Ile Glu Asn Thr Asn
                165                 170                 175

Ile Thr Val Cys Ala Phe His Tyr Glu Ser Gln Asn Ser Thr Leu Pro
            180                 185                 190

Ile Gly Leu Gly Leu Thr Lys Asn Ile Leu Gly Phe Leu Phe Pro Phe
        195                 200                 205

Leu Ile Ile Leu Thr Ser Tyr Thr Leu Ile Trp Lys Ala Leu Lys Lys
210                 215                 220

Ala Tyr Glu Ile Gln Lys Asn Lys Pro Arg Asn Asp Asp Ile Phe Lys
225                 230                 235                 240

Ile Ile Met Ala Ile Val Leu Phe Phe Phe Ser Trp Ile Pro His
                245                 250                 255

Gln Ile Phe Thr Phe Leu Asp Val Leu Ile Gln Leu Gly Ile Ile Arg
            260                 265                 270

Asp Cys Arg Ile Ala Asp Ile Val Asp Thr Ala Met Pro Ile Thr Ile
        275                 280                 285

Cys Ile Ala Tyr Phe Asn Asn Cys Leu Asn Pro Leu Phe Tyr Gly Phe
290                 295                 300

Leu Gly Lys Lys Phe Lys Arg Tyr Phe Leu Gln Leu Leu Lys Tyr Ile
305                 310                 315                 320

Pro Pro Lys Ala Lys Ser His Ser Asn Leu Ser Thr Lys Met Ser Thr
                325                 330                 335

Leu Ser Tyr Arg Pro Ser Asp Asn Val Ser Ser Ser Thr Lys Lys Pro
            340                 345                 350

Ala Pro Cys Phe Glu Val Glu Ala Ala Gly Gly Ser Ile Thr Gln
        355                 360                 365

Leu Ser His Leu Gly Gln Gly Thr Arg Thr Asn Val Tyr Glu Gly Arg
370                 375                 380

Leu Arg Val Glu Gly Ser Gly Asp Pro Glu Glu Gly Lys Met Asp Asp
385                 390                 395                 400
```

```
Glu Asp Pro Leu Val Pro Gly Arg Asp Arg Gly Gln Glu Leu Arg Val
                405                 410                 415

Val Leu Lys Val Leu Asp Pro Ser His His Asp Ile Ala Leu Ala Phe
            420                 425                 430

Tyr Glu Thr Ala Ser Leu Met Ser Gln Val Ser His Thr His Leu Ala
        435                 440                 445

Phe Val His Gly Val Cys Val Arg Gly Pro Glu Asn Ser Met Val Thr
    450                 455                 460

Glu Tyr Val Glu His Gly Pro Leu Asp Val Trp Leu Arg Arg Glu Arg
465                 470                 475                 480

Gly His Val Pro Met Ala Trp Lys Met Val Val Ala Gln Gln Leu Ala
                485                 490                 495

Ser Ala Leu Ser Tyr Leu Glu Asn Lys Asn Leu Val His Gly Asn Val
            500                 505                 510

Cys Gly Arg Asn Ile Leu Leu Ala Arg Leu Gly Leu Ala Glu Gly Thr
        515                 520                 525

Ser Pro Phe Ile Lys Leu Ser Asp Pro Gly Val Gly Leu Gly Ala Leu
    530                 535                 540

Ser Arg Glu Glu Arg Val Glu Arg Ile Pro Trp Leu Ala Pro Glu Cys
545                 550                 555                 560

Leu Pro Gly Gly Ala Asn Ser Leu Ser Thr Ala Met Asp Lys Trp Gly
                565                 570                 575

Phe Gly Ala Thr Leu Leu Glu Ile Cys Phe Asp Gly Glu Ala Pro Leu
            580                 585                 590

Gln Ser Arg Ser Pro Ser Glu Lys Glu His Phe Tyr Gln Arg Gln His
        595                 600                 605

Arg Leu Pro Glu Pro Ser Cys Pro Gln Leu Ala Thr Leu Thr Ser Gln
    610                 615                 620

Cys Leu Thr Tyr Glu Pro Thr Gln Arg Pro Ser Phe Arg Thr Ile Leu
625                 630                 635                 640

Arg Asp Leu Thr Arg Val Gln Pro His Asn Leu Ala Asp Val Leu Thr
                645                 650                 655

Val Asn Arg Asp Ser Pro Ala Val Gly Pro Thr Thr Phe His Lys Arg
            660                 665                 670

Tyr Leu Lys Lys Ile Arg Asp Leu Gly Glu Gly His Phe Gly Lys Val
        675                 680                 685

Ser Leu Tyr Cys Tyr Asp Pro Thr Asn Asp Gly Thr Gly Glu Met Val
    690                 695                 700

Ala Val Lys Ala Leu Lys Ala Asp Cys Gly Pro Gln His Arg Ser Gly
705                 710                 715                 720

Trp Lys Gln Glu Ile Asp Ile Leu Arg Thr Leu Tyr His Glu His Ile
                725                 730                 735

Ile Lys Tyr Lys Gly Cys Cys Glu Asp Gln Gly Glu Lys Ser Leu Gln
            740                 745                 750

Leu Val Met Glu Tyr Val Pro Leu Gly Ser Leu Arg Asp Tyr Leu Pro
        755                 760                 765

Arg His Ser Ile Gly Leu Ala Gln Leu Leu Phe Ala Gln Gln Ile
    770                 775                 780

Cys Glu Gly Met Ala Tyr Leu His Ala His Asp Tyr Ile His Arg Asp
785                 790                 795                 800

Leu Ala Ala Arg Asn Val Leu Leu Asp Asn Asp Arg Leu Val Lys Ile
                805                 810                 815
```

```
Gly Asp Phe Gly Leu Ala Lys Ala Val Pro Glu Gly His Glu Tyr Tyr
            820                 825                 830

Arg Val Arg Glu Asp Gly Asp Ser Pro Val Phe Trp Tyr Ala Pro Glu
        835                 840                 845

Cys Leu Lys Glu Tyr Lys Phe Tyr Tyr Ala Ser Asp Val Trp Ser Phe
    850                 855                 860

Gly Val Thr Leu Tyr Glu Leu Leu Thr His Cys Asp Ser Ser Gln Ser
865                 870                 875                 880

Pro Pro Thr Lys Phe Leu Glu Leu Ile Gly Ile Ala Gln Gly Gln Met
                885                 890                 895

Thr Val Leu Arg Leu Thr Glu Leu Leu Glu Arg Gly Glu Arg Leu Pro
            900                 905                 910

Arg Pro Asp Lys Cys Pro Cys Glu Val Tyr His Leu Met Lys Asn Cys
        915                 920                 925

Trp Glu Thr Glu Ala Ser Phe Arg Pro Thr Phe Glu Asn Leu Ile Pro
    930                 935                 940

Ile Leu Lys Thr Val His Glu Lys Tyr Gln Gly Gln Ala Pro Ser Val
945                 950                 955                 960

Phe Ser Val Cys Leu Glu Tyr Pro Tyr Asp Val Pro Asp Tyr Ala
                965                 970                 975

<210> SEQ ID NO 5
<211> LENGTH: 1593
<212> TYPE: PRT
<213> ORGANISM: Artificial Sequence
<220> FEATURE:
<223> OTHER INFORMATION: ERN1-Tyk2(C) fusion construct

<400> SEQUENCE: 5

Met Pro Ala Arg Arg Leu Leu Leu Leu Thr Leu Leu Leu Pro Gly Leu
1               5                   10                  15

Leu Gly Ile Phe Gly Ser Thr Ser Thr Val Thr Leu Pro Glu Thr Leu
            20                  25                  30

Leu Phe Val Ser Thr Leu Asp Gly Ser Leu His Ala Val Ser Lys Arg
        35                  40                  45

Thr Gly Ser Ile Lys Trp Thr Leu Lys Glu Asp Pro Val Leu Gln Val
    50                  55                  60

Pro Thr His Val Glu Glu Pro Ala Phe Leu Pro Asp Pro Asn Asp Gly
65                  70                  75                  80

Ser Leu Tyr Thr Leu Gly Ser Lys Asn Asn Glu Gly Leu Thr Lys Leu
                85                  90                  95

Pro Phe Thr Ile Pro Glu Leu Val Gln Ala Ser Pro Cys Arg Ser Ser
            100                 105                 110

Asp Gly Ile Leu Tyr Met Gly Lys Lys Gln Asp Ile Trp Tyr Val Ile
        115                 120                 125

Asp Leu Leu Thr Gly Glu Lys Gln Gln Thr Leu Ser Ser Ala Phe Ala
    130                 135                 140

Asp Ser Leu Cys Pro Ser Thr Ser Leu Leu Tyr Leu Gly Arg Thr Glu
145                 150                 155                 160

Tyr Thr Ile Thr Met Tyr Asp Thr Lys Thr Arg Glu Leu Arg Trp Asn
                165                 170                 175

Ala Thr Tyr Phe Asp Tyr Ala Ala Ser Leu Pro Glu Asp Asp Val Asp
            180                 185                 190

Tyr Lys Met Ser His Phe Val Ser Asn Gly Asp Gly Leu Val Val Thr
        195                 200                 205
```

```
Val Asp Ser Glu Ser Gly Asp Val Leu Trp Ile Gln Asn Tyr Ala Ser
210                 215                 220

Pro Val Val Ala Phe Tyr Val Trp Gln Arg Glu Gly Leu Arg Lys Val
225                 230                 235                 240

Met His Ile Asn Val Ala Val Glu Thr Leu Arg Tyr Leu Thr Phe Met
            245                 250                 255

Ser Gly Glu Val Gly Arg Ile Thr Lys Trp Lys Tyr Pro Phe Pro Lys
                260                 265                 270

Glu Thr Glu Ala Lys Ser Lys Leu Thr Pro Thr Leu Tyr Val Gly Lys
            275                 280                 285

Tyr Ser Thr Ser Leu Tyr Ala Ser Pro Ser Met Val His Glu Gly Val
    290                 295                 300

Ala Val Val Pro Arg Gly Ser Thr Leu Pro Leu Leu Glu Gly Pro Gln
305                 310                 315                 320

Thr Asp Gly Val Thr Ile Gly Asp Lys Gly Glu Cys Val Ile Thr Pro
                325                 330                 335

Ser Thr Asp Val Lys Phe Asp Pro Gly Leu Lys Ser Lys Asn Lys Leu
            340                 345                 350

Asn Tyr Leu Arg Asn Tyr Trp Leu Leu Ile Gly His His Glu Thr Pro
        355                 360                 365

Leu Ser Ala Ser Thr Lys Met Leu Glu Arg Phe Pro Asn Asn Leu Pro
370                 375                 380

Lys His Arg Glu Asn Val Ile Pro Ala Asp Ser Glu Lys Lys Ser Phe
385                 390                 395                 400

Glu Glu Val Ile Asn Leu Val Asp Gln Thr Ser Glu Asn Ala Pro Thr
            405                 410                 415

Thr Val Ser Arg Asp Val Glu Glu Lys Pro Ala His Ala Pro Ala Arg
        420                 425                 430

Pro Glu Ala Pro Val Asp Ser Met Leu Lys Asp Met Ala Thr Ile Ile
            435                 440                 445

Leu Ser Thr Phe Leu Leu Ile Gly Trp Val Ala Phe Ile Ile Thr Tyr
    450                 455                 460

Pro Leu Ser Met His Gln Gln Gln Leu Gln His Gln Gln Phe Gln
465                 470                 475                 480

Lys Glu Leu Glu Lys Ile Gln Leu Leu Gln Gln Gln Gln Gln Leu
            485                 490                 495

Pro Phe His Pro Pro Gly Asp Thr Ala Gln Asp Gly Glu Leu Leu Asp
            500                 505                 510

Thr Ser Gly Pro Tyr Ser Glu Ser Ser Gly Thr Ser Ser Pro Ser Thr
    515                 520                 525

Ser Pro Arg Ala Ser Asn His Ser Leu Cys Ser Gly Ser Ser Ala Ser
530                 535                 540

Lys Ala Gly Ser Ser Pro Ser Leu Glu Gln Asp Asp Gly Asp Glu Glu
545                 550                 555                 560

Thr Ser Val Val Ile Val Gly Lys Ile Ser Phe Cys Pro Lys Asp Val
            565                 570                 575

Leu Gly His Gly Ala Glu Gly Thr Ile Val Tyr Arg Gly Met Phe Asp
        580                 585                 590

Asn Arg Asp Val Ala Val Lys Arg Ile Leu Pro Glu Cys Phe Ser Phe
    595                 600                 605

Ala Asp Arg Glu Val Gln Leu Leu Arg Glu Ser Asp Glu His Pro Asn
610                 615                 620

Val Ile Arg Tyr Phe Cys Thr Glu Lys Asp Arg Gln Phe Gln Tyr Ile
```

-continued

```
            625                 630                 635                 640
        Ala Ile Glu Leu Cys Ala Ala Thr Leu Gln Glu Tyr Val Gln Lys
                            645                 650                 655

Asp Phe Ala His Leu Gly Leu Glu Pro Ile Thr Leu Gln Gln Thr
                    660                 665                 670

Thr Ser Gly Leu Ala His Leu Ser Leu Asn Ile Val His Arg Asp
                675                 680                 685

Leu Lys Pro His Asn Ile Leu Ile Ser Met Pro Asn Ala His Gly Lys
            690                 695                 700

Ile Lys Ala Met Ile Ser Asp Phe Gly Leu Cys Lys Lys Leu Ala Val
        705                 710                 715                 720

Gly Arg His Ser Phe Ser Arg Arg Ser Gly Val Pro Gly Thr Glu Gly
                        725                 730                 735

Trp Ile Ala Pro Glu Met Leu Ser Glu Asp Cys Lys Glu Asn Pro Thr
                        740                 745                 750

Tyr Thr Val Asp Ile Phe Ser Ala Gly Cys Val Phe Tyr Tyr Val Ile
                    755                 760                 765

Ser Glu Gly Ser His Pro Phe Gly Lys Ser Leu Gln Arg Gln Ala Asn
            770                 775                 780

Ile Leu Leu Gly Ala Cys Ser Leu Asp Cys Leu His Pro Glu Lys His
        785                 790                 795                 800

Glu Asp Val Ile Ala Arg Glu Leu Ile Glu Lys Met Ile Ala Met Asp
                        805                 810                 815

Pro Gln Lys Arg Pro Ser Ala Lys His Val Leu Lys His Pro Phe Phe
                    820                 825                 830

Trp Ser Leu Glu Lys Gln Leu Gln Phe Phe Gln Asp Val Ser Asp Arg
                835                 840                 845

Ile Glu Lys Glu Ser Leu Asp Gly Pro Ile Val Lys Gln Leu Glu Arg
            850                 855                 860

Gly Gly Arg Ala Val Val Lys Met Asp Trp Arg Glu Asn Ile Thr Val
        865                 870                 875                 880

Pro Leu Gln Thr Asp Leu Arg Lys Phe Arg Thr Tyr Lys Gly Gly Ser
                        885                 890                 895

Val Arg Asp Leu Leu Arg Ala Met Arg Asn Lys Lys His His Tyr Arg
                    900                 905                 910

Glu Leu Pro Ala Glu Val Arg Glu Thr Leu Gly Ser Leu Pro Asp Asp
                915                 920                 925

Phe Val Cys Tyr Phe Thr Ser Arg Phe Pro His Leu Leu Ala His Thr
        930                 935                 940

Tyr Arg Ala Met Glu Leu Cys Ser His Glu Arg Leu Phe Gln Pro Tyr
        945                 950                 955                 960

Tyr Phe His Glu Pro Pro Glu Pro Gln Pro Pro Val Thr Pro Asp Ala
                        965                 970                 975

Leu Ala Ala Ala Gly Gly Ser Ile Thr Gln Leu Ser His Leu Gly Gln
                    980                 985                 990

Gly Thr Arg Thr Asn Val Tyr Glu Gly Arg Leu Arg Val Glu Gly Ser
                995                 1000                1005

Gly Asp Pro Glu Glu Gly Lys Met Asp Asp Glu Asp Pro Leu Val
            1010                1015                1020

Pro Gly Arg Asp Arg Gly Gln Glu Leu Arg Val Val Leu Lys Val
            1025                1030                1035

Leu Asp Pro Ser His His Asp Ile Ala Leu Ala Phe Tyr Glu Thr
            1040                1045                1050
```

```
Ala Ser Leu Met Ser Gln Val Ser His Thr His Leu Ala Phe Val
    1055            1060                1065
His Gly Val Cys Val Arg Gly Pro Glu Asn Ser Met Val Thr Glu
    1070            1075                1080
Tyr Val Glu His Gly Pro Leu Asp Val Trp Leu Arg Arg Glu Arg
    1085            1090                1095
Gly His Val Pro Met Ala Trp Lys Met Val Val Ala Gln Gln Leu
    1100            1105                1110
Ala Ser Ala Leu Ser Tyr Leu Glu Asn Lys Asn Leu Val His Gly
    1115            1120                1125
Asn Val Cys Gly Arg Asn Ile Leu Leu Ala Arg Leu Gly Leu Ala
    1130            1135                1140
Glu Gly Thr Ser Pro Phe Ile Lys Leu Ser Asp Pro Gly Val Gly
    1145            1150                1155
Leu Gly Ala Leu Ser Arg Glu Glu Arg Val Glu Arg Ile Pro Trp
    1160            1165                1170
Leu Ala Pro Glu Cys Leu Pro Gly Gly Ala Asn Ser Leu Ser Thr
    1175            1180                1185
Ala Met Asp Lys Trp Gly Phe Gly Ala Thr Leu Leu Glu Ile Cys
    1190            1195                1200
Phe Asp Gly Glu Ala Pro Leu Gln Ser Arg Ser Pro Ser Glu Lys
    1205            1210                1215
Glu His Phe Tyr Gln Arg Gln His Arg Leu Pro Glu Pro Ser Cys
    1220            1225                1230
Pro Gln Leu Ala Thr Leu Thr Ser Gln Cys Leu Thr Tyr Glu Pro
    1235            1240                1245
Thr Gln Arg Pro Ser Phe Arg Thr Ile Leu Arg Asp Leu Thr Arg
    1250            1255                1260
Val Gln Pro His Asn Leu Ala Asp Val Leu Thr Val Asn Arg Asp
    1265            1270                1275
Ser Pro Ala Val Gly Pro Thr Thr Phe His Lys Arg Tyr Leu Lys
    1280            1285                1290
Lys Ile Arg Asp Leu Gly Glu Gly His Phe Gly Lys Val Ser Leu
    1295            1300                1305
Tyr Cys Tyr Asp Pro Thr Asn Asp Gly Thr Gly Glu Met Val Ala
    1310            1315                1320
Val Lys Ala Leu Lys Ala Asp Cys Gly Pro Gln His Arg Ser Gly
    1325            1330                1335
Trp Lys Gln Glu Ile Asp Ile Leu Arg Thr Leu Tyr His Glu His
    1340            1345                1350
Ile Ile Lys Tyr Lys Gly Cys Cys Glu Asp Gln Gly Glu Lys Ser
    1355            1360                1365
Leu Gln Leu Val Met Glu Tyr Val Pro Leu Gly Ser Leu Arg Asp
    1370            1375                1380
Tyr Leu Pro Arg His Ser Ile Gly Leu Ala Gln Leu Leu Leu Phe
    1385            1390                1395
Ala Gln Gln Ile Cys Glu Gly Met Ala Tyr Leu His Ala His Asp
    1400            1405                1410
Tyr Ile His Arg Asp Leu Ala Ala Arg Asn Val Leu Leu Asp Asn
    1415            1420                1425
Asp Arg Leu Val Lys Ile Gly Asp Phe Gly Leu Ala Lys Ala Val
    1430            1435                1440
```

```
Pro Glu Gly His Glu Tyr Tyr Arg Val Arg Glu Asp Gly Asp Ser
    1445                1450                1455

Pro Val Phe Trp Tyr Ala Pro Glu Cys Leu Lys Glu Tyr Lys Phe
    1460                1465                1470

Tyr Tyr Ala Ser Asp Val Trp Ser Phe Gly Val Thr Leu Tyr Glu
    1475                1480                1485

Leu Leu Thr His Cys Asp Ser Ser Gln Ser Pro Thr Lys Phe
    1490                1495                1500

Leu Glu Leu Ile Gly Ile Ala Gln Gly Gln Met Thr Val Leu Arg
    1505                1510                1515

Leu Thr Glu Leu Leu Glu Arg Gly Glu Arg Leu Pro Arg Pro Asp
    1520                1525                1530

Lys Cys Pro Cys Glu Val Tyr His Leu Met Lys Asn Cys Trp Glu
    1535                1540                1545

Thr Glu Ala Ser Phe Arg Pro Thr Phe Glu Asn Leu Ile Pro Ile
    1550                1555                1560

Leu Lys Thr Val His Glu Lys Tyr Gln Gly Gln Ala Pro Ser Val
    1565                1570                1575

Phe Ser Val Cys Leu Glu Tyr Pro Tyr Asp Val Pro Asp Tyr Ala
    1580                1585                1590

<210> SEQ ID NO 6
<211> LENGTH: 612
<212> TYPE: PRT
<213> ORGANISM: Artificial Sequence
<220> FEATURE:
<223> OTHER INFORMATION: gp130-ARRB2 fusion construct

<400> SEQUENCE: 6

Met Asp Tyr Lys Asp Asp Asp Lys Ile Ser Thr Val His Ser
1               5                   10                  15

Gly Tyr Arg His Gln Val Pro Ser Val Gln Val Phe Ser Arg Ser Glu
                20                  25                  30

Ser Thr Gln Pro Leu Leu Asp Ser Glu Glu Arg Pro Glu Asp Leu Gln
            35                  40                  45

Leu Val Asp His Val Asp Gly Gly Asp Gly Ile Leu Pro Arg Gln Gln
        50                  55                  60

Tyr Phe Lys Gln Asn Cys Ser Gln His Glu Ser Ser Pro Asp Ile Ser
65                  70                  75                  80

His Phe Glu Arg Ser Lys Gln Val Ser Ser Val Asn Glu Glu Asp Phe
                85                  90                  95

Val Arg Leu Lys Gln Gln Ile Ser Asp His Ile Ser Gln Ser Cys Gly
                100                 105                 110

Ser Gly Gln Met Lys Met Phe Gln Glu Val Ser Ala Ala Asp Ala Phe
            115                 120                 125

Gly Pro Gly Thr Glu Gly Gln Val Glu Arg Phe Glu Thr Val Gly Met
        130                 135                 140

Glu Ala Ala Thr Asp Glu Gly Met Pro Lys Ser Tyr Leu Pro Gln Thr
145                 150                 155                 160

Val Arg Gln Gly Gly Tyr Met Pro Gln Gly Gly Ser Glu Leu Ser Thr
                165                 170                 175

Ser Leu Tyr Lys Lys Ala Gly Tyr Leu Pro Gln Thr Val Arg Gln Gly
                180                 185                 190

Gly Tyr Met Pro Gln Gly Gly Ser Glu Phe Thr Met Gly Glu Lys Pro
            195                 200                 205
```

```
Gly Thr Arg Val Phe Lys Lys Ser Pro Asn Cys Lys Leu Thr Val
    210                 215                 220

Tyr Leu Gly Lys Arg Asp Phe Val Asp His Leu Asp Lys Val Asp Pro
225                 230                 235                 240

Val Asp Gly Val Val Leu Val Asp Pro Asp Tyr Leu Lys Asp Arg Lys
                245                 250                 255

Val Phe Val Thr Leu Thr Cys Ala Phe Arg Tyr Gly Arg Glu Asp Leu
                260                 265                 270

Asp Val Leu Gly Leu Ser Phe Arg Lys Asp Leu Phe Ile Ala Thr Tyr
            275                 280                 285

Gln Ala Phe Pro Pro Val Pro Asn Pro Pro Arg Pro Pro Thr Arg Leu
290                 295                 300

Gln Asp Arg Leu Leu Arg Lys Leu Gly Gln His Ala His Pro Phe Phe
305                 310                 315                 320

Phe Thr Ile Pro Gln Asn Leu Pro Cys Ser Val Thr Leu Gln Pro Gly
                325                 330                 335

Pro Glu Asp Thr Gly Lys Ala Cys Gly Val Asp Phe Glu Ile Arg Ala
                340                 345                 350

Phe Cys Ala Lys Ser Leu Glu Glu Lys Ser His Lys Arg Asn Ser Val
            355                 360                 365

Arg Leu Val Ile Arg Lys Val Gln Phe Ala Pro Glu Lys Pro Gly Pro
370                 375                 380

Gln Pro Ser Ala Glu Thr Thr Arg His Phe Leu Met Ser Asp Arg Ser
385                 390                 395                 400

Leu His Leu Glu Ala Ser Leu Asp Lys Glu Leu Tyr Tyr His Gly Glu
                405                 410                 415

Pro Leu Asn Val Asn Val His Val Thr Asn Asn Ser Thr Lys Thr Val
                420                 425                 430

Lys Lys Ile Lys Val Ser Val Arg Gln Tyr Ala Asp Ile Cys Leu Phe
            435                 440                 445

Ser Thr Ala Gln Tyr Lys Cys Pro Val Ala Gln Leu Glu Gln Asp Asp
    450                 455                 460

Gln Val Ser Pro Ser Ser Thr Phe Cys Lys Val Tyr Thr Ile Thr Pro
465                 470                 475                 480

Leu Leu Ser Asp Asn Arg Glu Lys Arg Gly Leu Ala Leu Asp Gly Lys
                485                 490                 495

Leu Lys His Glu Asp Thr Asn Leu Ala Ser Ser Thr Ile Val Lys Glu
            500                 505                 510

Gly Ala Asn Lys Glu Val Leu Gly Ile Leu Val Ser Tyr Arg Val Lys
    515                 520                 525

Val Lys Leu Val Val Ser Arg Gly Gly Asp Val Ser Val Glu Leu Pro
530                 535                 540

Phe Val Leu Met His Pro Lys Pro His Asp His Ile Pro Leu Pro Arg
545                 550                 555                 560

Pro Gln Ser Ala Ala Pro Glu Thr Asp Val Pro Val Asp Thr Asn Leu
                565                 570                 575

Ile Glu Phe Asp Thr Asn Tyr Ala Thr Asp Asp Ile Val Phe Glu
                580                 585                 590

Asp Phe Ala Arg Leu Arg Leu Lys Gly Met Lys Asp Asp Asp Tyr Asp
            595                 600                 605

Asp Gln Leu Cys
    610
```

<210> SEQ ID NO 7
<211> LENGTH: 1187
<212> TYPE: PRT
<213> ORGANISM: Artificial Sequence
<220> FEATURE:
<223> OTHER INFORMATION: ERN1-gp130 fusion construct

<400> SEQUENCE: 7

```
Met Asp Tyr Lys Asp Asp Asp Lys Ile Ser Glu Phe Thr Met Pro
1               5                   10                  15

Ala Arg Arg Leu Leu Leu Leu Leu Thr Leu Leu Leu Pro Gly Leu Gly
            20                  25                  30

Ile Phe Gly Ser Thr Ser Thr Val Thr Leu Pro Glu Thr Leu Leu Phe
        35                  40                  45

Val Ser Thr Leu Asp Gly Ser Leu His Ala Val Ser Lys Arg Thr Gly
50                  55                  60

Ser Ile Lys Trp Thr Leu Lys Glu Asp Pro Val Leu Gln Val Pro Thr
65                  70                  75                  80

His Val Glu Glu Pro Ala Phe Leu Pro Asp Pro Asn Asp Gly Ser Leu
                85                  90                  95

Tyr Thr Leu Gly Ser Lys Asn Asn Glu Gly Leu Thr Lys Leu Pro Phe
            100                 105                 110

Thr Ile Pro Glu Leu Val Gln Ala Ser Pro Cys Arg Ser Ser Asp Gly
        115                 120                 125

Ile Leu Tyr Met Gly Lys Lys Gln Asp Ile Trp Tyr Val Ile Asp Leu
130                 135                 140

Leu Thr Gly Glu Lys Gln Gln Thr Leu Ser Ser Ala Phe Ala Asp Ser
145                 150                 155                 160

Leu Cys Pro Ser Thr Ser Leu Leu Tyr Leu Gly Arg Thr Glu Tyr Thr
                165                 170                 175

Ile Thr Met Tyr Asp Thr Lys Thr Arg Glu Leu Arg Trp Asn Ala Thr
            180                 185                 190

Tyr Phe Asp Tyr Ala Ala Ser Leu Pro Glu Asp Asp Val Asp Tyr Lys
        195                 200                 205

Met Ser His Phe Val Ser Asn Gly Asp Gly Leu Val Val Thr Val Asp
210                 215                 220

Ser Glu Ser Gly Asp Val Leu Trp Ile Gln Asn Tyr Ala Ser Pro Val
225                 230                 235                 240

Val Ala Phe Tyr Val Trp Gln Arg Glu Gly Leu Arg Lys Val Met His
                245                 250                 255

Ile Asn Val Ala Val Glu Thr Leu Arg Tyr Leu Thr Phe Met Ser Gly
            260                 265                 270

Glu Val Gly Arg Ile Thr Lys Trp Lys Tyr Pro Phe Pro Lys Glu Thr
        275                 280                 285

Glu Ala Lys Ser Lys Leu Thr Pro Thr Leu Tyr Val Gly Lys Tyr Ser
290                 295                 300

Thr Ser Leu Tyr Ala Ser Pro Ser Met Val His Glu Gly Val Ala Val
305                 310                 315                 320

Val Pro Arg Gly Ser Thr Leu Pro Leu Leu Glu Gly Pro Gln Thr Asp
                325                 330                 335

Gly Val Thr Ile Gly Asp Lys Gly Glu Cys Val Ile Thr Pro Ser Thr
            340                 345                 350

Asp Val Lys Phe Asp Pro Gly Leu Lys Ser Lys Asn Lys Leu Asn Tyr
        355                 360                 365

Leu Arg Asn Tyr Trp Leu Leu Ile Gly His His Glu Thr Pro Leu Ser
```

```
            370                 375                 380
Ala Ser Thr Lys Met Leu Glu Arg Phe Pro Asn Asn Leu Pro Lys His
385                 390                 395                 400

Arg Glu Asn Val Ile Pro Ala Asp Ser Glu Lys Lys Ser Phe Glu Glu
                405                 410                 415

Val Ile Asn Leu Val Asp Gln Thr Ser Glu Asn Ala Pro Thr Thr Val
            420                 425                 430

Ser Arg Asp Val Glu Glu Lys Pro Ala His Ala Pro Ala Arg Pro Glu
        435                 440                 445

Ala Pro Val Asp Ser Met Leu Lys Asp Met Ala Thr Ile Ile Leu Ser
450                 455                 460

Thr Phe Leu Leu Ile Gly Trp Val Ala Phe Ile Ile Thr Tyr Pro Leu
465                 470                 475                 480

Ser Met His Gln Gln Gln Leu Gln His Gln Gln Phe Gln Lys Glu
                485                 490                 495

Leu Glu Lys Ile Gln Leu Leu Gln Gln Gln Gln Gln Leu Pro Phe
            500                 505                 510

His Pro Pro Gly Asp Thr Ala Gln Asp Gly Glu Leu Leu Asp Thr Ser
        515                 520                 525

Gly Pro Tyr Ser Glu Ser Ser Gly Thr Ser Ser Pro Ser Thr Ser Pro
530                 535                 540

Arg Ala Ser Asn His Ser Leu Cys Ser Gly Ser Ser Ala Ser Lys Ala
545                 550                 555                 560

Gly Ser Ser Pro Ser Leu Glu Gln Asp Asp Gly Asp Glu Glu Thr Ser
                565                 570                 575

Val Val Ile Val Gly Lys Ile Ser Phe Cys Pro Lys Asp Val Leu Gly
            580                 585                 590

His Gly Ala Glu Gly Thr Ile Val Tyr Arg Gly Met Phe Asp Asn Arg
        595                 600                 605

Asp Val Ala Val Lys Arg Ile Leu Pro Glu Cys Phe Ser Phe Ala Asp
610                 615                 620

Arg Glu Val Gln Leu Leu Arg Glu Ser Asp Glu His Pro Asn Val Ile
625                 630                 635                 640

Arg Tyr Phe Cys Thr Glu Lys Asp Arg Gln Phe Gln Tyr Ile Ala Ile
                645                 650                 655

Glu Leu Cys Ala Ala Thr Leu Gln Glu Tyr Val Glu Gln Lys Asp Phe
            660                 665                 670

Ala His Leu Gly Leu Glu Pro Ile Thr Leu Leu Gln Gln Thr Thr Ser
        675                 680                 685

Gly Leu Ala His Leu His Ser Leu Asn Ile Val His Arg Asp Leu Lys
690                 695                 700

Pro His Asn Ile Leu Ile Ser Met Pro Asn Ala His Gly Lys Ile Lys
705                 710                 715                 720

Ala Met Ile Ser Asp Phe Gly Leu Cys Lys Lys Leu Ala Val Gly Arg
                725                 730                 735

His Ser Phe Ser Arg Arg Ser Gly Val Pro Gly Thr Glu Gly Trp Ile
            740                 745                 750

Ala Pro Glu Met Leu Ser Glu Asp Cys Lys Glu Asn Pro Thr Tyr Thr
        755                 760                 765

Val Asp Ile Phe Ser Ala Gly Cys Val Phe Tyr Tyr Val Ile Ser Glu
770                 775                 780

Gly Ser His Pro Phe Gly Lys Ser Leu Gln Arg Gln Ala Asn Ile Leu
785                 790                 795                 800
```

Leu Gly Ala Cys Ser Leu Asp Cys Leu His Pro Glu Lys His Glu Asp
                805                 810                 815

Val Ile Ala Arg Glu Leu Ile Glu Lys Met Ile Ala Met Asp Pro Gln
            820                 825                 830

Lys Arg Pro Ser Ala Lys His Val Leu Lys His Pro Phe Phe Trp Ser
        835                 840                 845

Leu Glu Lys Gln Leu Gln Phe Phe Gln Asp Val Ser Asp Arg Ile Glu
    850                 855                 860

Lys Glu Ser Leu Asp Gly Pro Ile Val Lys Gln Leu Glu Arg Gly Gly
865                 870                 875                 880

Arg Ala Val Val Lys Met Asp Trp Arg Glu Asn Ile Thr Val Pro Leu
                885                 890                 895

Gln Thr Asp Leu Arg Lys Phe Arg Thr Tyr Lys Gly Gly Ser Val Arg
            900                 905                 910

Asp Leu Leu Arg Ala Met Arg Asn Lys Lys His His Tyr Arg Glu Leu
        915                 920                 925

Pro Ala Glu Val Arg Glu Thr Leu Gly Ser Leu Pro Asp Asp Phe Val
    930                 935                 940

Cys Tyr Phe Thr Ser Arg Phe Pro His Leu Leu Ala His Thr Tyr Arg
945                 950                 955                 960

Ala Met Glu Leu Cys Ser His Glu Arg Leu Phe Gln Pro Tyr Tyr Phe
                965                 970                 975

His Glu Pro Pro Glu Pro Gln Pro Pro Val Thr Pro Asp Ala Leu Ser
            980                 985                 990

Arg Gly Ser Gly Gly Ser Gly Gly Ser Thr Val Val His Ser Gly Tyr
        995                 1000                1005

Arg His Gln Val Pro Ser Val Gln Val Phe Ser Arg Ser Glu Ser
    1010                1015                1020

Thr Gln Pro Leu Leu Asp Ser Glu Glu Arg Pro Glu Asp Leu Gln
    1025                1030                1035

Leu Val Asp His Val Asp Gly Gly Asp Gly Ile Leu Pro Arg Gln
    1040                1045                1050

Gln Tyr Phe Lys Gln Asn Cys Ser Gln His Glu Ser Ser Pro Asp
    1055                1060                1065

Ile Ser His Phe Glu Arg Ser Lys Gln Val Ser Ser Val Asn Glu
    1070                1075                1080

Glu Asp Phe Val Arg Leu Lys Gln Gln Ile Ser Asp His Ile Ser
    1085                1090                1095

Gln Ser Cys Gly Ser Gly Gln Met Lys Met Phe Gln Glu Val Ser
    1100                1105                1110

Ala Ala Asp Ala Phe Gly Pro Gly Thr Glu Gly Gln Val Glu Arg
    1115                1120                1125

Phe Glu Thr Val Gly Met Glu Ala Ala Thr Asp Glu Gly Met Pro
    1130                1135                1140

Lys Ser Tyr Leu Pro Gln Thr Val Arg Gln Gly Gly Tyr Met Pro
    1145                1150                1155

Gln Gly Gly Ser Glu Leu Ser Thr Ser Leu Tyr Lys Lys Ala Gly
    1160                1165                1170

Tyr Leu Pro Gln Thr Val Arg Gln Gly Gly Tyr Met Pro Gln
    1175                1180                1185

<210> SEQ ID NO 8
<211> LENGTH: 522

<212> TYPE: PRT
<213> ORGANISM: Homo sapiens

<400> SEQUENCE: 8

```
Gly Ser Asn Lys Ser Lys Pro Lys Asp Ala Ser Gln Arg Arg Arg Ser
1               5                   10                  15

Leu Glu Pro Ala Glu Asn Val His Gly Ala Gly Gly Ala Phe Pro
            20                  25                  30

Ala Ser Gln Thr Pro Ser Lys Pro Ala Ser Ala Asp Gly His Arg Gly
            35                  40                  45

Pro Ser Ala Ala Phe Ala Pro Ala Ala Glu Pro Lys Leu Phe Gly
50                  55                  60

Gly Phe Asn Ser Ser Asp Thr Val Thr Ser Pro Gln Arg Ala Gly Pro
65                  70                  75                  80

Leu Ala Gly Gly Val Thr Thr Phe Val Ala Leu Tyr Asp Tyr Glu Ser
                85                  90                  95

Arg Thr Glu Thr Asp Leu Ser Phe Lys Lys Gly Glu Arg Leu Gln Ile
            100                 105                 110

Val Asn Asn Thr Glu Gly Asp Trp Trp Leu Ala His Ser Leu Ser Thr
            115                 120                 125

Gly Gln Thr Gly Tyr Ile Pro Ser Asn Tyr Val Ala Pro Ser Asp Ser
130                 135                 140

Ile Gln Ala Glu Glu Trp Tyr Phe Gly Lys Ile Thr Arg Arg Glu Ser
145                 150                 155                 160

Glu Arg Leu Leu Leu Asn Ala Glu Asn Pro Arg Gly Thr Phe Leu Val
                165                 170                 175

Arg Glu Ser Glu Thr Thr Lys Gly Ala Tyr Cys Leu Ser Val Ser Asp
            180                 185                 190

Phe Asp Asn Ala Lys Gly Leu Asn Val Lys His Tyr Lys Ile Arg Lys
            195                 200                 205

Leu Asp Ser Gly Gly Phe Tyr Ile Thr Ser Arg Thr Gln Phe Asn Ser
210                 215                 220

Leu Gln Gln Leu Val Ala Tyr Tyr Ser Lys His Ala Asp Gly Leu Cys
225                 230                 235                 240

His Arg Leu Thr Thr Val Cys Pro Thr Ser Lys Pro Gln Thr Gln Gly
                245                 250                 255

Leu Ala Lys Asp Ala Trp Glu Ile Pro Arg Glu Ser Leu Arg Leu Glu
            260                 265                 270

Val Lys Leu Gly Gln Gly Cys Phe Gly Glu Val Trp Met Gly Thr Trp
            275                 280                 285

Asn Gly Thr Thr Arg Val Ala Ile Lys Thr Leu Lys Pro Gly Thr Met
290                 295                 300

Ser Pro Glu Ala Phe Leu Gln Glu Ala Gln Val Met Lys Lys Leu Arg
305                 310                 315                 320

His Glu Lys Leu Val Gln Leu Tyr Ala Val Val Ser Glu Glu Pro Ile
                325                 330                 335

Tyr Ile Val Thr Glu Tyr Met Ser Lys Gly Ser Leu Leu Asp Phe Leu
            340                 345                 350

Lys Gly Glu Thr Gly Lys Tyr Leu Arg Leu Pro Gln Leu Val Asp Met
            355                 360                 365

Ala Ala Gln Ile Ala Ser Gly Met Ala Tyr Val Glu Arg Met Asn Tyr
370                 375                 380

Val His Arg Asp Leu Arg Ala Ala Asn Ile Leu Val Gly Glu Asn Leu
385                 390                 395                 400
```

```
Val Cys Lys Val Ala Asp Phe Gly Leu Ala Arg Leu Ile Glu Asp Asn
            405                 410                 415

Glu Tyr Thr Ala Arg Gln Gly Ala Lys Phe Pro Ile Lys Trp Thr Ala
        420                 425                 430

Pro Glu Ala Leu Tyr Gly Arg Phe Thr Ile Lys Ser Asp Val Trp
        435                 440                 445

Ser Phe Gly Ile Leu Leu Thr Glu Leu Thr Thr Lys Gly Arg Val Pro
    450                 455                 460

Tyr Pro Gly Met Val Asn Arg Glu Val Leu Asp Gln Val Glu Arg Gly
465                 470                 475                 480

Tyr Arg Met Pro Cys Pro Pro Glu Cys Pro Glu Ser Leu His Asp Leu
                485                 490                 495

Met Cys Gln Cys Trp Arg Lys Glu Pro Glu Glu Arg Pro Thr Phe Glu
                500                 505                 510

Tyr Leu Gln Ala Phe Leu Glu Asp Tyr Phe
            515                 520

<210> SEQ ID NO 9
<211> LENGTH: 38
<212> TYPE: DNA
<213> ORGANISM: Artificial Sequence
<220> FEATURE:
<223> OTHER INFORMATION: Primer

<400> SEQUENCE: 9
cccaccggtc cggaattgac aagtttgtac aaaaaagc                              38

<210> SEQ ID NO 10
<211> LENGTH: 31
<212> TYPE: DNA
<213> ORGANISM: Artificial Sequence
<220> FEATURE:
<223> OTHER INFORMATION: Primer

<400> SEQUENCE: 10
gggggccccc aaccactttg tacaagaaag c                                    31

<210> SEQ ID NO 11
<211> LENGTH: 43
<212> TYPE: DNA
<213> ORGANISM: Artificial Sequence
<220> FEATURE:
<223> OTHER INFORMATION: Primer

<400> SEQUENCE: 11
cccgcggccg ctggcggttc gatcacccag ctgtcccact tgg                       43

<210> SEQ ID NO 12
<211> LENGTH: 63
<212> TYPE: DNA
<213> ORGANISM: Artificial Sequence
<220> FEATURE:
<223> OTHER INFORMATION: Primer

<400> SEQUENCE: 12
tctagactaa gcataatctg gaacatcata tggatactcg aggcacacgc tgaacactga     60
agg                                                                   63

<210> SEQ ID NO 13
<211> LENGTH: 73
<212> TYPE: DNA
```

<213> ORGANISM: Artificial Sequence
<220> FEATURE:
<223> OTHER INFORMATION: Primer

<400> SEQUENCE: 13
ccccaattga ccatgtatcc atatgatgtt ccagattatg ctttaattaa aatcacccag    60
ctgtcccact tgg    73

<210> SEQ ID NO 14
<211> LENGTH: 64
<212> TYPE: DNA
<213> ORGANISM: Artificial Sequence
<220> FEATURE:
<223> OTHER INFORMATION: Primer

<400> SEQUENCE: 14
gggtctagag cggccgcacc ggtcttaatt aagtcgacga attcgcacac gctgaacact    60
gaag    64

<210> SEQ ID NO 15
<211> LENGTH: 38
<212> TYPE: DNA
<213> ORGANISM: Artificial Sequence
<220> FEATURE:
<223> OTHER INFORMATION: Primer

<400> SEQUENCE: 15
cccaagcttg aattcaccat gggggagaaa cccgggac    38

<210> SEQ ID NO 16
<211> LENGTH: 33
<212> TYPE: DNA
<213> ORGANISM: Artificial Sequence
<220> FEATURE:
<223> OTHER INFORMATION: Primer

<400> SEQUENCE: 16
ggggcggccg cctagcagag ttgatcatca tag    33

<210> SEQ ID NO 17
<211> LENGTH: 39
<212> TYPE: DNA
<213> ORGANISM: Artificial Sequence
<220> FEATURE:
<223> OTHER INFORMATION: Primer

<400> SEQUENCE: 17
cccaagcttg gtaccaccat gccggcccgg cggctgctg    39

<210> SEQ ID NO 18
<211> LENGTH: 38
<212> TYPE: DNA
<213> ORGANISM: Artificial Sequence
<220> FEATURE:
<223> OTHER INFORMATION: Primer

<400> SEQUENCE: 18
cccgcggccg cgctagcgag ggcgtctgga gtcactgg    38

<210> SEQ ID NO 19
<211> LENGTH: 43
<212> TYPE: DNA
<213> ORGANISM: Artificial Sequence
<220> FEATURE:
<223> OTHER INFORMATION: Primer

<400> SEQUENCE: 19
cccgcggccg ctggcggttc gatcacccag ctgtccccact tgg        43

<210> SEQ ID NO 20
<211> LENGTH: 63
<212> TYPE: DNA
<213> ORGANISM: Artificial Sequence
<220> FEATURE:
<223> OTHER INFORMATION: Primer

<400> SEQUENCE: 20
gggcccctaa gcataatctg aacatcata tggatactcg aggcacacgc tgaacactga        60
agg        63

<210> SEQ ID NO 21
<211> LENGTH: 30
<212> TYPE: DNA
<213> ORGANISM: Artificial Sequence
<220> FEATURE:
<223> OTHER INFORMATION: Primer

<400> SEQUENCE: 21
cccgaattca tgccggcccg gcggctgctg        30

<210> SEQ ID NO 22
<211> LENGTH: 32
<212> TYPE: DNA
<213> ORGANISM: Artificial Sequence
<220> FEATURE:
<223> OTHER INFORMATION: Primer

<400> SEQUENCE: 22
cccctcgagg ggagggcgtc tggagtcact gg        32

<210> SEQ ID NO 23
<211> LENGTH: 30
<212> TYPE: DNA
<213> ORGANISM: Artificial Sequence
<220> FEATURE:
<223> OTHER INFORMATION: Primer

<400> SEQUENCE: 23
cccgaattct tctgtcccaa ggatgtcctg        30

<210> SEQ ID NO 24
<211> LENGTH: 35
<212> TYPE: DNA
<213> ORGANISM: Artificial Sequence
<220> FEATURE:
<223> OTHER INFORMATION: Primer

<400> SEQUENCE: 24
gggtaaaaag cagcccatct ggtatgttat tgacc        35

<210> SEQ ID NO 25
<211> LENGTH: 35
<212> TYPE: DNA
<213> ORGANISM: Artificial Sequence
<220> FEATURE:
<223> OTHER INFORMATION: Primer

<400> SEQUENCE: 25
ggtcaataac ataccagatg ggctgctttt taccc        35

<210> SEQ ID NO 26
<211> LENGTH: 30
<212> TYPE: DNA
<213> ORGANISM: Artificial Sequence
<220> FEATURE:
<223> OTHER INFORMATION: Primer

<400> SEQUENCE: 26
cccgatatct atggagacga cgcccttgaa                                              30

<210> SEQ ID NO 27
<211> LENGTH: 31
<212> TYPE: DNA
<213> ORGANISM: Artificial Sequence
<220> FEATURE:
<223> OTHER INFORMATION: Primer

<400> SEQUENCE: 27
ggggcggccg cttacacagc attcaagcgg a                                            31

<210> SEQ ID NO 28
<211> LENGTH: 1177
<212> TYPE: PRT
<213> ORGANISM: Artificial Sequence
<220> FEATURE:
<223> OTHER INFORMATION: HA-Tyk2(C)-RTp66 construct

<400> SEQUENCE: 28

```
Met Tyr Pro Tyr Asp Val Pro Asp Tyr Ala Leu Ile Lys Ile Thr Gln
1               5                   10                  15

Leu Ser His Leu Gly Gln Gly Thr Arg Thr Asn Val Tyr Glu Gly Arg
            20                  25                  30

Leu Arg Val Glu Gly Ser Gly Asp Pro Glu Glu Gly Lys Met Asp Asp
        35                  40                  45

Glu Asp Pro Leu Val Pro Gly Arg Asp Arg Gly Gln Glu Leu Arg Val
    50                  55                  60

Val Leu Lys Val Leu Asp Pro Ser His His Asp Ile Ala Leu Ala Phe
65                  70                  75                  80

Tyr Glu Thr Ala Ser Leu Met Ser Gln Val Ser His Thr His Leu Ala
                85                  90                  95

Phe Val His Gly Val Cys Val Arg Gly Pro Glu Asn Ser Met Val Thr
            100                 105                 110

Glu Tyr Val Glu His Gly Pro Leu Asp Val Trp Leu Arg Arg Glu Arg
        115                 120                 125

Gly His Val Pro Met Ala Trp Lys Met Val Val Ala Gln Gln Leu Ala
    130                 135                 140

Ser Ala Leu Ser Tyr Leu Glu Asn Lys Asn Leu Val His Gly Asn Val
145                 150                 155                 160

Cys Gly Arg Asn Ile Leu Leu Ala Arg Leu Gly Leu Ala Glu Gly Thr
                165                 170                 175

Ser Pro Phe Ile Lys Leu Ser Asp Pro Gly Val Gly Leu Gly Ala Leu
            180                 185                 190

Ser Arg Glu Glu Arg Val Glu Arg Ile Pro Trp Leu Ala Pro Glu Cys
        195                 200                 205

Leu Pro Gly Gly Ala Asn Ser Leu Ser Thr Ala Met Asp Lys Trp Gly
    210                 215                 220

Phe Gly Ala Thr Leu Leu Glu Ile Cys Phe Asp Gly Glu Ala Pro Leu
225                 230                 235                 240
```

```
Gln Ser Arg Ser Pro Ser Glu Lys Glu His Phe Tyr Gln Arg Gln His
                245                 250                 255
Arg Leu Pro Glu Pro Ser Cys Pro Gln Leu Ala Thr Leu Thr Ser Gln
            260                 265                 270
Cys Leu Thr Tyr Glu Pro Thr Gln Arg Pro Ser Phe Arg Thr Ile Leu
        275                 280                 285
Arg Asp Leu Thr Arg Val Gln Pro His Asn Leu Ala Asp Val Leu Thr
    290                 295                 300
Val Asn Arg Asp Ser Pro Ala Val Gly Pro Thr Phe His Lys Arg
305                 310                 315                 320
Tyr Leu Lys Lys Ile Arg Asp Leu Gly Glu Gly His Phe Gly Lys Val
                325                 330                 335
Ser Leu Tyr Cys Tyr Asp Pro Thr Asn Asp Gly Thr Gly Glu Met Val
            340                 345                 350
Ala Val Lys Ala Leu Lys Ala Asp Cys Gly Pro Gln His Arg Ser Gly
        355                 360                 365
Trp Lys Gln Glu Ile Asp Ile Leu Arg Thr Leu Tyr His Glu His Ile
    370                 375                 380
Ile Lys Tyr Lys Gly Cys Cys Glu Asp Gln Gly Glu Lys Ser Leu Gln
385                 390                 395                 400
Leu Val Met Glu Tyr Val Pro Leu Gly Ser Leu Arg Asp Tyr Leu Pro
                405                 410                 415
Arg His Ser Ile Gly Leu Ala Gln Leu Leu Phe Ala Gln Gln Ile
            420                 425                 430
Cys Glu Gly Met Ala Tyr Leu His Ala His Asp Tyr Ile His Arg Asp
    435                 440                 445
Leu Ala Ala Arg Asn Val Leu Leu Asp Asn Asp Arg Leu Val Lys Ile
450                 455                 460
Gly Asp Phe Gly Leu Ala Lys Ala Val Pro Glu Gly His Glu Tyr Tyr
465                 470                 475                 480
Arg Val Arg Glu Asp Gly Asp Ser Pro Val Phe Trp Tyr Ala Pro Glu
                485                 490                 495
Cys Leu Lys Glu Tyr Lys Phe Tyr Tyr Ala Ser Asp Val Trp Ser Phe
            500                 505                 510
Gly Val Thr Leu Tyr Glu Leu Leu Thr His Cys Asp Ser Ser Gln Ser
        515                 520                 525
Pro Pro Thr Lys Phe Leu Glu Leu Ile Gly Ile Ala Gln Gly Gln Met
    530                 535                 540
Thr Val Leu Arg Leu Thr Glu Leu Leu Glu Arg Gly Glu Arg Leu Pro
545                 550                 555                 560
Arg Pro Asp Lys Cys Pro Cys Glu Val Tyr His Leu Met Lys Asn Cys
                565                 570                 575
Trp Glu Thr Glu Ala Ser Phe Arg Pro Thr Phe Glu Asn Leu Ile Pro
            580                 585                 590
Ile Leu Lys Thr Val His Glu Lys Tyr Gln Gly Gln Ala Pro Ser Val
        595                 600                 605
Phe Ser Val Cys Glu Phe Gly Ser Ser Pro Ile Ser Pro Ile Glu Thr
    610                 615                 620
Val Pro Val Lys Leu Lys Pro Gly Met Asp Gly Pro Lys Val Lys Gln
625                 630                 635                 640
Trp Pro Leu Thr Glu Glu Lys Ile Lys Ala Leu Val Glu Ile Cys Thr
                645                 650                 655
Glu Met Glu Lys Glu Gly Lys Ile Ser Lys Ile Gly Pro Glu Asn Pro
```

```
                660             665             670
Tyr Asn Thr Pro Val Phe Ala Ile Lys Lys Asp Ser Thr Lys Trp
            675             680             685
Arg Lys Leu Val Asp Phe Arg Glu Leu Asn Lys Arg Thr Gln Asp Phe
690             695             700
Trp Glu Val Gln Leu Gly Ile Pro His Pro Ala Gly Leu Lys Gln Lys
705             710             715             720
Lys Ser Val Thr Val Leu Asp Val Gly Asp Ala Tyr Phe Ser Val Pro
            725             730             735
Leu Asp Lys Asp Phe Arg Lys Tyr Thr Ala Phe Thr Ile Pro Ser Ile
            740             745             750
Asn Asn Glu Thr Pro Gly Ile Arg Tyr Gln Tyr Asn Val Leu Pro Gln
        755             760             765
Gly Trp Lys Gly Ser Pro Ala Ile Phe Gln Cys Ser Met Thr Lys Ile
        770             775             780
Leu Glu Pro Phe Arg Lys Gln Asn Pro Asp Ile Val Ile Tyr Gln Tyr
785             790             795             800
Met Asp Asp Leu Tyr Val Gly Ser Asp Leu Glu Ile Gly Gln His Arg
            805             810             815
Thr Lys Ile Glu Glu Leu Arg Gln His Leu Leu Arg Trp Gly Phe Thr
            820             825             830
Thr Pro Asp Lys Lys His Gln Lys Glu Pro Pro Phe Leu Trp Met Gly
            835             840             845
Tyr Glu Leu His Pro Asp Lys Trp Thr Val Gln Pro Ile Val Leu Pro
        850             855             860
Glu Lys Asp Ser Trp Thr Val Asn Asp Ile Gln Lys Leu Val Gly Lys
865             870             875             880
Leu Asn Trp Ala Ser Gln Ile Tyr Ala Gly Ile Lys Val Arg Gln Leu
            885             890             895
Cys Lys Leu Leu Arg Gly Thr Lys Ala Leu Thr Glu Val Val Pro Leu
            900             905             910
Thr Glu Glu Ala Glu Leu Glu Leu Ala Glu Asn Arg Glu Ile Leu Lys
            915             920             925
Glu Pro Val His Gly Val Tyr Tyr Asp Pro Ser Lys Asp Leu Ile Ala
930             935             940
Glu Ile Gln Lys Gln Gly Gln Gly Gln Trp Thr Tyr Gln Ile Tyr Gln
945             950             955             960
Glu Pro Phe Lys Asn Leu Lys Thr Gly Lys Tyr Ala Arg Met Lys Gly
            965             970             975
Ala His Thr Asn Asp Val Lys Gln Leu Thr Glu Ala Val Gln Lys Ile
            980             985             990
Ala Thr Glu Ser Ile Val Ile Trp Gly Lys Thr Pro Lys Phe Lys Leu
            995             1000            1005
Pro Ile Gln Lys Glu Thr Trp Glu Ala Trp Trp Thr Glu Tyr Trp
    1010            1015            1020
Gln Ala Thr Trp Ile Pro Glu Trp Glu Phe Val Asn Thr Pro Pro
    1025            1030            1035
Leu Val Lys Leu Trp Tyr Gln Leu Glu Lys Glu Pro Ile Ile Gly
    1040            1045            1050
Ala Glu Thr Phe Tyr Val Asp Gly Ala Ala Asn Arg Glu Thr Lys
    1055            1060            1065
Leu Gly Lys Ala Gly Tyr Val Thr Asp Arg Gly Arg Gln Lys Val
    1070            1075            1080
```

```
Val Pro Leu Thr Asp Thr Thr Asn Gln Lys Thr Glu Leu Gln Ala
    1085                1090                1095

Ile His Leu Ala Leu Gln Asp Ser Gly Leu Glu Val Asn Ile Val
    1100                1105                1110

Thr Asp Ser Gln Tyr Ala Leu Gly Ile Ile Gln Ala Gln Pro Asp
    1115                1120                1125

Lys Ser Glu Ser Glu Leu Val Ser Gln Ile Ile Glu Gln Leu Ile
    1130                1135                1140

Lys Lys Glu Lys Val Tyr Leu Ala Trp Val Pro Ala His Lys Gly
    1145                1150                1155

Ile Gly Gly Asn Glu Gln Val Asp Gly Leu Val Ser Ala Gly Ile
    1160                1165                1170

Arg Lys Val Leu
    1175

<210> SEQ ID NO 29
<211> LENGTH: 1245
<212> TYPE: PRT
<213> ORGANISM: Artificial Sequence
<220> FEATURE:
<223> OTHER INFORMATION: HA-Tyk2(C)-SERT construct

<400> SEQUENCE: 29

Met Tyr Pro Tyr Asp Val Pro Asp Tyr Ala Leu Ile Lys Ile Thr Gln
1               5                   10                  15

Leu Ser His Leu Gly Gln Gly Thr Arg Thr Asn Val Tyr Glu Gly Arg
            20                  25                  30

Leu Arg Val Glu Gly Ser Gly Asp Pro Glu Glu Gly Lys Met Asp Asp
        35                  40                  45

Glu Asp Pro Leu Val Pro Gly Arg Asp Arg Gly Gln Glu Leu Arg Val
    50                  55                  60

Val Leu Lys Val Leu Asp Pro Ser His His Asp Ile Ala Leu Ala Phe
65                  70                  75                  80

Tyr Glu Thr Ala Ser Leu Met Ser Gln Val Ser His Thr His Leu Ala
                85                  90                  95

Phe Val His Gly Val Cys Val Arg Gly Pro Glu Asn Ser Met Val Thr
            100                 105                 110

Glu Tyr Val Glu His Gly Pro Leu Asp Val Trp Leu Arg Arg Glu Arg
        115                 120                 125

Gly His Val Pro Met Ala Trp Lys Met Val Val Ala Gln Gln Leu Ala
    130                 135                 140

Ser Ala Leu Ser Tyr Leu Glu Asn Lys Asn Leu Val His Gly Asn Val
145                 150                 155                 160

Cys Gly Arg Asn Ile Leu Leu Ala Arg Leu Gly Leu Ala Glu Gly Thr
                165                 170                 175

Ser Pro Phe Ile Lys Leu Ser Asp Pro Gly Val Gly Leu Gly Ala Leu
            180                 185                 190

Ser Arg Glu Glu Arg Val Glu Arg Ile Pro Trp Leu Ala Pro Glu Cys
        195                 200                 205

Leu Pro Gly Gly Ala Asn Ser Leu Ser Thr Ala Met Asp Lys Trp Gly
    210                 215                 220

Phe Gly Ala Thr Leu Leu Glu Ile Cys Phe Asp Gly Glu Ala Pro Leu
225                 230                 235                 240

Gln Ser Arg Ser Pro Ser Glu Lys Glu His Phe Tyr Gln Arg Gln His
                245                 250                 255
```

```
Arg Leu Pro Glu Pro Ser Cys Pro Gln Leu Ala Thr Leu Thr Ser Gln
            260                 265                 270

Cys Leu Thr Tyr Glu Pro Thr Gln Arg Pro Ser Phe Arg Thr Ile Leu
            275                 280                 285

Arg Asp Leu Thr Arg Val Gln Pro His Asn Leu Ala Asp Val Leu Thr
290                 295                 300

Val Asn Arg Asp Ser Pro Ala Val Gly Pro Thr Thr Phe His Lys Arg
305                 310                 315                 320

Tyr Leu Lys Lys Ile Arg Asp Leu Gly Glu Gly His Phe Gly Lys Val
                325                 330                 335

Ser Leu Tyr Cys Tyr Asp Pro Thr Asn Asp Gly Thr Gly Glu Met Val
            340                 345                 350

Ala Val Lys Ala Leu Lys Ala Asp Cys Gly Pro Gln His Arg Ser Gly
            355                 360                 365

Trp Lys Gln Glu Ile Asp Ile Leu Arg Thr Leu Tyr His Glu His Ile
            370                 375                 380

Ile Lys Tyr Lys Gly Cys Cys Glu Asp Gln Gly Glu Lys Ser Leu Gln
385                 390                 395                 400

Leu Val Met Glu Tyr Val Pro Leu Gly Ser Leu Arg Asp Tyr Leu Pro
                405                 410                 415

Arg His Ser Ile Gly Leu Ala Gln Leu Leu Leu Phe Ala Gln Gln Ile
            420                 425                 430

Cys Glu Gly Met Ala Tyr Leu His Ala His Asp Tyr Ile His Arg Asp
            435                 440                 445

Leu Ala Ala Arg Asn Val Leu Leu Asp Asn Asp Arg Leu Val Lys Ile
450                 455                 460

Gly Asp Phe Gly Leu Ala Lys Ala Val Pro Glu Gly His Glu Tyr Tyr
465                 470                 475                 480

Arg Val Arg Glu Asp Gly Asp Ser Pro Val Phe Trp Tyr Ala Pro Glu
                485                 490                 495

Cys Leu Lys Glu Tyr Lys Phe Tyr Tyr Ala Ser Asp Val Trp Ser Phe
            500                 505                 510

Gly Val Thr Leu Tyr Glu Leu Leu Thr His Cys Asp Ser Ser Gln Ser
            515                 520                 525

Pro Pro Thr Lys Phe Leu Glu Leu Ile Gly Ile Ala Gln Gly Gln Met
530                 535                 540

Thr Val Leu Arg Leu Thr Glu Leu Leu Glu Arg Gly Glu Arg Leu Pro
545                 550                 555                 560

Arg Pro Asp Lys Cys Pro Cys Glu Val Tyr His Leu Met Lys Asn Cys
                565                 570                 575

Trp Glu Thr Glu Ala Ser Phe Arg Pro Thr Phe Glu Asn Leu Ile Pro
            580                 585                 590

Ile Leu Lys Thr Val His Glu Lys Tyr Gln Gly Gln Ala Pro Ser Val
            595                 600                 605

Phe Ser Val Cys Glu Leu Ser Met Glu Thr Thr Pro Leu Asn Ser Gln
            610                 615                 620

Lys Gln Leu Ser Ala Cys Glu Asp Gly Glu Asp Cys Gln Glu Asn Gly
625                 630                 635                 640

Val Leu Gln Lys Val Val Pro Thr Pro Gly Asp Lys Val Glu Ser Gly
                645                 650                 655

Gln Ile Ser Asn Gly Tyr Ser Ala Val Pro Ser Pro Gly Ala Gly Asp
            660                 665                 670
```

-continued

```
Asp Thr Arg His Ser Ile Pro Ala Thr Thr Thr Leu Val Ala Glu
            675                 680                 685

Leu His Gln Gly Glu Arg Glu Thr Trp Gly Lys Lys Val Asp Phe Leu
    690                 695                 700

Leu Ser Val Ile Gly Tyr Ala Val Asp Leu Gly Asn Val Trp Arg Phe
705                 710                 715                 720

Pro Tyr Ile Cys Tyr Gln Asn Gly Gly Ala Phe Leu Pro Tyr
                725                 730                 735

Thr Ile Met Ala Ile Phe Gly Gly Ile Pro Leu Phe Tyr Met Glu Leu
            740                 745                 750

Ala Leu Gly Gln Tyr His Arg Asn Gly Cys Ile Ser Ile Trp Arg Lys
            755                 760                 765

Ile Cys Pro Ile Phe Lys Gly Ile Gly Tyr Ala Ile Cys Ile Ile Ala
            770                 775                 780

Phe Tyr Ile Ala Ser Tyr Tyr Asn Thr Ile Met Ala Trp Ala Leu Tyr
785                 790                 795                 800

Tyr Leu Ile Ser Ser Phe Thr Asp Gln Leu Pro Trp Thr Ser Cys Lys
                805                 810                 815

Asn Ser Trp Asn Thr Gly Asn Cys Thr Asn Tyr Phe Ser Glu Asp Asn
            820                 825                 830

Ile Thr Trp Thr Leu His Ser Thr Ser Pro Ala Glu Glu Phe Tyr Thr
            835                 840                 845

Arg His Val Leu Gln Ile His Arg Ser Lys Gly Leu Gln Asp Leu Gly
            850                 855                 860

Gly Ile Ser Trp Gln Leu Ala Leu Cys Ile Met Leu Ile Phe Thr Val
865                 870                 875                 880

Ile Tyr Phe Ser Ile Trp Lys Gly Val Lys Thr Ser Gly Lys Val Val
                885                 890                 895

Trp Val Thr Ala Thr Phe Pro Tyr Ile Ile Leu Ser Val Leu Leu Val
            900                 905                 910

Arg Gly Ala Thr Leu Pro Gly Ala Trp Arg Gly Val Leu Phe Tyr Leu
            915                 920                 925

Lys Pro Asn Trp Gln Lys Leu Leu Glu Thr Gly Val Trp Ile Asp Ala
930                 935                 940

Ala Ala Gln Ile Phe Phe Ser Leu Gly Pro Gly Phe Gly Val Leu Leu
945                 950                 955                 960

Ala Phe Ala Ser Tyr Asn Lys Phe Asn Asn Asn Cys Tyr Gln Asp Ala
                965                 970                 975

Leu Val Thr Ser Val Val Asn Cys Met Thr Ser Phe Val Ser Gly Phe
            980                 985                 990

Val Ile Phe Thr Val Leu Gly Tyr Met Ala Glu Met Arg Asn Glu Asp
            995                 1000                1005

Val Ser Glu Val Ala Lys Asp Ala Gly Pro Ser Leu Leu Phe Ile
    1010                1015                1020

Thr Tyr Ala Glu Ala Ile Ala Asn Met Pro Ala Ser Thr Phe Phe
    1025                1030                1035

Ala Ile Ile Phe Phe Leu Met Leu Ile Thr Leu Gly Leu Asp Ser
    1040                1045                1050

Thr Phe Ala Gly Leu Glu Gly Val Ile Thr Ala Val Leu Asp Glu
    1055                1060                1065

Phe Pro His Val Trp Ala Lys Arg Arg Glu Arg Phe Val Leu Ala
    1070                1075                1080

Val Val Ile Thr Cys Phe Phe Gly Ser Leu Val Thr Leu Thr Phe
```

```
                    1085                1090                1095

Gly  Gly  Ala  Tyr  Val  Val  Lys  Leu  Leu  Glu  Glu  Tyr  Ala  Thr  Gly
               1100                1105                1110

Pro  Ala  Val  Leu  Thr  Val  Ala  Leu  Ile  Glu  Ala  Val  Ala  Val  Ser
          1115                1120                1125

Trp  Phe  Tyr  Gly  Ile  Thr  Gln  Phe  Cys  Arg  Asp  Val  Lys  Glu  Met
     1130                1135                1140

Leu  Gly  Phe  Ser  Pro  Gly  Trp  Phe  Trp  Arg  Ile  Cys  Trp  Val  Ala
1145                1150                1155

Ile  Ser  Pro  Leu  Phe  Leu  Leu  Phe  Ile  Ile  Cys  Ser  Phe  Leu  Met
     1160                1165                1170

Ser  Pro  Pro  Gln  Leu  Arg  Leu  Phe  Gln  Tyr  Asn  Tyr  Pro  Tyr  Trp
1175                1180                1185

Ser  Ile  Ile  Leu  Gly  Tyr  Cys  Ile  Gly  Thr  Ser  Ser  Phe  Ile  Cys
     1190                1195                1200

Ile  Pro  Thr  Tyr  Ile  Ala  Tyr  Arg  Leu  Ile  Ile  Thr  Pro  Gly  Thr
1205                1210                1215

Phe  Lys  Glu  Arg  Ile  Ile  Lys  Ser  Ile  Thr  Pro  Glu  Thr  Pro  Thr
     1220                1225                1230

Glu  Ile  Pro  Cys  Gly  Asp  Ile  Arg  Leu  Asn  Ala  Val
1235                1240                1245
```

<210> SEQ ID NO 30
<211> LENGTH: 1593
<212> TYPE: PRT
<213> ORGANISM: Artificial Sequence
<220> FEATURE:
<223> OTHER INFORMATION: ERN1(K599A)-Tyk2(C)-HA fusion protein

<400> SEQUENCE: 30

```
Met  Pro  Ala  Arg  Arg  Leu  Leu  Leu  Leu  Leu  Thr  Leu  Leu  Pro  Gly
1                   5                   10                  15

Leu  Gly  Ile  Phe  Gly  Ser  Thr  Ser  Thr  Val  Thr  Leu  Pro  Glu  Thr  Leu
          20                  25                  30

Leu  Phe  Val  Ser  Thr  Leu  Asp  Gly  Ser  Leu  His  Ala  Val  Ser  Lys  Arg
     35                  40                  45

Thr  Gly  Ser  Ile  Lys  Trp  Thr  Leu  Lys  Glu  Asp  Pro  Val  Leu  Gln  Val
50                  55                  60

Pro  Thr  His  Val  Glu  Glu  Pro  Ala  Phe  Leu  Pro  Asp  Pro  Asn  Asp  Gly
65                  70                  75                  80

Ser  Leu  Tyr  Thr  Leu  Gly  Ser  Lys  Asn  Asn  Glu  Gly  Leu  Thr  Lys  Leu
               85                  90                  95

Pro  Phe  Thr  Ile  Pro  Glu  Leu  Val  Gln  Ala  Ser  Pro  Cys  Arg  Ser  Ser
          100                 105                 110

Asp  Gly  Ile  Leu  Tyr  Met  Gly  Lys  Lys  Gln  Asp  Ile  Trp  Tyr  Val  Ile
     115                 120                 125

Asp  Leu  Leu  Thr  Gly  Glu  Lys  Gln  Gln  Thr  Leu  Ser  Ser  Ala  Phe  Ala
130                 135                 140

Asp  Ser  Leu  Cys  Pro  Ser  Thr  Ser  Leu  Leu  Tyr  Leu  Gly  Arg  Thr  Glu
145                 150                 155                 160

Tyr  Thr  Ile  Thr  Met  Tyr  Asp  Thr  Lys  Thr  Arg  Glu  Leu  Arg  Trp  Asn
                    165                 170                 175

Ala  Thr  Tyr  Phe  Asp  Tyr  Ala  Ala  Ser  Leu  Pro  Glu  Asp  Asp  Val  Asp
               180                 185                 190

Tyr  Lys  Met  Ser  His  Phe  Val  Ser  Asn  Gly  Asp  Gly  Leu  Val  Val  Thr
```

-continued

```
            195                 200                 205
Val Asp Ser Glu Ser Gly Asp Val Leu Trp Ile Gln Asn Tyr Ala Ser
210                 215                 220

Pro Val Ala Phe Tyr Val Trp Gln Arg Glu Gly Leu Arg Lys Val
225                 230                 235                 240

Met His Ile Asn Val Ala Val Glu Thr Leu Arg Tyr Leu Thr Phe Met
                    245                 250                 255

Ser Gly Glu Val Gly Arg Ile Thr Lys Trp Lys Tyr Pro Phe Pro Lys
                260                 265                 270

Glu Thr Glu Ala Lys Ser Lys Leu Thr Pro Thr Leu Tyr Val Gly Lys
            275                 280                 285

Tyr Ser Thr Ser Leu Tyr Ala Ser Pro Ser Met Val His Glu Gly Val
        290                 295                 300

Ala Val Val Pro Arg Gly Ser Thr Leu Pro Leu Leu Glu Gly Pro Gln
305                 310                 315                 320

Thr Asp Gly Val Thr Ile Gly Asp Lys Gly Glu Cys Val Ile Thr Pro
                    325                 330                 335

Ser Thr Asp Val Lys Phe Asp Pro Gly Leu Lys Ser Lys Asn Lys Leu
                340                 345                 350

Asn Tyr Leu Arg Asn Tyr Trp Leu Ile Gly His His Glu Thr Pro
            355                 360                 365

Leu Ser Ala Ser Thr Lys Met Leu Glu Arg Phe Pro Asn Asn Leu Pro
        370                 375                 380

Lys His Arg Glu Asn Val Ile Pro Ala Asp Ser Glu Lys Lys Ser Phe
385                 390                 395                 400

Glu Glu Val Ile Asn Leu Val Asp Gln Thr Ser Glu Asn Ala Pro Thr
                    405                 410                 415

Thr Val Ser Arg Asp Val Glu Glu Lys Pro Ala His Ala Pro Ala Arg
                420                 425                 430

Pro Glu Ala Pro Val Asp Ser Met Leu Lys Asp Met Ala Thr Ile Ile
            435                 440                 445

Leu Ser Thr Phe Leu Leu Ile Gly Trp Val Ala Phe Ile Ile Thr Tyr
        450                 455                 460

Pro Leu Ser Met His Gln Gln Gln Leu Gln His Gln Gln Phe Gln
465                 470                 475                 480

Lys Glu Leu Glu Lys Ile Gln Leu Leu Gln Gln Gln Gln Gln Leu
                    485                 490                 495

Pro Phe His Pro Pro Asp Thr Ala Gln Asp Gly Glu Leu Leu Asp
                500                 505                 510

Thr Ser Gly Pro Tyr Ser Glu Ser Ser Gly Thr Ser Ser Pro Ser Thr
            515                 520                 525

Ser Pro Arg Ala Ser Asn His Ser Leu Cys Ser Gly Ser Ser Ala Ser
530                 535                 540

Lys Ala Gly Ser Ser Pro Ser Leu Glu Gln Asp Asp Gly Asp Glu Glu
545                 550                 555                 560

Thr Ser Val Val Ile Val Gly Lys Ile Ser Phe Cys Pro Lys Asp Val
                    565                 570                 575

Leu Gly His Gly Ala Glu Gly Thr Ile Val Tyr Arg Gly Met Phe Asp
                580                 585                 590

Asn Arg Asp Val Ala Val Ala Arg Ile Leu Pro Glu Cys Phe Ser Phe
            595                 600                 605

Ala Asp Arg Glu Val Gln Leu Leu Arg Glu Ser Asp Glu His Pro Asn
610                 615                 620
```

```
Val Ile Arg Tyr Phe Cys Thr Glu Lys Asp Arg Gln Phe Gln Tyr Ile
625                 630                 635                 640

Ala Ile Glu Leu Cys Ala Ala Thr Leu Gln Glu Tyr Val Glu Gln Lys
                645                 650                 655

Asp Phe Ala His Leu Gly Leu Glu Pro Ile Thr Leu Gln Gln Thr
            660                 665                 670

Thr Ser Gly Leu Ala His Leu His Ser Leu Asn Ile Val His Arg Asp
        675                 680                 685

Leu Lys Pro His Asn Ile Leu Ile Ser Met Pro Asn Ala His Gly Lys
690                 695                 700

Ile Lys Ala Met Ile Ser Asp Phe Gly Leu Cys Lys Lys Leu Ala Val
705                 710                 715                 720

Gly Arg His Ser Phe Ser Arg Arg Ser Gly Val Pro Gly Thr Glu Gly
                725                 730                 735

Trp Ile Ala Pro Glu Met Leu Ser Glu Asp Cys Lys Glu Asn Pro Thr
                740                 745                 750

Tyr Thr Val Asp Ile Phe Ser Ala Gly Cys Val Phe Tyr Tyr Val Ile
            755                 760                 765

Ser Glu Gly Ser His Pro Phe Gly Lys Ser Leu Gln Arg Gln Ala Asn
770                 775                 780

Ile Leu Leu Gly Ala Cys Ser Leu Asp Cys Leu His Pro Glu Lys His
785                 790                 795                 800

Glu Asp Val Ile Ala Arg Glu Leu Ile Glu Lys Met Ile Ala Met Asp
                805                 810                 815

Pro Gln Lys Arg Pro Ser Ala Lys His Val Leu Lys His Pro Phe Phe
            820                 825                 830

Trp Ser Leu Glu Lys Gln Leu Gln Phe Phe Gln Asp Val Ser Asp Arg
        835                 840                 845

Ile Glu Lys Glu Ser Leu Asp Gly Pro Ile Val Lys Gln Leu Glu Arg
850                 855                 860

Gly Gly Arg Ala Val Val Lys Met Asp Trp Arg Glu Asn Ile Thr Val
865                 870                 875                 880

Pro Leu Gln Thr Asp Leu Arg Lys Phe Arg Thr Tyr Lys Gly Gly Ser
                885                 890                 895

Val Arg Asp Leu Leu Arg Ala Met Arg Asn Lys Lys His His Tyr Arg
            900                 905                 910

Glu Leu Pro Ala Glu Val Arg Glu Thr Leu Gly Ser Leu Pro Asp Asp
        915                 920                 925

Phe Val Cys Tyr Phe Thr Ser Arg Phe Pro His Leu Leu Ala His Thr
930                 935                 940

Tyr Arg Ala Met Glu Leu Cys Ser His Glu Arg Leu Phe Gln Pro Tyr
945                 950                 955                 960

Tyr Phe His Glu Pro Pro Glu Pro Gln Pro Val Thr Pro Asp Ala
                965                 970                 975

Leu Ala Ala Ala Gly Gly Ser Ile Thr Gln Leu Ser His Leu Gly Gln
            980                 985                 990

Gly Thr Arg Thr Asn Val Tyr Glu Gly Arg Leu Arg Val Glu Gly Ser
        995                 1000                1005

Gly Asp Pro Glu Glu Gly Lys Met Asp Asp Glu Asp Pro Leu Val
            1010                1015                1020

Pro Gly Arg Asp Arg Gly Gln Glu Leu Arg Val Val Leu Lys Val
        1025                1030                1035
```

| | | | | | | | | | | | |
|---|---|---|---|---|---|---|---|---|---|---|---|
| Leu | Asp | Pro | Ser | His | His | Asp | Ile | Ala | Leu | Ala | Phe | Tyr | Glu | Thr |
| | 1040 | | | | | 1045 | | | | 1050 | | | | |
| Ala | Ser | Leu | Met | Ser | Gln | Val | Ser | His | Thr | His | Leu | Ala | Phe | Val |
| | 1055 | | | | | 1060 | | | | 1065 | | | | |
| His | Gly | Val | Cys | Val | Arg | Gly | Pro | Glu | Asn | Ser | Met | Val | Thr | Glu |
| | 1070 | | | | | 1075 | | | | 1080 | | | | |
| Tyr | Val | Glu | His | Gly | Pro | Leu | Asp | Val | Trp | Leu | Arg | Arg | Glu | Arg |
| | 1085 | | | | | 1090 | | | | 1095 | | | | |
| Gly | His | Val | Pro | Met | Ala | Trp | Lys | Met | Val | Val | Ala | Gln | Gln | Leu |
| | 1100 | | | | | 1105 | | | | 1110 | | | | |
| Ala | Ser | Ala | Leu | Ser | Tyr | Leu | Glu | Asn | Lys | Asn | Leu | Val | His | Gly |
| | 1115 | | | | | 1120 | | | | 1125 | | | | |
| Asn | Val | Cys | Gly | Arg | Asn | Ile | Leu | Leu | Ala | Arg | Leu | Gly | Leu | Ala |
| | 1130 | | | | | 1135 | | | | 1140 | | | | |
| Glu | Gly | Thr | Ser | Pro | Phe | Ile | Lys | Leu | Ser | Asp | Pro | Gly | Val | Gly |
| | 1145 | | | | | 1150 | | | | 1155 | | | | |
| Leu | Gly | Ala | Leu | Ser | Arg | Glu | Glu | Arg | Val | Glu | Arg | Ile | Pro | Trp |
| | 1160 | | | | | 1165 | | | | 1170 | | | | |
| Leu | Ala | Pro | Glu | Cys | Leu | Pro | Gly | Gly | Ala | Asn | Ser | Leu | Ser | Thr |
| | 1175 | | | | | 1180 | | | | 1185 | | | | |
| Ala | Met | Asp | Lys | Trp | Gly | Phe | Gly | Ala | Thr | Leu | Leu | Glu | Ile | Cys |
| | 1190 | | | | | 1195 | | | | 1200 | | | | |
| Phe | Asp | Gly | Glu | Ala | Pro | Leu | Gln | Ser | Arg | Ser | Pro | Ser | Glu | Lys |
| | 1205 | | | | | 1210 | | | | 1215 | | | | |
| Glu | His | Phe | Tyr | Gln | Arg | Gln | His | Arg | Leu | Pro | Glu | Pro | Ser | Cys |
| | 1220 | | | | | 1225 | | | | 1230 | | | | |
| Pro | Gln | Leu | Ala | Thr | Leu | Thr | Ser | Gln | Cys | Leu | Thr | Tyr | Glu | Pro |
| | 1235 | | | | | 1240 | | | | 1245 | | | | |
| Thr | Gln | Arg | Pro | Ser | Phe | Arg | Thr | Ile | Leu | Arg | Asp | Leu | Thr | Arg |
| | 1250 | | | | | 1255 | | | | 1260 | | | | |
| Val | Gln | Pro | His | Asn | Leu | Ala | Asp | Val | Leu | Thr | Val | Asn | Arg | Asp |
| | 1265 | | | | | 1270 | | | | 1275 | | | | |
| Ser | Pro | Ala | Val | Gly | Pro | Thr | Thr | Phe | His | Lys | Arg | Tyr | Leu | Lys |
| | 1280 | | | | | 1285 | | | | 1290 | | | | |
| Lys | Ile | Arg | Asp | Leu | Gly | Glu | Gly | His | Phe | Gly | Lys | Val | Ser | Leu |
| | 1295 | | | | | 1300 | | | | 1305 | | | | |
| Tyr | Cys | Tyr | Asp | Pro | Thr | Asn | Asp | Gly | Thr | Gly | Glu | Met | Val | Ala |
| | 1310 | | | | | 1315 | | | | 1320 | | | | |
| Val | Lys | Ala | Leu | Lys | Ala | Asp | Cys | Gly | Pro | Gln | His | Arg | Ser | Gly |
| | 1325 | | | | | 1330 | | | | 1335 | | | | |
| Trp | Lys | Gln | Glu | Ile | Asp | Ile | Leu | Arg | Thr | Leu | Tyr | His | Glu | His |
| | 1340 | | | | | 1345 | | | | 1350 | | | | |
| Ile | Ile | Lys | Tyr | Lys | Gly | Cys | Cys | Glu | Asp | Gln | Gly | Glu | Lys | Ser |
| | 1355 | | | | | 1360 | | | | 1365 | | | | |
| Leu | Gln | Leu | Val | Met | Glu | Tyr | Val | Pro | Leu | Gly | Ser | Leu | Arg | Asp |
| | 1370 | | | | | 1375 | | | | 1380 | | | | |
| Tyr | Leu | Pro | Arg | His | Ser | Ile | Gly | Leu | Ala | Gln | Leu | Leu | Leu | Phe |
| | 1385 | | | | | 1390 | | | | 1395 | | | | |
| Ala | Gln | Gln | Ile | Cys | Glu | Gly | Met | Ala | Tyr | Leu | His | Ala | His | Asp |
| | 1400 | | | | | 1405 | | | | 1410 | | | | |
| Tyr | Ile | His | Arg | Asp | Leu | Ala | Ala | Arg | Asn | Val | Leu | Leu | Asp | Asn |
| | 1415 | | | | | 1420 | | | | 1425 | | | | |
| Asp | Arg | Leu | Val | Lys | Ile | Gly | Asp | Phe | Gly | Leu | Ala | Lys | Ala | Val |

```
                   1430                1435                1440

Pro Glu Gly His Glu Tyr Tyr Arg Val Arg Glu Asp Gly Asp Ser
        1445                1450                1455

Pro Val Phe Trp Tyr Ala Pro Glu Cys Leu Lys Glu Tyr Lys Phe
        1460                1465                1470

Tyr Tyr Ala Ser Asp Val Trp Ser Phe Gly Val Thr Leu Tyr Glu
        1475                1480                1485

Leu Leu Thr His Cys Asp Ser Ser Gln Ser Pro Pro Thr Lys Phe
        1490                1495                1500

Leu Glu Leu Ile Gly Ile Ala Gln Gly Gln Met Thr Val Leu Arg
        1505                1510                1515

Leu Thr Glu Leu Leu Glu Arg Gly Glu Arg Leu Pro Arg Pro Asp
        1520                1525                1530

Lys Cys Pro Cys Glu Val Tyr His Leu Met Lys Asn Cys Trp Glu
        1535                1540                1545

Thr Glu Ala Ser Phe Arg Pro Thr Phe Glu Asn Leu Ile Pro Ile
        1550                1555                1560

Leu Lys Thr Val His Glu Lys Tyr Gln Gly Gln Ala Pro Ser Val
        1565                1570                1575

Phe Ser Val Cys Leu Glu Tyr Pro Tyr Asp Val Pro Asp Tyr Ala
        1580                1585                1590
```

<210> SEQ ID NO 31
<211> LENGTH: 1595
<212> TYPE: PRT
<213> ORGANISM: Artificial Sequence
<220> FEATURE:
<223> OTHER INFORMATION: ERN1(D123P)-Tyk2(K)-HA fusion protein

<400> SEQUENCE: 31

```
Met Pro Ala Arg Arg Leu Leu Leu Leu Thr Leu Leu Leu Pro Gly
1               5                   10                  15

Leu Gly Ile Phe Gly Ser Thr Ser Thr Val Thr Leu Pro Glu Thr Leu
                20                  25                  30

Leu Phe Val Ser Thr Leu Asp Gly Ser Leu His Ala Val Ser Lys Arg
        35                  40                  45

Thr Gly Ser Ile Lys Trp Thr Leu Lys Glu Asp Pro Val Leu Gln Val
    50                  55                  60

Pro Thr His Val Glu Glu Pro Ala Phe Leu Pro Asp Pro Asn Asp Gly
65                  70                  75                  80

Ser Leu Tyr Thr Leu Gly Ser Lys Asn Asn Glu Gly Leu Thr Lys Leu
                85                  90                  95

Pro Phe Thr Ile Pro Glu Leu Val Gln Ala Ser Pro Cys Arg Ser Ser
                100                 105                 110

Asp Gly Ile Leu Tyr Met Gly Lys Lys Gln Pro Ile Trp Tyr Val Ile
        115                 120                 125

Asp Leu Leu Thr Gly Glu Lys Gln Gln Thr Leu Ser Ser Ala Phe Ala
    130                 135                 140

Asp Ser Leu Cys Pro Ser Thr Ser Leu Leu Tyr Leu Gly Arg Thr Glu
145                 150                 155                 160

Tyr Thr Ile Thr Met Tyr Asp Thr Lys Thr Arg Glu Leu Arg Trp Asn
                165                 170                 175

Ala Thr Tyr Phe Asp Tyr Ala Ala Ser Leu Pro Glu Asp Asp Val Asp
                180                 185                 190

Tyr Lys Met Ser His Phe Val Ser Asn Gly Asp Gly Leu Val Val Thr
```

-continued

```
                195                 200                 205
    Val Asp Ser Glu Ser Gly Asp Val Leu Trp Ile Gln Asn Tyr Ala Ser
        210                 215                 220

Pro Val Ala Phe Tyr Val Trp Gln Arg Glu Gly Leu Arg Lys Val
    225                 230                 235                 240

Met His Ile Asn Val Ala Val Glu Thr Leu Arg Tyr Leu Thr Phe Met
                        245                 250                 255

Ser Gly Glu Val Gly Arg Ile Thr Lys Trp Lys Tyr Pro Phe Pro Lys
                260                 265                 270

Glu Thr Glu Ala Lys Ser Lys Leu Thr Pro Thr Leu Tyr Val Gly Lys
                275                 280                 285

Tyr Ser Thr Ser Leu Tyr Ala Ser Pro Ser Met Val His Glu Gly Val
                290                 295                 300

Ala Val Val Pro Arg Gly Ser Thr Leu Pro Leu Glu Gly Pro Gln
    305                 310                 315                 320

Thr Asp Gly Val Thr Ile Gly Asp Lys Gly Glu Cys Val Ile Thr Pro
                        325                 330                 335

Ser Thr Asp Val Lys Phe Asp Pro Gly Leu Lys Ser Lys Asn Lys Leu
                340                 345                 350

Asn Tyr Leu Arg Asn Tyr Trp Leu Ile Gly His His Glu Thr Pro
                355                 360                 365

Leu Ser Ala Ser Thr Lys Met Leu Glu Arg Phe Pro Asn Asn Leu Pro
    370                 375                 380

Lys His Arg Glu Asn Val Ile Pro Ala Asp Ser Glu Lys Lys Ser Phe
    385                 390                 395                 400

Glu Glu Val Ile Asn Leu Val Asp Gln Thr Ser Glu Asn Ala Pro Thr
                        405                 410                 415

Thr Val Ser Arg Asp Val Glu Glu Lys Pro Ala His Ala Pro Ala Arg
                        420                 425                 430

Pro Glu Ala Pro Val Asp Ser Met Leu Lys Asp Met Ala Thr Ile Ile
                        435                 440                 445

Leu Ser Thr Phe Leu Leu Ile Gly Trp Val Ala Phe Ile Ile Thr Tyr
    450                 455                 460

Pro Leu Ser Met His Gln Gln Gln Leu Gln His Gln Gln Phe Gln
    465                 470                 475                 480

Lys Glu Leu Glu Lys Ile Gln Leu Leu Gln Gln Gln Gln Gln Leu
                        485                 490                 495

Pro Phe His Pro Pro Asp Thr Ala Gln Asp Gly Glu Leu Leu Asp
                        500                 505                 510

Thr Ser Gly Pro Tyr Ser Glu Ser Gly Thr Ser Ser Pro Ser Thr
                515                 520                 525

Ser Pro Arg Ala Ser Asn His Ser Leu Cys Ser Gly Ser Ser Ala Ser
                530                 535                 540

Lys Ala Gly Ser Ser Pro Ser Leu Glu Gln Asp Asp Gly Asp Glu Glu
    545                 550                 555                 560

Thr Ser Val Val Ile Val Gly Lys Ile Ser Phe Cys Pro Lys Asp Val
                        565                 570                 575

Leu Gly His Gly Ala Glu Gly Thr Ile Val Tyr Arg Gly Met Phe Asp
                        580                 585                 590

Asn Arg Asp Val Ala Val Lys Arg Ile Leu Pro Glu Cys Phe Ser Phe
                595                 600                 605

Ala Asp Arg Glu Val Gln Leu Leu Arg Glu Ser Asp Glu His Pro Asn
    610                 615                 620
```

-continued

Val Ile Arg Tyr Phe Cys Thr Glu Lys Asp Arg Gln Phe Gln Tyr Ile
625                 630                 635                 640

Ala Ile Glu Leu Cys Ala Ala Thr Leu Gln Glu Tyr Val Glu Gln Lys
            645                 650                 655

Asp Phe Ala His Leu Gly Leu Glu Pro Ile Thr Leu Gln Gln Thr
        660                 665                 670

Thr Ser Gly Leu Ala His Leu His Ser Leu Asn Ile Val His Arg Asp
    675                 680                 685

Leu Lys Pro His Asn Ile Leu Ile Ser Met Pro Asn Ala His Gly Lys
690                 695                 700

Ile Lys Ala Met Ile Ser Asp Phe Gly Leu Cys Lys Lys Leu Ala Val
705                 710                 715                 720

Gly Arg His Ser Phe Ser Arg Arg Ser Gly Val Pro Gly Thr Glu Gly
                725                 730                 735

Trp Ile Ala Pro Glu Met Leu Ser Glu Asp Cys Lys Glu Asn Pro Thr
            740                 745                 750

Tyr Thr Val Asp Ile Phe Ser Ala Gly Cys Val Phe Tyr Tyr Val Ile
        755                 760                 765

Ser Glu Gly Ser His Pro Phe Gly Lys Ser Leu Gln Arg Gln Ala Asn
770                 775                 780

Ile Leu Leu Gly Ala Cys Ser Leu Asp Cys Leu His Pro Glu Lys His
785                 790                 795                 800

Glu Asp Val Ile Ala Arg Glu Leu Ile Glu Lys Met Ile Ala Met Asp
                805                 810                 815

Pro Gln Lys Arg Pro Ser Ala Lys His Val Leu Lys His Pro Phe Phe
            820                 825                 830

Trp Ser Leu Glu Lys Gln Leu Gln Phe Phe Gln Asp Val Ser Asp Arg
        835                 840                 845

Ile Glu Lys Glu Ser Leu Asp Gly Pro Ile Val Lys Gln Leu Glu Arg
850                 855                 860

Gly Gly Arg Ala Val Val Lys Met Asp Trp Arg Glu Asn Ile Thr Val
865                 870                 875                 880

Pro Leu Gln Thr Asp Leu Arg Lys Phe Arg Thr Tyr Lys Gly Gly Ser
                885                 890                 895

Val Arg Asp Leu Leu Arg Ala Met Arg Asn Lys Lys His His Tyr Arg
            900                 905                 910

Glu Leu Pro Ala Glu Val Arg Glu Thr Leu Gly Ser Leu Pro Asp Asp
        915                 920                 925

Phe Val Cys Tyr Phe Thr Ser Arg Phe Pro His Leu Leu Ala His Thr
930                 935                 940

Tyr Arg Ala Met Glu Leu Cys Ser His Glu Arg Leu Phe Gln Pro Tyr
945                 950                 955                 960

Tyr Phe His Glu Pro Pro Glu Pro Gln Pro Val Thr Pro Asp Ala
                965                 970                 975

Leu Ala Ser Ala Ala Ala Gly Gly Ser Ile Thr Gln Leu Ser His Leu
        980                 985                 990

Gly Gln Gly Thr Arg Thr Asn Val Tyr Glu Gly Arg Leu Arg Val Glu
    995                 1000                1005

Gly Ser Gly Asp Pro Glu Glu Gly Lys Met Asp Asp Glu Asp Pro
    1010                1015                1020

Leu Val Pro Gly Arg Asp Arg Gly Gln Glu Leu Arg Val Val Leu
    1025                1030                1035

-continued

```
Lys Val Leu Asp Pro Ser His His Asp Ile Ala Leu Ala Phe Tyr
    1040            1045            1050

Glu Thr Ala Ser Leu Met Ser Gln Val Ser His Thr His Leu Ala
    1055            1060            1065

Phe Val His Gly Val Cys Val Arg Gly Pro Glu Asn Ser Met Val
    1070            1075            1080

Thr Glu Tyr Val Glu His Gly Pro Leu Asp Val Trp Leu Arg Arg
    1085            1090            1095

Glu Arg Gly His Val Pro Met Ala Trp Lys Met Val Val Ala Gln
    1100            1105            1110

Gln Leu Ala Ser Ala Leu Ser Tyr Leu Glu Asn Lys Asn Leu Val
    1115            1120            1125

His Gly Asn Val Cys Gly Arg Asn Ile Leu Leu Ala Arg Leu Gly
    1130            1135            1140

Leu Ala Glu Gly Thr Ser Pro Phe Ile Lys Leu Ser Asp Pro Gly
    1145            1150            1155

Val Gly Leu Gly Ala Leu Ser Arg Glu Glu Arg Val Glu Arg Ile
    1160            1165            1170

Pro Trp Leu Ala Pro Glu Cys Leu Pro Gly Gly Ala Asn Ser Leu
    1175            1180            1185

Ser Thr Ala Met Asp Lys Trp Gly Phe Gly Ala Thr Leu Leu Glu
    1190            1195            1200

Ile Cys Phe Asp Gly Glu Ala Pro Leu Gln Ser Arg Ser Pro Ser
    1205            1210            1215

Glu Lys Glu His Phe Tyr Gln Arg Gln His Arg Leu Pro Glu Pro
    1220            1225            1230

Ser Cys Pro Gln Leu Ala Thr Leu Thr Ser Gln Cys Leu Thr Tyr
    1235            1240            1245

Glu Pro Thr Gln Arg Pro Ser Phe Arg Thr Ile Leu Arg Asp Leu
    1250            1255            1260

Thr Arg Val Gln Pro His Asn Leu Ala Asp Val Leu Thr Val Asn
    1265            1270            1275

Arg Asp Ser Pro Ala Val Gly Pro Thr Thr Phe His Lys Arg Tyr
    1280            1285            1290

Leu Lys Lys Ile Arg Asp Leu Gly Glu Gly His Phe Gly Lys Val
    1295            1300            1305

Ser Leu Tyr Cys Tyr Asp Pro Thr Asn Asp Gly Thr Gly Glu Met
    1310            1315            1320

Val Ala Val Lys Ala Leu Lys Ala Asp Cys Gly Pro Gln His Arg
    1325            1330            1335

Ser Gly Trp Lys Gln Glu Ile Asp Ile Leu Arg Thr Leu Tyr His
    1340            1345            1350

Glu His Ile Ile Lys Tyr Lys Gly Cys Cys Glu Asp Gln Gly Glu
    1355            1360            1365

Lys Ser Leu Gln Leu Val Met Glu Tyr Val Pro Leu Gly Ser Leu
    1370            1375            1380

Arg Asp Tyr Leu Pro Arg His Ser Ile Gly Leu Ala Gln Leu Leu
    1385            1390            1395

Leu Phe Ala Gln Gln Ile Cys Glu Gly Met Ala Tyr Leu His Ala
    1400            1405            1410

His Asp Tyr Ile His Arg Asp Leu Ala Ala Arg Asn Val Leu Leu
    1415            1420            1425

Asp Asn Asp Arg Leu Val Lys Ile Gly Asp Phe Gly Leu Ala Lys
```

```
                    1430               1435               1440

Ala Val Pro Glu Gly His Glu Tyr Tyr Arg Val Arg Glu Asp Gly
        1445               1450               1455

Asp Ser Pro Val Phe Trp Tyr Ala Pro Glu Cys Leu Lys Glu Tyr
    1460               1465               1470

Lys Phe Tyr Tyr Ala Ser Asp Val Trp Ser Phe Gly Val Thr Leu
    1475               1480               1485

Tyr Glu Leu Leu Thr His Cys Asp Ser Ser Gln Ser Pro Pro Thr
    1490               1495               1500

Lys Phe Leu Glu Leu Ile Gly Ile Ala Gln Gly Gln Met Thr Val
    1505               1510               1515

Leu Arg Leu Thr Glu Leu Leu Glu Arg Gly Glu Arg Leu Pro Arg
    1520               1525               1530

Pro Asp Lys Cys Pro Cys Glu Val Tyr His Leu Met Lys Asn Cys
    1535               1540               1545

Trp Glu Thr Glu Ala Ser Phe Arg Pro Thr Phe Glu Asn Leu Ile
    1550               1555               1560

Pro Ile Leu Lys Thr Val His Glu Lys Tyr Gln Gly Gln Ala Pro
    1565               1570               1575

Ser Val Phe Ser Val Cys Leu Glu Tyr Pro Tyr Asp Val Pro Asp
    1580               1585               1590

Tyr Ala
    1595

<210> SEQ ID NO 32
<211> LENGTH: 309
<212> TYPE: PRT
<213> ORGANISM: Artificial Sequence
<220> FEATURE:
<223> OTHER INFORMATION: flag tag-gp130-VAMP1 construct

<400> SEQUENCE: 32

Met Asp Tyr Lys Asp Asp Asp Lys Ile Ser Thr Val Val His Ser
1               5                   10                  15

Gly Tyr Arg His Gln Val Pro Ser Val Gln Val Phe Ser Arg Ser Glu
            20                  25                  30

Ser Thr Gln Pro Leu Leu Asp Ser Glu Glu Arg Pro Glu Asp Leu Gln
        35                  40                  45

Leu Val Asp His Val Asp Gly Gly Asp Gly Ile Leu Pro Arg Gln Gln
    50                  55                  60

Tyr Phe Lys Gln Asn Cys Ser Gln His Glu Ser Ser Pro Asp Ile Ser
65                  70                  75                  80

His Phe Glu Arg Ser Lys Gln Val Ser Ser Val Asn Glu Glu Asp Phe
                85                  90                  95

Val Arg Leu Lys Gln Gln Ile Ser Asp His Ile Ser Gln Ser Cys Gly
            100                 105                 110

Ser Gly Gln Met Lys Met Phe Gln Glu Val Ser Ala Ala Asp Ala Phe
        115                 120                 125

Gly Pro Gly Thr Glu Gly Gln Val Glu Arg Phe Glu Thr Val Gly Met
    130                 135                 140

Glu Ala Ala Thr Asp Glu Gly Met Pro Lys Ser Tyr Leu Pro Gln Thr
145                 150                 155                 160

Val Arg Gln Gly Gly Tyr Met Pro Gln Gly Gly Ser Glu Leu Ser Thr
                165                 170                 175

Ser Leu Tyr Lys Lys Val Gly Met Ser Ala Pro Ala Gln Pro Pro Ala
```

```
            180                 185                 190
Glu Gly Thr Glu Gly Thr Ala Pro Gly Gly Pro Pro Gly Pro Pro
                195                 200                 205

Pro Asn Met Thr Ser Asn Arg Arg Leu Gln Gln Thr Gln Ala Gln Val
        210                 215                 220

Glu Glu Val Val Asp Ile Ile Arg Val Asn Val Asp Lys Val Leu Glu
225                 230                 235                 240

Arg Asp Gln Lys Leu Ser Glu Leu Asp Asp Arg Ala Asp Ala Leu Gln
                245                 250                 255

Ala Gly Ala Ser Gln Phe Glu Ser Ser Ala Ala Lys Leu Lys Arg Lys
        260                 265                 270

Tyr Trp Trp Lys Asn Cys Lys Met Met Ile Met Leu Gly Ala Ile Cys
                275                 280                 285

Ala Ile Ile Val Val Val Ile Val Ser Lys Tyr Arg Cys Pro Thr Phe
        290                 295                 300

Leu Tyr Lys Val Val
305

<210> SEQ ID NO 33
<211> LENGTH: 308
<212> TYPE: PRT
<213> ORGANISM: Artificial Sequence
<220> FEATURE:
<223> OTHER INFORMATION: flag tag-gp130-VAMP2 fusion construct

<400> SEQUENCE: 33

Met Asp Tyr Lys Asp Asp Asp Lys Ile Ser Thr Val Val His Ser
1               5                  10                  15

Gly Tyr Arg His Gln Val Pro Ser Val Gln Val Phe Ser Arg Ser Glu
                20                  25                  30

Ser Thr Gln Pro Leu Leu Asp Ser Glu Glu Arg Pro Glu Asp Leu Gln
        35                  40                  45

Leu Val Asp His Val Asp Gly Gly Asp Gly Ile Leu Pro Arg Gln Gln
    50                  55                  60

Tyr Phe Lys Gln Asn Cys Ser Gln His Glu Ser Ser Pro Asp Ile Ser
65                  70                  75                  80

His Phe Glu Arg Ser Lys Gln Val Ser Ser Val Asn Glu Glu Asp Phe
                85                  90                  95

Val Arg Leu Lys Gln Gln Ile Ser Asp His Ile Ser Gln Ser Cys Gly
            100                 105                 110

Ser Gly Gln Met Lys Met Phe Gln Glu Val Ser Ala Ala Asp Ala Phe
        115                 120                 125

Gly Pro Gly Thr Glu Gly Gln Val Glu Arg Phe Glu Thr Val Gly Met
    130                 135                 140

Glu Ala Ala Thr Asp Glu Gly Met Pro Lys Ser Tyr Leu Pro Gln Thr
145                 150                 155                 160

Val Arg Gln Gly Gly Tyr Met Pro Gln Gly Gly Ser Glu Leu Ser Thr
                165                 170                 175

Ser Leu Tyr Lys Lys Val Gly Met Ser Ala Thr Ala Ala Thr Ala Pro
            180                 185                 190

Pro Ala Pro Ala Gly Glu Gly Gly Pro Ala Pro Pro Asn
        195                 200                 205

Leu Thr Ser Asn Arg Arg Leu Gln Gln Thr Gln Ala Gln Val Asp Glu
    210                 215                 220

Val Val Asp Ile Met Arg Val Asn Val Asp Lys Val Leu Glu Arg Asp
```

```
225             230             235             240

Gln Lys Leu Ser Glu Leu Asp Asp Arg Ala Asp Ala Leu Gln Ala Gly
                245                 250                 255

Ala Ser Gln Phe Glu Thr Ser Ala Ala Lys Leu Lys Arg Lys Tyr Trp
                260                 265                 270

Trp Lys Asn Leu Lys Met Met Ile Ile Leu Gly Val Ile Cys Ala Ile
                275                 280                 285

Ile Leu Ile Ile Ile Ile Val Tyr Phe Ser Thr Tyr Pro Thr Phe Leu
                290                 295                 300

Tyr Lys Val Val
305

<210> SEQ ID NO 34
<211> LENGTH: 617
<212> TYPE: PRT
<213> ORGANISM: Artificial Sequence
<220> FEATURE:
<223> OTHER INFORMATION: flag-tag-ERN1cyt-gp130 fusion construct

<400> SEQUENCE: 34

Met Asp Tyr Lys Asp Asp Asp Lys Ile Ser Glu Phe Phe Cys Pro
1               5                   10                  15

Lys Asp Val Leu Gly His Gly Ala Glu Gly Thr Ile Val Tyr Arg Gly
                20                  25                  30

Met Phe Asp Asn Arg Asp Val Ala Val Lys Arg Ile Leu Pro Glu Cys
                35                  40                  45

Phe Ser Phe Ala Asp Arg Glu Val Gln Leu Leu Arg Glu Ser Asp Glu
50                  55                  60

His Pro Asn Val Ile Arg Tyr Phe Cys Thr Glu Lys Asp Arg Gln Phe
65                  70                  75                  80

Gln Tyr Ile Ala Ile Glu Leu Cys Ala Ala Thr Leu Gln Glu Tyr Val
                85                  90                  95

Glu Gln Lys Asp Phe Ala His Leu Gly Leu Glu Pro Ile Thr Leu Leu
                100                 105                 110

Gln Gln Thr Thr Ser Gly Leu Ala His Leu His Ser Leu Asn Ile Val
                115                 120                 125

His Arg Asp Leu Lys Pro His Asn Ile Leu Ile Ser Met Pro Asn Ala
130                 135                 140

His Gly Lys Ile Lys Ala Met Ile Ser Asp Phe Gly Leu Cys Lys Lys
145                 150                 155                 160

Leu Ala Val Gly Arg His Ser Phe Ser Arg Arg Ser Gly Val Pro Gly
                165                 170                 175

Thr Glu Gly Trp Ile Ala Pro Glu Met Leu Ser Glu Asp Cys Lys Glu
                180                 185                 190

Asn Pro Thr Tyr Thr Val Asp Ile Phe Ser Ala Gly Cys Val Phe Tyr
                195                 200                 205

Tyr Val Ile Ser Glu Gly Ser His Pro Phe Gly Lys Ser Leu Gln Arg
                210                 215                 220

Gln Ala Asn Ile Leu Leu Gly Ala Cys Ser Leu Asp Cys Leu His Pro
225                 230                 235                 240

Glu Lys His Glu Asp Val Ile Ala Arg Glu Leu Ile Glu Lys Met Ile
                245                 250                 255

Ala Met Asp Pro Gln Lys Arg Pro Ser Ala Lys His Val Leu Lys His
                260                 265                 270

Pro Phe Phe Trp Ser Leu Glu Lys Gln Leu Gln Phe Phe Gln Asp Val
```

Ser Asp Arg Ile Glu Lys Glu Ser Leu Asp Gly Pro Ile Val Lys Gln
    275                 280                 285

Leu Glu Arg Gly Gly Arg Ala Val Val Lys Met Asp Trp Arg Glu Asn
290                 295                 300

Ile Thr Val Pro Leu Gln Thr Asp Leu Arg Lys Phe Arg Thr Tyr Lys
305                 310                 315                 320

Gly Gly Ser Val Arg Asp Leu Leu Arg Ala Met Arg Asn Lys Lys His
            325                 330                 335

His Tyr Arg Glu Leu Pro Ala Glu Val Arg Glu Thr Leu Gly Ser Leu
        340                 345                 350

Pro Asp Asp Phe Val Cys Tyr Phe Thr Ser Arg Phe Pro His Leu Leu
    355                 360                 365

Ala His Thr Tyr Arg Ala Met Glu Leu Cys Ser His Glu Arg Leu Phe
370                 375                 380

Gln Pro Tyr Tyr Phe His Glu Pro Pro Glu Pro Gln Pro Pro Val Thr
385                 390                 395                 400

Pro Asp Ala Leu Pro Ser Arg Gly Ser Gly Gly Ser Gly Gly Ser Thr
            405                 410                 415

Val Val His Ser Gly Tyr Arg His Gln Val Pro Ser Val Gln Val Phe
        420                 425                 430

Ser Arg Ser Glu Ser Thr Gln Pro Leu Leu Asp Ser Glu Glu Arg Pro
    435                 440                 445

Glu Asp Leu Gln Leu Val Asp His Val Asp Gly Gly Asp Gly Ile Leu
450                 455                 460

Pro Arg Gln Gln Tyr Phe Lys Gln Asn Cys Ser Gln His Glu Ser Ser
465                 470                 475                 480

Pro Asp Ile Ser His Phe Glu Arg Ser Lys Gln Val Ser Ser Val Asn
            485                 490                 495

Glu Glu Asp Phe Val Arg Leu Lys Gln Gln Ile Ser Asp His Ile Ser
        500                 505                 510

Gln Ser Cys Gly Ser Gly Gln Met Lys Met Phe Gln Glu Val Ser Ala
    515                 520                 525

Ala Asp Ala Phe Gly Pro Gly Thr Glu Gly Gln Val Glu Arg Phe Glu
530                 535                 540

Thr Val Gly Met Glu Ala Ala Thr Asp Glu Gly Met Pro Lys Ser Tyr
545                 550                 555                 560

Leu Pro Gln Thr Val Arg Gln Gly Gly Tyr Met Pro Gln Gly Gly Ser
            565                 570                 575

Glu Leu Ser Thr Ser Leu Tyr Lys Lys Ala Gly Tyr Leu Pro Gln Thr
        580                 585                 590

Val Arg Gln Gly Gly Tyr Met Pro Gln
    595                 600                 605

<210> SEQ ID NO 35
<211> LENGTH: 645
<212> TYPE: PRT
<213> ORGANISM: Artificial Sequence
<220> FEATURE:
<223> OTHER INFORMATION: flag tag-gp130-RTp51 fusion construct

<400> SEQUENCE: 35

Met Asp Tyr Lys Asp Asp Asp Lys Ile Ser Thr Val Val His Ser
1               5                   10                  15

Gly Tyr Arg His Gln Val Pro Ser Val Gln Val Phe Ser Arg Ser Glu

-continued

```
                20                  25                  30
Ser Thr Gln Pro Leu Leu Asp Ser Glu Glu Arg Pro Glu Asp Leu Gln
            35                  40                  45
Leu Val Asp His Val Asp Gly Asp Gly Ile Leu Pro Arg Gln Gln
        50                  55                  60
Tyr Phe Lys Gln Asn Cys Ser Gln His Glu Ser Ser Pro Asp Ile Ser
 65                  70                  75                  80
His Phe Glu Arg Ser Lys Gln Val Ser Ser Val Asn Glu Glu Asp Phe
                85                  90                  95
Val Arg Leu Lys Gln Gln Ile Ser Asp His Ile Ser Gln Ser Cys Gly
            100                 105                 110
Ser Gly Gln Met Lys Met Phe Gln Glu Val Ser Ala Ala Asp Ala Phe
            115                 120                 125
Gly Pro Gly Thr Glu Gly Gln Val Glu Arg Phe Glu Thr Val Gly Met
            130                 135                 140
Glu Ala Ala Thr Asp Glu Gly Met Pro Lys Ser Tyr Leu Pro Gln Thr
145                 150                 155                 160
Val Arg Gln Gly Gly Tyr Met Pro Gln Gly Gly Ser Glu Leu Ser Thr
                165                 170                 175
Ser Leu Tyr Lys Lys Ala Gly Tyr Leu Pro Gln Thr Val Arg Gln Gly
            180                 185                 190
Gly Tyr Met Pro Gln Gly Gly Ser Glu Phe Gly Ser Ser Pro Ile Ser
            195                 200                 205
Pro Ile Glu Thr Val Pro Val Lys Leu Lys Pro Gly Met Asp Gly Pro
            210                 215                 220
Lys Val Lys Gln Trp Pro Leu Thr Glu Glu Lys Ile Lys Ala Leu Val
225                 230                 235                 240
Glu Ile Cys Thr Glu Met Glu Lys Glu Gly Lys Ile Ser Lys Ile Gly
                245                 250                 255
Pro Glu Asn Pro Tyr Asn Thr Pro Val Phe Ala Ile Lys Lys Lys Asp
            260                 265                 270
Ser Thr Lys Trp Arg Lys Leu Val Asp Phe Arg Glu Leu Asn Lys Arg
            275                 280                 285
Thr Gln Asp Phe Trp Glu Val Gln Leu Gly Ile Pro His Pro Ala Gly
            290                 295                 300
Leu Lys Gln Lys Lys Ser Val Thr Val Leu Asp Val Gly Asp Ala Tyr
305                 310                 315                 320
Phe Ser Val Pro Leu Asp Lys Asp Phe Arg Lys Tyr Thr Ala Phe Thr
                325                 330                 335
Ile Pro Ser Ile Asn Asn Glu Thr Pro Gly Ile Arg Tyr Gln Tyr Asn
            340                 345                 350
Val Leu Pro Gln Gly Trp Lys Gly Ser Pro Ala Ile Phe Gln Cys Ser
            355                 360                 365
Met Thr Lys Ile Leu Glu Pro Phe Arg Lys Gln Asn Pro Asp Ile Val
            370                 375                 380
Ile Tyr Gln Tyr Met Asp Asp Leu Tyr Val Gly Ser Asp Leu Glu Ile
385                 390                 395                 400
Gly Gln His Arg Thr Lys Ile Glu Glu Leu Arg Gln His Leu Leu Arg
                405                 410                 415
Trp Gly Phe Thr Thr Pro Asp Lys Lys His Gln Lys Glu Pro Pro Phe
            420                 425                 430
Leu Trp Met Gly Tyr Glu Leu His Pro Asp Lys Trp Thr Val Gln Pro
            435                 440                 445
```

```
Ile Val Leu Pro Glu Lys Asp Ser Trp Thr Val Asn Asp Ile Gln Lys
    450                 455                 460

Leu Val Gly Lys Leu Asn Trp Ala Ser Gln Ile Tyr Ala Gly Ile Lys
465                 470                 475                 480

Val Arg Gln Leu Cys Lys Leu Leu Arg Gly Thr Lys Ala Leu Thr Glu
                485                 490                 495

Val Val Pro Leu Thr Glu Glu Ala Glu Leu Glu Leu Ala Glu Asn Arg
            500                 505                 510

Glu Ile Leu Lys Glu Pro Val His Gly Val Tyr Tyr Asp Pro Ser Lys
        515                 520                 525

Asp Leu Ile Ala Glu Ile Gln Lys Gln Gly Gln Gly Gln Trp Thr Tyr
530                 535                 540

Gln Ile Tyr Gln Glu Pro Phe Lys Asn Leu Lys Thr Gly Lys Tyr Ala
545                 550                 555                 560

Arg Met Lys Gly Ala His Thr Asn Asp Val Lys Gln Leu Thr Glu Ala
                565                 570                 575

Val Gln Lys Ile Ala Thr Glu Ser Ile Val Ile Trp Gly Lys Thr Pro
            580                 585                 590

Lys Phe Lys Leu Pro Ile Gln Lys Glu Thr Trp Glu Ala Trp Trp Thr
        595                 600                 605

Glu Tyr Trp Gln Ala Thr Trp Ile Pro Glu Trp Glu Phe Val Asn Thr
610                 615                 620

Pro Pro Leu Val Lys Leu Trp Tyr Gln Leu Glu Lys Glu Pro Ile Ile
625                 630                 635                 640

Gly Ala Glu Thr Phe
                645

<210> SEQ ID NO 36
<211> LENGTH: 174
<212> TYPE: PRT
<213> ORGANISM: Artificial Sequence
<220> FEATURE:
<223> OTHER INFORMATION: polypeptide encoded by pMG1 plasmid

<400> SEQUENCE: 36

Met Asp Tyr Lys Asp Asp Asp Lys Ile Ser Thr Val Val His Ser
1               5                   10                  15

Gly Tyr Arg His Gln Val Pro Ser Val Gln Val Phe Ser Arg Ser Glu
                20                  25                  30

Ser Thr Gln Pro Leu Leu Asp Ser Glu Glu Arg Pro Glu Asp Leu Gln
            35                  40                  45

Leu Val Asp His Val Asp Gly Asp Gly Ile Leu Pro Arg Gln Gln
50                  55                  60

Tyr Phe Lys Gln Asn Cys Ser Gln His Glu Ser Pro Asp Ile Ser
65                  70                  75                  80

His Phe Glu Arg Ser Lys Gln Val Ser Ser Val Asn Glu Glu Asp Phe
                85                  90                  95

Val Arg Leu Lys Gln Gln Ile Ser Asp His Ile Ser Gln Ser Cys Gly
                100                 105                 110

Ser Gly Gln Met Lys Met Phe Gln Glu Val Ser Ala Ala Asp Ala Phe
            115                 120                 125

Gly Pro Gly Thr Glu Gly Gln Val Glu Arg Phe Glu Thr Val Gly Met
        130                 135                 140

Glu Ala Ala Thr Asp Glu Gly Met Pro Lys Ser Tyr Leu Pro Gln Thr
145                 150                 155                 160
```

```
Val Arg Gln Gly Gly Tyr Met Pro Gln Gly Gly Ser Glu Phe
            165                 170

<210> SEQ ID NO 37
<211> LENGTH: 202
<212> TYPE: PRT
<213> ORGANISM: Artificial Sequence
<220> FEATURE:
<223> OTHER INFORMATION: polypeptide encoded by pMG2 plasmid

<400> SEQUENCE: 37

Met Asp Tyr Lys Asp Asp Asp Lys Ile Ser Thr Val Val His Ser
1               5                   10                  15

Gly Tyr Arg His Gln Val Pro Ser Val Gln Val Phe Ser Arg Ser Glu
                20                  25                  30

Ser Thr Gln Pro Leu Leu Asp Ser Glu Glu Arg Pro Glu Asp Leu Gln
            35                  40                  45

Leu Val Asp His Val Asp Gly Gly Asp Gly Ile Leu Pro Arg Gln Gln
    50                  55                  60

Tyr Phe Lys Gln Asn Cys Ser Gln His Glu Ser Ser Pro Asp Ile Ser
65                  70                  75                  80

His Phe Glu Arg Ser Lys Gln Val Ser Ser Val Asn Glu Glu Asp Phe
                85                  90                  95

Val Arg Leu Lys Gln Gln Ile Ser Asp His Ile Ser Gln Ser Cys Gly
                100                 105                 110

Ser Gly Gln Met Lys Met Phe Gln Glu Val Ser Ala Ala Asp Ala Phe
            115                 120                 125

Gly Pro Gly Thr Glu Gly Gln Val Glu Arg Phe Glu Thr Val Gly Met
    130                 135                 140

Glu Ala Ala Thr Asp Glu Gly Met Pro Lys Ser Tyr Leu Pro Gln Thr
145                 150                 155                 160

Val Arg Gln Gly Gly Tyr Met Pro Gln Gly Gly Ser Glu Leu Ser Thr
                165                 170                 175

Ser Leu Tyr Lys Lys Ala Gly Tyr Leu Pro Gln Thr Val Arg Gln Gly
            180                 185                 190

Gly Tyr Met Pro Gln Gly Gly Ser Glu Phe
        195                 200
```